United States Patent [19]

Wilson et al.

[11] Patent Number: 5,585,362
[45] Date of Patent: Dec. 17, 1996

[54] ADENOVIRUS VECTORS FOR GENE THERAPY

[75] Inventors: James M. Wilson, Gladwyne; John Engelhardt, Havertown, both of Pa.

[73] Assignee: The Regents Of The University Of Michigan, Ann Arbor, Mich.

[21] Appl. No.: 73,354

[22] Filed: Jun. 7, 1993

Related U.S. Application Data

[63] Continuation-in-part of Ser. No. 943,952, Sep. 11, 1992, abandoned, and a continuation-in-part of Ser. No. 67,296, May 25, 1993, abandoned, which is a division of Ser. No. 584,275, Sep. 18, 1990, Pat. No. 5,240,846, which is a continuation-in-part of Ser. No. 401,609, Aug. 31, 1989, abandoned, which is a continuation-in-part of Ser. No. 399,945, Aug. 24, 1989, abandoned, which is a continuation-in-part of Ser. No. 396,894, Aug. 22, 1989, abandoned.

[51] Int. Cl.⁶ ............................. A61K 48/00; C12N 5/16; C12N 15/63
[52] U.S. Cl. ...................... 514/44; 435/320.1; 435/172.3; 435/240.2
[58] Field of Search ............................. 435/320.1, 172.3, 435/240.2; 424/93.1, 93.2

[56] References Cited

U.S. PATENT DOCUMENTS

| | | |
|---|---|---|
| 4,844,893 | 7/1989 | Honsik et al. . |
| 4,847,201 | 7/1989 | Kaswasaki et al. . |
| 4,853,331 | 8/1989 | Herrnstadt et al. . |
| 4,861,719 | 8/1989 | Miller . |
| 4,861,859 | 8/1989 | Ju . |
| 4,868,116 | 9/1989 | Morgan et al. . |
| 4,980,286 | 12/1990 | Morgan et al. . |
| 5,240,846 | 8/1993 | Collins et al. ...................... 435/240.1 |

FOREIGN PATENT DOCUMENTS

| | | |
|---|---|---|
| 2203742 | 4/1987 | United Kingdom . |
| WO9412649 | 6/1994 | WIPO . |

OTHER PUBLICATIONS

Boat et al., "Human Respiratory Tract Secretions", *Arch. Biochem. Biophys.* 177:95–104 (1976).

Boucher et al., "Na⁺ Transport In Cystic Fibrosis Respiratory Epithelia", *J. Clin. Invest.* 78:1245–1252 (1986).

Cheng et al., "Increased Sulfation Of Glycoconjugates By Cultured Nasal Epithelial Cells From Patients With Cystic Fibrosis", *J. Clin. Invest.* 84:68–72 (1989).

Cliff et al., "Separate Cl Conductances Activated By cAMP and Ca²⁺ in Cl⁻–Secreting Epithelial Cells", *PNAS (USA)*87:4956–4960 (1990).

Collie et al., "Culture Of Sweat Gland Epithelial Cells From Normal Individuals And Patients With Cystic Fibrosis", *In Vitro Cell &Devel. Biol.* 21:597–602 (1985).

Collins et al., "Construction Of A General Human Chromosome Jumping Library, With Application To Cystic Fibrosis", *Science* 235:1046–1049 (1987).

Cutting et al., "A Cluster Of Cystic Fibrosis Mutations In The First Nucleotide–Binding Fold Of The Cystic Fibrosis Conductance Regulation Protein", *Nature* 346:366–368 (1990).

Dean et al., "Multiple Mutations In Highly Conserved Residues Are Found In Mildly Affected Cystic Fibrosis Patients", *Cell* 61:863–870 (1990).

Drumm et al., "Physical Mapping Of The Cystic Fibrosis Region By Pulsed–Field Gel Electrophoresis", *Genomics* 2:346–354 (1988).

Fienberg et al., "A Technique For Radiolabeling DNA Restriction Endonuclease Fragments To High Specific Activity", *Anal. Biochem.* 132:6–13 (1983).

Frizzell et al., "Cystic Fibrosis: A Disease Of Ion Channels?", *Trends Neurosci* 10:190–193 (1987).

Frizzell et al., "Altered Regulation Of Airway Epithelial Cell Chloride Channels In Cystic Fibrosis", *Science* 233:558–560 (1986).

Green et al., "Chromosomal Region Of The Cystic Fibrosis Gene In The Yeast Artificial Chromosomes: A Model For Human Genome Mapping", *Science* 250:94–98 (1990).

Harris et al., "Establishment Of A Tissue Culture System For Epithelial Cells Desired From Human Pancreas: A Model For The Study Of Cystic Fibrosis", *Cell* 87:695–703 (1987).

Hyde et al., "Structural Model For ATP–Binding Proteins Associated With Cystic Fibrosis, Multidrug Resistance And Bacterial Transport", *Nature* 346:362–365 (1990).

Kerem et al., "Identification Of The Cystic Fibrosis Gene: Genetic Analysis", *Science* 245:1073–1080 (1989).

Kerem et al., "Identification of Mutations in Regions Corresponding to the Two Putative Nucleotide (ATP)–Binding Folds Of The Cystic Fibrosis Gene", *PNAS (USA)*87:8447–8451 (1990).

Korman et al., "Expression Of Human Class II Major Histocompatibility Complex Antigens Using Retrovirus Vectors", *PNAS(USA)*85:2150–2154 (1987).

Li et al., "Cyclic AMP–Dependent Protein Kinase Opens Chloride Channels In Normal But Not Cystic Fibrosis Airway Epithelium", *Nature* 331:358–360 (1988).

(List continued on next page.)

*Primary Examiner*—Jacqueline M. Stone
*Assistant Examiner*—Andrew Milne
*Attorney, Agent, or Firm*—Harness, Dickey & Pierce, P.L.C.

[57] ABSTRACT

The present invention comprises an improved adenovirus vector and methods for making and using such vectors. The adenovirus vectors of the present invention retain at least a portion of the adenoviral E3 region, carry a deletion of at least a portion of the adenoviral E1 region. Vectors of the present invention preferably also include an additional deletion to accommodate a transgene and/or other mutations which result in reduced expression or over-expression of adenoviral protein and/or reduced viral replication. The vectors of the present invention further include a transgene operatively-linked thereto. By reducing or eliminating viral replication and viral protein expression, the immune response of the infected host to the virus and viral protein is decreased and persistence of transgene expression can be increased. The adenovirus vectors of the present invention are thus particularly useful in gene transfer and therapy.

5 Claims, 15 Drawing Sheets

OTHER PUBLICATIONS

Quinton et al., "Cystic Fibrosis: A Disease In Electrolyte Transport", *FASEB J.* 4:2709–2717 (1990).

Riordan et al., "Identification Of The Cystic Fibrosis Gene: Cloning And Characterization Of Complementary DNA", *Science* 245:1066–1073 (1989).

Riordan et al., *Genetics And Epithelial Cell Dysfunction In Cystic Fibrosis*, 59–71 (1987).

Rommens et al., "Identification Of The Cystic Fibrosis Gene: Chromosome Walking And Jumping", *Science* 245:1059–1065 (1989).

Sanbrook et al., "Oligonucleotide–Mediated Mutagenesis", *Molecular Cloning, A Laboratory Manual* 2nd Ed., Cold Spring Harbor Press, 15.51–15.80 (1989).

Sato et al., "Defective Beta Adrenergic Response Of Cystic Fibrosis Sweat Glands In Vivo And In Vitro", *J. Clin. Invest.* 73:1763–1771 (1984).

Schoumacher et al., "A Cystic Fibrosis Pancreatic Adenocarcinoma Cell Line", *PNAS (USA)* 87:4012–4016 (1990).

Smith et al., "In Vitro Mutagenesis", *Annu. Re. Genet.* 19:423–462 (1985).

Stutts et al., "Chloride Uptake Into Cultured Airway Epithelial Cells From Cystic Fibrosis Patients And Normal Individuals", *PNAS (USA)* 82:6677–6681 (1985).

Taussig et al., "Cystic Fibrosis: An Overview", *In Cystic Fibrosis*, L. M. Taussig, ed. New York: Thieme–Stralton 1–9 (1984).

Tsui et al., "Cystic Fibrosis Locus Defined By A GEnetically Linked Polymorphic DNA Marker", *Science* 230:1054–1057 (1985).

Venglarik et al., "A Simple Assay For Agonist–Regulated Cl and K Conductances In Salt–Secreting Epithelial Cells", *Am. J. Physiol.* 259:C358–C364 (1990).

Welsh et al., "Abnormal Regulation Of Ion Channels In Cystic Fibrosis Epithelia", *FASEB J.* 4:2718–2725 (1990).

Welsh et al., "Chloride And Potassium Channels In Cystic Fibrosis Airway Epithelia", *Nature* 322:467–470 (1986).

White et al., "A Frame–Shift Mutation In The Cystic Fibrosis Gene", *Nature* 344:655–667 (1990).

Willumsen et al., "Activation Of An Apical Cl⁻ Conductance By $Ca^{2+}$ Ionophores In Cystic Fibrosis Airway Epithelia", *Am. J. Physiol.* 256:C226–C233 (1989).

Wilson et al., "Correction Of CD18–Deficient Lymphocytes By Retrovirus–Mediated Gene Transfer", *Science* 248:1413–1416 (1990).

Wilson et al., "Correction Of The Genetic Defect In Hepatocytes From The Watanabe Heritable Hyperlipidemic Rabbit", *PNAS (USA)* 85:4421–4425 (1988).

Wilson et al., "Expression Of Human Adenosine Deaminase In Mice Reconstituted With Retrovirus–Transduced Hematopoietic Stem Cells", *PNAS (USA)* 87:439–443 (1990)."The Cystic Fibrosis Genetic Analysis Consortium", *Am. J. Hum. Genet.* 47:354–359 (1990).

Schoumacher et al., "Phosphorylation Fails To Activate Chloride Channels From Cystic Fibrosis Airway Cells", *Nature* 330:752–754 (1987).

Jetten et al., "Persistence Of Abnormal Chloride Conductance Regulation in Transformed Cystic Fibrosis Epithelia", *Science* 244:1472 (1989).

Engelhardt, J. F. et al., "Ablation of E2A in Recombinant Adenoviruses Improves Transgene Persistence and Decreases Inflammatory Response in Mouse Liver," *PNAS(USA)* 91:6196–6200 (1994).

Engelhardt, J. F. et al., "Prolonged Transgene Expression in Cotton Rat Lung with Recombinant Adenoviruses Defective in E2a," *Human Gene Therapy* 5:1217–1229 (1994).

Goldman, M. J. et al., "Transfer of the CFTR Gene to the Lung of Nonhuman Primates with E1—Deleted, E2a—Defective Recombinant Adenoviruses: a Preclinical Toxicology Study," *Human Gene Therapy* 6:839–851 (1995).

Goldman, M. J. et al., "Gene Therapy in a Xenograft Model of Cystic Fibrosis Lung Corrects Chloride Transport More Effectively than the Sodium Defect," *Nature Genet.* 9:126–131 (1995).

Berkner, K. L., "Development of Adenovirus Vectors for the Expression of Heterologous Genes," *Biotechniques* 6:616–629 (1988).

Engelhardt, J. E. et al., "In Vivo Retroviral Gene Transfer into Human Bronchial Epithelia of Xenografts," *J. Clin. Invest.* 90:2598–2607 (1992).

Engelhardt, J. F. et al., "Direct gene transfer CFTR into human bronchial epithelia of xenografts with E1–deleted adenoviruses," *Nature Genet.* 4:27–34 (1993).

Engelhardt, J. F. et al., "Reconstitution of tracheal grafts with a genetically modified epithelium," *Proc. Natl. Acad. Sci. (USA)* 88:11192–11196 (1991).

Ensinger et al., "Selection and Preliminary Characterization of Temperature–Sensitive Mutants of Type 5 Adenovirus," *J. Virol.* 10:328–339 (1972).

Green, M. et al., "Kinetics of Nucleic Acid and Protein Synthesis in Suspension Cultures," *Virol.* 13:169–176 (1961).

Hall, et al., "The Virus Watch Program: A Continuing Surveillance of Viral Infections in Metropolitan New York Families," *Am. J. Epichemiol.* 94:367 (1971).

Hazinski, T. A. et al., "Localization and Induced Expression of Fusion Genes in the Rat Lung," *Am. J. Respir. Cell. Mol. Biol.* 4:206–209 (1991).

Horwitz, M. S., "Adenoviridae and Their Replication," *Virology*, 2d ed., Raven Press Ltd., pp. 1679–1720 (1990).

Kelsen, "A Technique to Harvest Viable Tracheobronchial Epithelial Cells from Living Human Donors," *Am. J. Respir. Cell Mol, Bio.* 17:66–72 (1992).

Kerem, E. et al., "Prediction of Mortality in Patients with Cystic Fibrosis," *N. Engl. J. Med.* 326:1187–1191 (1992).

Logan, J. et al., "Adenovirus tripartite leader sequence enhances translation of mRNAs late after infection," *Proc. Natl. Acad. Sci. (USA)* 81:3655–3659 (1984).

Plopper, C. G. et al., "Tracheobronchial Epithelium in the Adult Rhesus Monkey: A Quantitative Histochemical and Ultrasturctural Study," *Am. J. Anat.* 184:31–40 (1989).

Randell, S. H. et al., "Properties of Rat Tracheal Epithelial Cells Separated Based on Expression of Cell Surface α–Galactosyl End Groups," *Am. J. Respir. Cell. Mol. Biol.* 4:544–554 (1991).

Rosenfeld, M. A. et al., "Adenovirus–Mediated Transfer of a Recombinant α1–Antitrypsin Gene to the Lung Epithelium in Vivo," *Science* 252:431–434 (1991).

Rosenfeld, M. A. et al., "In Vivo Transfer of the Human Cystic Fibrosis Transmembrane Conductance Regulator Gene to the Airway Epithelium," *Cell* 18:143–155 (1992).

Rutten, A. A. J. J. L. et al., "Effect of cigarette smoke condensate and vitamin A depletion on keratin expression patterns in cultured hamster tracheal epithelium," *Virchows Archiv. B. Cell. Pathol.* 56:111–117 (1988).

Schwachman, "Long–Term Study of One Hundred Five Patients with Cystic Fibrosis," *Am. J. Dis. Child* 96:6–15 (1958).

Sterner, "Adenovirus Infection in Childhood," *Acta Paediatr. Scand. Suppl.* 142–1 (1962).

Stratford–Perricaudet, L. D. et al., "Widespread Long–term Gene Transfer to Mouse Skeletal Muscles and Heart," *J. Clin. Invest.* 90:626–630 (1992).

VanderVliet, P. et al., "Thermolabile DNA Binding Proteins from Cells Infected with a Temperature–Sensitive Mutant of Adenovirus Defective in Viral DNA Synthesis," *J. Virol.* 15:348–354 (1975).

Wilson, D. W. et al., "The Tracheobronchial Epithelium of the Bonnet Monkey (Macacaradiata): A Quantitative Ultrastructural Study," *Am. J. Anat.* 171:24–40 (1984).

Yankaskas, J. R. et al., "Persistence of Abnormal Chloride Ion Permeability in Cystic Fibrosis Nasal Epithelial Cells in Heterologous Culture," *Lancet* 1:954–956 (1985).

Yoshimura, K. et al., "Expression of the human cystic fibrosis transmembrane conductance regulator gene in the mouse lung after in vivo intratracheal plasmid–mediated gene transfer," *Nucleic Acids Res.* 20:3233–3240 (1992).

Collins, Science, vol. 256, 8 May 1992, pp. 774–779.

Spessot et al., Virology, vol. 168 (1989) pp. 378–387.

Y. Yang et al. (1994) Nature Genetics 7:362–369.

ADENOVIRUS VECTORS FOR GENE THERAPY

Work on this invention was supported by the Cystic Fibrosis Foundation and by the United States Government under grants DK42718 and DK39690 awarded by the National Institutes of Health. The Government may have certain rights in the invention.

RELATED APPLICATIONS

This application is a continuation-in-part of U.S. application Ser. No. 07/943,952, entitled "Non-Human Animal Characterized by a Human Airway," filed Sep. 11, 1992, now abandoned and also a continuation-in-part of U.S. application Ser. No. 08/067,296, entitled "Gene Therapy for Cystic Fibrosis," filed on May 25, 1993, now abandoned, which is a divisional of U.S. application Ser. No. 07/584,275, entitled "Gene Therapy Vector for Cystic Fibrosis," filed on Sep. 18, 1990, now U.S. Pat. No. 5,240,846, which is a continuation-in-part of U.S. application Ser. No. 07/401,609, entitled "Cystic Fibrosis Gene," filed on Aug. 31, 1989, now abandoned, which is a continuation-in-part of U.S. application Ser. No. 07/399,945, entitled "Cystic Fibrosis Gene," filed on Aug. 24, 1989, now abandoned, which is a continuation-in-part of U.S. application Ser. No. 07/396,894, entitled "Cystic Fibrosis Gene," filed on Aug. 22, 1989, now abandoned, all of which applications are specifically incorporated by reference herein.

FIELD OF THE INVENTION

The present invention relates generally to adenovirus vectors and to methods for making and using such vectors, particularly to an adenovirus vector containing at least a portion of the E3 region and a deletion of at least a portion of the E1 region, and more particularly to such an adenovirus vector containing an additional deletion or mutation.

BACKGROUND OF THE INVENTION

Adenoviruses are a large family of double-stranded DNA viruses that replicate in the nucleus of the host cell. The viral genes are categorized as either "early" or "late" genes. These temporal categories are based on when the genes are transcribed into mRNA during the virus life cycle. Transcription occurs coordinately and the transition from early to late transcription occurs at approximately 10 hours post-infection, coinciding with DNA replication. As the viral genes are expressed, there is a gradual reduction in host cell RNA, DNA and protein synthesis while the quantity of viral proteins and nucleic acids slowly rises. By about 36 hours post-infection, the host cell disintegrates and the virus is released into the environment.

Adenoviruses are thus ideal candidates for generating vectors useful in gene therapy because the virus uses the host cell's own machinery to synthesize viral RNA, DNA and proteins. Furthermore, the transcription of the adenovirus genes, the organization of the genome and the DNA sequence of the genome have been well defined. Thus, non-viral DNA encoding proteins of interest can be inserted into the adenovirus genome at appropriate locations, and these proteins can be readily expressed in the host cell.

Because adenovirus replication ultimately results in cell death, previous adenovirus vectors were designed to reduce virus replication. Reduced viral replication has been accomplished by deleting or mutating portions of early genes such as the E1a/E1b region, as this region of the genome regulates the expression of various other adenovirus genes required for DNA replication. Berkner, K. L., *Biotechniques* 6:616–629 (1988). Horwitz, M. S., "Virology," 2d ed., Raven Press Ltd., p.1679–1720 (1990).

Although E1a/E1b-deleted adenoviruses exhibit reduced virus replication, these vectors are inefficiently packaged into the viral capsid due to the large genome generated by the additional transgene DNA. The inefficient packaging reduces the titer of the virus stocks by 2–3 logs in comparison to traditional vectors. The low titer of the E1a/E1b-deleted viruses reduces their usefulness, especially for applications to entire organs such as the lung.

Vectors have been constructed with an additional deletion in the E3 region. This deletion increases the amount of non-viral DNA that can be inserted into the vector while maintaining efficient packaging of the recombinant virus. Engelhardt, J. F. et al., *Nature* Genet. 4:27–34 (1993). However, there is speculation that expression of the E3 gene aids virus-infected cells in avoiding the immune response of the host. Therefore, deleting the E3 region is undesirable, as the lack of E3 protein expression increases the chance that the virus infected cells will be rejected by the immune system of the host.

E3-inclusive, E1a/E1b-deleted adenovirus vectors currently exist and have been approved for clinical trial. A major disadvantage of these vectors, however, is again, inefficient packaging because of large genome size that leads to much lower titers than traditional vectors, making them less useful in large scale human applications. With deletions in other regions of the adenovirus genome, the E3 region could be retained and the appropriate viral genome size could be achieved for the production of high titer stocks for clinical use.

A particularly useful application for adenovirus vectors is in the treatment of cystic fibrosis (CF) by gene therapy. Various gene therapy approaches have been considered for cystic fibrosis without sufficient results. One such approach is to selectively reconstitute cystic fibrosis transmembrane regulator (CFTR) gene expression in the surface epithelium using gene transfer substrates delivered directly into the airway. Although transfection of airway epithelial cells has been achieved in vivo with cationic liposomes, efficiencies have been below what is required for therapeutic efficacy. Hazinski, T. A. et al., *Am. J. Respir. Cell. Mol. Biol.* 4:206–209 (1991); Yoshimura, K. et al., *Nucleic Acids Res.* 20:3233–3240 (1992). Likewise, recombinant retroviruses carrying the CFTR gene have been unacceptable because efficient and stable recombinant gene expression can be accomplished in proximal airway with recombinant retroviruses only if the epithelium is undifferentiated and regenerating at the time of exposure to virus, a situation that is difficult to simulate in patients. Engelhardt, J. E. et al., *J. Clin. Invest.* 90:2598–2607 (1992).

The use of recombinant adenoviruses for cystic fibrosis gene therapy is thus particularly attractive especially considering the important advantages of adenovirus vectors, including their natural tropicity to human airway, growth to extremely high titers, and their ability to transfer and express recombinant genes in nondividing cells. Graham, F. L. et al., "Gene Transfer and Expression Protocol," E. J. Murray ed., The Human Press, Inc., Clifton, N.J. 109–128 (1992). Due to these advantages, recombinant adenoviruses have been used to transfer genes for α-1-antitrypsin and CFTR into lungs of cotton rats. Rosenfeld, M. A. et al., *Science* 252:431–434 (1991); Rosenfeld, M. A. et al., *Cell* 68:143–155 (1992).

It would thus be desirable to produce an improved recombinant adenovirus vector. It would also be desirable to produce a recombinant adenovirus vector which has a deletion of at least a portion of the E1 region, retains at least a portion of the E3 region and contains an additional deletion to accommodate a transgene and/or other mutations which result in reduced expression or over-expression of adenoviral protein and/or reduced viral replication. It would further be desirable to produce a recombinant adenovirus vector which has a deletion of at least a portion of the E1 region, retains at least a portion of the E3 region, contains an additional deletion to accommodate a transgene and/or other mutations which result in reduced expression or over-expression of adenoviral protein and/or reduced viral replication, and which contains a transgene of interest, for example, the CFTR gene. In addition, it would be desirable to produce a gene expression system useful for the study and employment of therapeutic approaches.

SUMMARY OF THE INVENTION

The present invention comprises an improved adenovirus vector and methods for making and using such vectors. The vectors are particularly useful in gene transfer and expression. The vectors of the present invention are also useful as a research model to study gene expression and various therapeutic approaches. The adenovirus vectors of the present invention reduce or eliminate viral replication in vivo and viral protein expression, thereby decreasing the immune response of the infected host to the virus and viral protein. By decreasing the host immune response, the persistence of expression of the inserted gene is increased. The adenovirus vectors of the present invention are efficiently packaged to further facilitate the transfer of inserted non-viral genes to host cells. Thus, the vectors of the present invention may be characterized by efficient packaging, reduced virus replication and increased persistence of transgene expression.

In one embodiment of the present invention adenovirus vectors retain at least a portion of the E3 region and carry a deletion of at least a portion of the E1 region, which is upstream from the E3 region, as well as a deletion within adenovirus genes other than E1 and E3 region genes to reduce viral genome size. By up and downstream is meant the location on a nucleotide sequence in the conventional 5' to 3' orientation, wherein upstream is towards the 5' end and downstream is towards the 3' end of the sequence. Deletions in the E3 gene region are presently based on available restriction sites for cloning; however, it will be appreciated that other E3 deletions are also contemplated by the present invention. Deletions in genes other than in the E1 and E3 genes may occur in structural or nonstructural viral genes and can affect the early or late genes, and include, in particular, deletions in the E2a region. These deletions allow for the retention of at least a portion of the E3 region and inclusion of a transgene. The inclusion of a portion of the E3 region increases persistence of transgene expression.

In another embodiment of the present invention, the adenovirus vectors contain at least a portion of the E3 region and a deletion of at least a portion of the E1 region, as well as a mutation which produces temperature-sensitive (ts) virus. The mutation imparting temperature-sensitivity to these vectors can occur in adenovirus genes encoding non-structural proteins or structural proteins, or both. Viral stocks of the vectors are capable of replicating in vitro at permissive temperatures but are incapable or have reduced ability to replicate in vivo at non-permissive temperature, thus increasing transgene expression.

In an additional embodiment of the present invention, the temperature-sensitive adenovirus vectors are replication-defective virus at both permissive and non-permissive temperatures. These vectors contain a mutation in non-structural genes or structural genes, or both, such that the mutant viral proteins are unstable at both permissive and non-permissive temperatures.

In another embodiment of the present invention, the recombinant adenoviruses contain at least a portion of the E3 region and a deletion of at least a portion of the E1 region, as well as mutations in other genes producing viral proteins. These vectors destabilize expression of viral proteins that are expressed or overexpressed in E3-inclusive/E1-deleted vectors, thereby decreasing the immune response of the infected host to the viral protein. Vectors of the present invention which contain at least a portion of the E3 region, carry a deletion of at least a portion of the E1 region and include a deletion within adenovirus genes other than E1 and E3 genes, and/or a mutation which results in increased persistence of transgene expression, reduction in expressed or over-expressed adenoviral protein and/or reduced viral replication, are hereinafter referred to as "second generation" vectors. Second generation vectors are preferably temperature-sensitive to allow for in vitro propagation of virus at 32° C. and defective growth in vivo at 37° C. The vectors of the present invention which contain at least a portion of the E3 region and a deletion of at least a portion of the E1 region are herein referred to as "first generation" vectors.

In a further embodiment of this invention the adenovirus vectors carry a transgene operatively-linked thereto. By "operatively-linked" is meant attached in a manner which allows for transgene transcription, e.g., through the use of sufficient regulatory elements in the vector construct. It will be appreciated that a variety of strategies and the methodology for creating such constructs are well known to those skilled in the art. By "transgene" is meant any gene or gene region that is foreign to the naturally occurring adenovirus. By "gene" is meant any nucleic acid or reverse transcript thereof having a sequence which codes for the polypeptide or protein of interest, including those which function as structural or regulatory elements, or both. This term includes nucleic acids having naturally-occurring sequences, as well as synthetic or any coding sequences which are capable of expression. Although any number of transgenes can be employed in the practice of the present invention, preferred transgenes include those useful for gene therapy, such as e.g. the gene for cystic fibrosis transmembrane regulator (CFTR). Thus, in an additional embodiment of this invention the adenovirus vectors are used to treat non-inherited and inherited genetic and epigenetic diseases or disorders.

DETAILED DESCRIPTION OF THE PREFERRED EMBODIMENTS

Figure 1A:
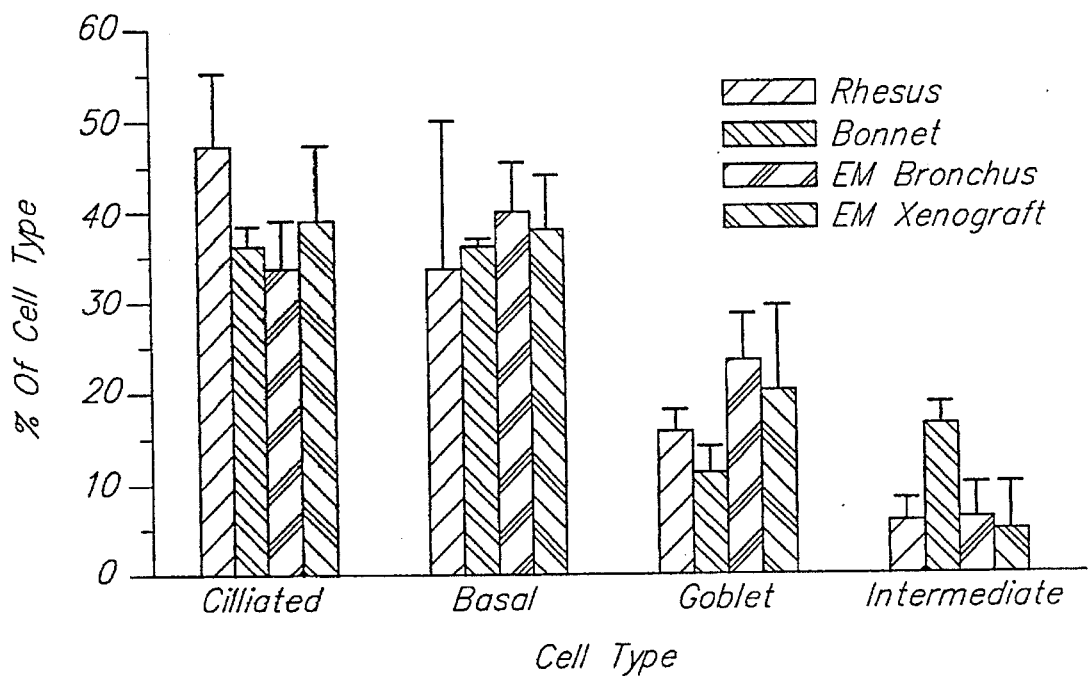
FIGS. 1 (A–B) are bar graphs showing the distribution of cell types in several proximal airway samples.

Construction of the adenovirus vectors of the present invention is performed by standard tranfection techniques for E1a/E1b-deleted adenovirus vectors using the complementation human embryonic kidney (HEK) 293 cell line, a human kidney cell line containing a functional E1a gene which provides a transacting E1a protein, allowing efficient replication of the adenovirus vectors. Three general techniques are used in generating recombinant stocks: 1) overlapping fragments of the viral genome, one containing the mutant gene and a second that contains the remainder of the wild type genome, are cotransfected using standard $CaPO_4$ transfection techniques in 293 cells followed by viral plaqueing with agar overlay; 2) ligation of various regions of the viral genome containing mutated regions and nonmutated regions followed by standard $CaPO_4$ transfection techniques; and 3) cotransfection of mutant strain viral genomic DNA and plasmid sequences containing the transgene and partial viral sequences for homologous recombination.

Mutant viral stocks which contain no transgene are obtained from previously published work or generated and selected using standard recombinant molecular cloning techniques known and practiced by those skilled in the art. Mutant viral stocks obtained from previously published work are combined with other deletions necessary for the generation of recombinant virus by the above-stated techniques. Deletions, insertions, and other mutations are generated using standard techniques and selection schemes. As one of skill in the art will recognize, "mutation" refers to any alteration of the DNA including, but not limited to, deletions, insertions, and missense and nonsense mutations. One skilled in the art will also appreciate which type of mutation is being referred to from the context in which it is used.

The human bronchial xenograft model of human airway as described in the parent U.S. application Ser. No. 943,952, entitled "Non-Human Animal Characterized by a Human Airway", filed Sep. 11, 1992, has also been used to study the adenovirus vectors of the present invention. The xenografts develop into a fully differentiated pseudostratified epithelium that is indistinguishable from that found in the endogenous human airway. This model therefore provides a unique opportunity in which to assess the ability of adenovirus vectors to replicate in human airway epithelium. To test for increased persistence of transgenes, two additional animal models are used, the ferret and non-human primates.

As further discussed below, immunocytochemical detection of three adenovirus proteins (hexon, fiber and the DBP E2a gene product) within the human bronchial xenograft model after infection with recombinant adenoviruses showed that the two late viral proteins hexon and fiber were not expressed at detectable levels, while the 72kd DPB E2a gene product was expressed at higher than wild type level (i.e. higher than xenografts infected with wild type adenovirus type 5). These data are the foundation for targeting specific genes (i.e. the 72kd DPB) for mutation or deletion which are known to be over-expressed in vivo.

The adenovirus vectors of the present invention are useful for gene therapy to treat various non-inherited or inherited genetic or epigenetic diseases or disorders such as adult respiratory distress syndrome (ARDS), cystic fibrosis and asthma. The adenovirus vectors of the present invention are also useful as a research model to study therapeutic approaches including gene therapy. As one of skill in the art will realize, each adenovirus vector of the present invention may be constructed having any transgene useful in the treatment of various diseases operatively-linked thereto.

When used as a therapeutic, a therapeutically effective dosage of the vectors of the present invention will be administered for a therapeutically effective duration. By "therapeutically effective amount" and "therapeutically effective duration" is meant an amount and duration sufficient to achieve a selected desired result in accordance with the present invention without undue adverse or with medically acceptable physiological effects, which can be determined by those skilled in the medical arts. A therapeutically effective human dosage of the vectors of the present invention is believed to be in the range of from about 20 to about 50 ml of saline solution containing concentrations of from about $1\times10^7$ to $1\times10^{10}$ pfu/ml vector of the present invention. A preferred human dosage is about 20 ml saline solution at the above concentrations.

It will be appreciated that formulations suitable for administration of the adenovirus vectors of the present invention include aqueous and non-aqueous isotonic sterile injection solutions and aqueous and non-aqueous sterile suspensions. In the case of CFTR gene delivery, preferred solutions for bronchial instillation are sterile saline solutions containing in the range of from about $1\times10^7$ to $1\times10^{10}$ pfu/ml, more particularly, in the range of from about $1\times10^8$ to $1\times10^9$ pfu/ml of the viral vector of the present invention. It will also be appreciated that administration of the adenovirus vectors of the present invention will be by procedures well established in the pharmaceutical arts, e.g. by direct delivery to the target organ, tissue or site, intranasally, intravenously, intramuscularly, subcutaneously, intradermally and through oral administration, either alone or in combination.

SPECIFIC EXAMPLE 1—Transgene Expression

In accordance with the principles of the present invention, exposure of the xenograft to recombinant adenoviruses results in transgene expression (i.e. lacZ and human CFTR) in a large number of surface epithelial cells (i.e. 5–20% with concentrated virus) and the expression is stable and not associated with pathology. Recombinant gene expression was detected in all cell types of the surface epithelium except basal cells. A possible explanation for the low level of expression in basal cells may simply relate to the level of abundance of adenoviral receptors on this cell type.

Immunocytochemical techniques were used to detect adenoviral proteins in cells of the xenograft that express the recombinant gene. Horwitz, M. S., "Adenoviridae and their Replication In: Virology," B. N. Fields, D. M. Knipe et al., eds., 2d ed., Raven Press, Ltd., N.Y. 1679–1721 (1990). Expression of several adenoviral genes was evaluated including 1) the E2a gene, expressed in the early and late phase of the adenoviral life cycle, which encodes a 72 kd DNA binding protein; and 2) the L3 and L5 transcripts, which are formed from the single late transcriptional unit, and encode the structural proteins hexon and fiber, respectively. The program of adenoviral protein expression in cells of the human xenograft differed substantially between wild type Ad5 and the E1-deleted recombinants. Cells infected with wild type Ad5 expressed high levels of the structural proteins hexon and fiber and lower levels of the E2a gene product indicating they are capable of supporting the full life cycle of Ad5. Cells harboring E1-deleted Ad5 expressed little if any of the structural proteins hexon and fiber; however, the E2a gene was expressed at very high levels in a subset of transgene containing cells. This suggests that the recombinant virus is prevented from transitioning into the late phase of transcription in the absence of E1a and E1b. However, a subset of cells is capable of activating transcription from the E2a promoter independent of E1a and E1b. The consequences of E2a expression in human airway epithelial cells are presently unknown. Non-human primates in which both the lacZ and CFTR adenoviruses were administered into the airway express high levels of DBP in a subset of lacZ expressing cells, but do not generate an immune response to this protein product of the E2a gene.

Xenografts were sequentially irrigated for a 3-week period after exposure to adenovirus, and the effluents were analyzed for wild type and recombinant virus. Wild type virus was never detected in the effluents and the concentration of recombinant virus dropped precipitously during the initial week and stabilized at low but detectable concentrations for the second phase of the experiment, which lasted up to 24 days. It is possible that the virus recovered in the effluents represents residual virus from the initial infusion. An alternative explanation is that the genetically reconstituted xenografts support low levels of virus production. Replication of E1a-deleted viruses has been described in vitro. Horwitz, M. S., supra. One potential mechanism to account for the presence of virus in effluents is that an occasional cell in the xenograft overcomes the block in adenoviral replication, leading to its death and the production of more recombinant virus. The life cycle of group C viruses such as Ad2 and Ad5 in the context of full E1 expression is extremely efficient and results in the production of 10,000 virions per infected cell. Green, M. et al., Virol. 13:169–176 (1961). Progression of the full Ad lytic cycle in only 1–2 cells per xenograft per week could account for the steady state level of recombinant virus detected in the effluents (i.e. 100 to 10,000 viruses/irrigation). Another potential mechanism is that the virus replicates at low levels in a large population of infected cells and low quantities of virus are released when the cells undergo normal turnover. The inability to detect wild type levels of structural proteins in a sample of 1500 infected cells is consistent with either mechanism.

An important outcome of this example as it relates to the utility of recombinant adenoviruses for gene therapy is the stability of recombinant gene expression that was achieved in the human xenograft. Detailed characterization of the molecular state of the viral genome in xenografts is difficult because of the limited amount of material available for analysis. DNA analysis of cultured human epithelial cells infected with the lacZ and CFTR viruses indicated that the adenoviral genome persists primarily as nonintegrated DNA (data not shown). Additionally, episomal persistence of recombinant Ad.RSVβgal has been shown in newborn mice. Stratford-Perricaudet, L. D. et al., J. Clin. Invest. 90:626–630 (1992). This finding suggests that the persistence achieved in the xenograft may be due to extrachromosomal viral genomes that are stabilized or replicating in the absence of virion formation. An alternative explanation is that the apparent persistence of recombinant gene expression is due to ongoing production of virus and reinfection. This possibility is unlikely, however, because the levels of virus recovered in the effluents is 5 to 6 logs lower than that necessary to sustain the observed level of stable genetic reconstitution.

Preparation of recombinant adenovirus. Four different replication-defective adenoviruses based on Ad5 were used, including Ad. E1Δ, Ad. CMVlacZ, Ad. CB-CFTR, and Ad.RSVβgal. Ad.E1Δ had been deleted of E1a sequences spanning 1.0 to 9.2 map units (mu) and E3 sequences spanning 78.4 to 86 mu. A minigene containing the cytomegalovirus (CMV) promoter, cytoplasmic lacZ gene, and SV40 poly A was introduced at the site of the E1 deletion of Ad.E1Δ to make Ad. CMVlacZ. The structure of Ad.RSVβgal has been described previously. Stratford-Perricaudet, L. D. et al., J. Clin. Invest. 90:626–630 (1992). In this virus, E1 sequences from 1.3 to 9.4 mu have been deleted and replaced with a minigene containing the Rous sarcoma virus long terminal repeat (RSV LTR), lacZ gene with nuclear localization sequences, and SV40 early region polyadenylation signal; in addition, E3 sequences spanning to 78.5 to 84.7 mu have been deleted. Ad. CB-CFTR is a derivative of Ad.E1Δ in which the following minigene has been inserted into the E1a deletion site: CMV enhancer, β-actin promoter, human CFTR cDNA and SV40 poly A.

Stock of recombinant viruses were prepared as follows. Cultures of 293 cells (30×150 mm plates) grown in DMEM containing 10% fetal calf serum (FCS), 100 U/ml penicillin, and 100 μg/ml streptomycin were infected at 80% confluency at a MOI of 5 pfu per cell. Cells were harvested by centrifugation 30 hr at post-infection. The pellets were resuspended in a final volume of 18 ml of 10 mM Tris pH 8.0 and subjected to three rounds of freeze-thaw, followed by separation of cell debris by centrifugation at 1500× g for 20 min. Crude viral supernatants were layered onto a CsCl step gradient and centrifuged for 2 hr at 50,000×g. The intact viral particles were subjected to a second round of CsCl banding such that the final CsCl purified adenovirus contained $3-6\times 10^{13}$ viral particles (as measured by OD at 260 nm) in 500–700 μl. Concentrated viral stocks were desalted by gel filtration through Sephadex G50 in Ham's F12 medium to yield a final purified stock of $1-2\times 10^{13}$ viral particles/ml. Viral titers as measured by plaque formation on 293 cells yielded stocks ranging from $0.2-2\times 10^{12}$ pfu/ml. Viral stocks were used for infusion into xenografts immediately after completion of the purification. All stocks were evaluated for the presence of replication competent adenovirus by infection at a MOI of 100 onto HeLa cells and passaging the cells for 30 days. Presence of replication-competent virus in the original stock would manifest itself as the development of cytopathic effects (CPE) in the HeLa cells. None of the stocks used in these experiments yielded such effects.

Generation of human bronchial xenografts. Primary human bronchial epithelial cells were harvested from the mainstem bronchi of lungs (at least three samples for each vector analyzed) destined for transplantation using modifications of a previously described protocol. Yankaskas, J. R. et al., *Lancet* 1:954–958 (1985). Dissected airways were rinsed with MEM containing 50 U/ml penicillin, 50 μg/ml streptomycin, 40 μg/ml tobramycin, 50 μg/ml ceftazidine, 2.5 μg/ml amphotericin B, 10 μg/ml DNAse, and 0.5 mg/ml DTT for 4–12 hr at 4° C. Tissue was then placed in the same media supplemented with 0.1% protease-14 and incubated for an additional 30–34 hr at 4° C. Following the addition of FCS to a final concentration of 10%, the cells were harvested by agitation and blunt scraping. Cells were pelleted and washed twice in Ham's F12 containing 10% FCS and plated at $2\times10^6$ cells/100 mm dish in Ham's F12 containing 1 μM hydrocortisone, 10 μg/ml insulin, 30 Nm thyroxine, 5 μg/ml transferrin, 25 ng/ml epidermal growth factor, 3.75 μg/ml endothelial cell growth supplement, 10 ng/ml cholera toxin, 50 U/ml penicillin, 50 μg/ml streptomycin, 40 μg/ml tobramycin, 50 μg/ml ceftazidine, and 2.5 μg/ml amphotericin B. The medium was replaced after 36 hr and changed every 24 hr thereafter. On the fourth day, cells were harvested by treatment with 0.1% trypsin followed by the addition of 10% FCS/Ham's F12 and resuspended at a concentration of $1\times10^6$ cells per 25 μl in hormonally defined medium in preparation for seeding.

Open-ended grafts were generated from rat tracheas removed from 200 to 250 gm male Fisher 344 rats and subjected to three rounds of freeze-thaw as previously described. Engelhardt, J. F. et al., *Proc. Natl. Acad. Sci. (USA)* 88:11192–11196 (1991). Cells ($1\times10^6$) were injected into the lumen of denuded rat tracheas followed by ligation of the tracheal ends to flexible plastic tubing. These seeded xenografts were transplanted subcutaneously into the flanks of nu/nu mice such that the ends of the tubing exited through the back of the neck. Grafts were allowed to regenerate for three to four weeks before infusion of adenovirus. Stocks of adenoviruses in Ham's F12 (1 ml) were infused into the xenografts over the course of 1 hr and excess fluid was subsequently removed from the lumen by expulsion with air.

Electron microscopic and morphometric analysis of xenografts. Xenografts were excised and fixed as described. Engelhardt, J. F. et al., *Proc. Natl. Acad. Sci. (USA)* 88:11192–11196 (1991). Following fixation, the tissue was washed repeatedly in 0.1M cacodylate, postfixed in 1% osmium tetroxide, dehydrated in alcohol, and embedded in epoxy resins. Sections were stained with uranyl acetate and lead citrate before being viewed and photographed in a Philips CM10 electron microscope.

Morphometric analysis of cell types contained within a donor bronchus and three xenografts generated from this tissue were performed to assess the extent of epithelial reconstitution within this xenograft model. Cells were categorized based on morphologic criteria into four groups: ciliated cells by possessing apically localized cilia, goblet cells by the presence of electron lucent secretory granules, intermediate cells by no luminal contact with cytoplasm extending at least one third the height of the epithelium and not fulfilling the criteria of basal cells, and basal cells by the presence of tonofilaments and a high nuclear to cytoplasmic ratio with the majority of cytoplasm residing on the basal lamina. At lease 30 independent fields from 5 blocks were analyzed from donor bronchus to give a total of 1500 cells. Each of three independently generated xenografts was embedded into four blocks and one complete cross-section of each of these blocks was analyzed giving a total of 12 independent regions of the xenografts. In total, 3000 cells were analyzed from three xenografts.

Cytochemical and immunocytochemical analysis of xenografts for β-galactosidase, CFTR, cytokeratins, and adenoviral proteins. Cytochemical localization and characterization of grafts for β-galactosidase activity by light microscopy was performed with glutaraldehyde-fixed tissue stained in Xgal for 4 hr followed by embedding in GMA as described previously. Engelhardt, J. F. et al., *Proc. Natl. Acad. Sci. (USA)* 88:11192–11196 (1991). The abundance of lacZ transgene-expressing cells was quantitated by counting the percentage of Xgal positive cells from GMA sections within a group of 16,000 cells. The distribution of the various cell types (ciliated, basal, goblet, and intermediate cells) within the xenograft epithelium was based on averages from 3000 cells counted from 5 independent regions of a representative criteria. Identification of the various cell types was based on the following morphologic criteria: ciliated cell—the presence of cilia; basal cell—cuboidal appearing cell of high nuclear to cytoplasmic ration with nuclei in the lowest layer of epithelium, direct contact with the basal lamina, and no luminal contact; goblet cells—the presence of mucous granules as visualized under Nomarski optics; and intermediate cells—cells in contact with the basal lamina but with cytoplasm extending upward into the epithelium but not contacting the luminal surface. The relative infectivity of ciliated cells, basal cells, goblet cells, and intermediate cells was quantitated by counting 1000 gal positive cells from GMA sections of grafts infected with $1\times10^{12}$ pfu/ml of virus. Distribution of cells expressing lacZ was also evaluated by immunocytochemical co-localization with a cell specific marker to basal cells, (cytokeratin 14), and one to differentiated columnar cells (cytokeratin 18). Randell, S. H. et al., *Am. J. Respir. Cell. Mol. Biol.* 4:544–554 (1991). Rutten, A. A. J. J. L. et al., *Virchows Archiv. B. Cell. Pathol.* 56:111–117 (1988).

Immunocytochemical co-localization of β-galactosidase, cytokeratin 14, and cytokeratin 18 proteins was performed as follows. Sections of fresh frozen tissue (6 μm) were postfixed in methanol for 10 min, air dried, and blocked in PBS containing 20% donkey serum (DS) for 30 min. Sections were then incubated sequentially in undiluted hybridoma supernatant to cytokeratin 14 (gift from Dr. Ramaekers, RCK107) for 90 min followed by three 8 min washes in 1.5% DS/PBS and incubation in 5 μg/ml of AMCA-anti-mouse (Fab')$_2$ secondary antibody for 30 min. After washing, these sections were incubated in PBS/1.5% DS containing 66 μg/ml rabbit anti-β-galactosidase (5'-3' inc.) and FITC-cytokeratin 18 (Sigma) at a dilution of 1:400 for 90 min. Sections were washed and incubated in 5 μg/ml donkey anti-rabbit Texas Red for 30 min. Following three washes in 1.5% DS/PBS, sections were mounted in Citifluor antifadent and visualized on a Microphet-FXA Nikon fluorescent microscope. Cell types expressing lacZ were quantitated from sections stained for β-galactosidase, cytokeratin 14 and cytokeratin 18; 1000 total lacZ positive cells were counted. Localization of CFTR was performed using an antibody to the 13 C-terminal amino acids of human CFTR (α1468) as previously described. Engelhardt, J. F. et al., *Nature Genet.* 2:240–248 (1992).

Immunocytochemical co-localization of β-galactosidase with the adenoviral proteins DBP, fiber, and hexon was performed as with cytokeratin co-localization using the following modifications. Sections were incubated sequentially with 66 μg/ml anti-β-galactosidase (5'→3', inc), a 1/10 dilution of hybridoma supernatant to Ad5 DBP, 5 μg/ml of both donkey anti-rabbit-AMCA and donkey anti-mouse Texas Red, followed by a 1/10 dilution of mouse anti-Ad3 fiber-FITC (Ab805F, Chemicon, Inc.). Western analysis of purified adenovirus type 5 indicated that Ab805F recognizes a 62 kd protein consistent with fiber protein. Additional sections were treated similarly by replacing the Ab805F with a goat anti-Ad5-FITC antibody to the hexon protein of adenovirus type 5 (Ab1059F, Chemicon, Inc.).

In situ detection of CFTR mRNA. Frozen sections (6 μm) were mounted on gelatin poly(L-lysine)-coated slides and fixed with 4% paraformaldehyde in phosphate buffered saline (PBS) for in situ hybridization analysis as previously described using $^{35}$S RNA probes to the R-domain (1899bp to 2623bp) of human CFTR. Engelhardt, J. F. et al., *Nature Genet.* 2:240–248 (1992). As a control, samples were also assessed for hybridization to an antisense CFTR probe. In addition, samples were hybridized to the sense or antisense CFTR probe both with and without pretreatment with RNAse.

Recovery of adenoviruses from xenografts. To assess the ability of recombinant adenovirus to replicate within human xenograft epithelium, effluent fractions were collected at timed intervals following infection. Xenografts were infected with freshly prepared stocks of virus ($1\times10^{11}, 10^{10}$, and $10^9$ pfu/ml) for 16 hr followed by washing with two 1 ml aliquots of buffered saline. The second aliquot was designated fraction 1. At 3½-day intervals additional fraction were collected by irrigating the lumen of the xenograft with 1 ml aliquots of buffered saline. All fractions were frozen on dry ice and stored at –80° C. Upon completion of the experiment the fractions were thawed and evaluated for recombinant virus by a limiting dilution plaque assay on 293 cells. Plaques were stained for β-galactosidase by overlaying 1 ml of Xgal solution onto the agar at day 9 following infection. All plaques showed the presence of blue Xgal precipitate.

Characterization of the surface epithelium reconstituted in xenografts. Xenografts seeded with $1\times10^6$ freshly isolated human bronchial epithelial cells gave rise to fully differentiated epithelia within 3 weeks after implantation into nu/nu mice. Transmission electron microscopy of epithelium from a xenograft seeded with human bronchial epithelial cells harvested at 42 days, demonstrated that the general organization of epithelia in xenografts is similar to that found in native airway. Electron micrographs were analyzed morphometrically to evaluate the distribution of cell types found in proximal surface epithelia of these tissues. A summary of these data are included in FIG. 1A. The distribution of cell types found in xenografts and bronchial tissues closely resembles that previously described for the proximal airway of primates which is also shown in FIG. 1A. Plopper, C. G. et al., *Am. J. Anat.* 184:31–40 (1989); Wilson, D. W. et al., *Am. J. Anat.* 171:25–40 (1984). Furthermore, there were no differences in the abundance of ciliated cells, goblet cells, basal cells and intermediate cells noted between the xenografts and bronchial tissue from which the xenografts were derived (see FIG. 1A for statistical analysis). This finding confirms the validity of the xenograft model for studying proximal human airway.

Adenoviral-mediated gene transfer in human bronchial epithelia. A variety of recombinant adenoviruses based on Ad5 were used. E1 and E3 sequences were deleted from each virus. Some of the recombinants contained a minigene in place of E1. Viruses used include: Ad.E1Δ, the precursor recombinant virus in which E1 and E3 have been deleted, without addition of any other sequences; Ad.RSVβgal, containing nuclear targeted lacZ expressed from a *Rous Sarcoma* virus (RSV) LTR; Ad.CMVlacZ, containing cytoplasmic lacZ expressed from the cytomegalovirus (CMV) promoter; and Ad.CB-CFTR, containing human CFTR expressed from the CMV enhancer and β-actin promoter.

Xenografts were infected with purified stocks of Ad. RSVβgal ($1\times10^{12}, 10^9$, and $10^8$ pfu/ml) or Ad.E1Δ ($1\times10^{12}$ pfu/ml) for one hour after which the virus was expelled. Grafts were harvested, fixed, stained in Xgal and visualized en face through a dissecting microscope in order to assess the overall efficiency of infection. All xenografts were harvested at 3 days post-infection except for that infected with $1\times10^9$ pfu/ml, which was harvested 21 days after infusion of virus. Xenografts infected with Ad.E1Δ demonstrated no Xgal positive cells, while large areas of lacZ expression were demonstrated in grafts exposed to Ad.RSVβgal ($1\times10^{12}$ pfu/ml) and harvested 3 days later. Morphometric analysis of GMA sections of this xenograft indicated gene expression in 11±6.3% of the epithelial cells. Similarly high levels of infection were obtained with viral stocks diluted 10 to 100-fold; infection of 12 xenografts generated from 4 independent tissue samples with $1\times10^{10}$ to $10^{11}$ pfu/ml of Ad.RSVβgal resulted in lacZ expression in 5–20% of the cells. The inability to achieve an increment in gene transfer at titers of virus greater than $1\times10^{10}$ pfu/ml suggests that saturation of the adenoviral receptor has been achieved. Xenografts infected with Ad.RSVβgal at $1\times10^9$ and $10^8$ pfu/ml and examined 3 days later demonstrated gene expression in 1.9±0.2% and <0.1% of the total cells of the epithelium, respectively. To determine if lacZ expression is stable within the bronchial epithelium, xenografts were also harvested 21 days following infection with $1\times10^9$ pfu/ml Ad.RSVβgal adenovirus. No changes in the percentage of Xgal positive cells were seen between 3 days and 21 days post-infection. Transgene expression is not diminished in xenografts harvested up to 5 weeks after infection.

Figure 1B:
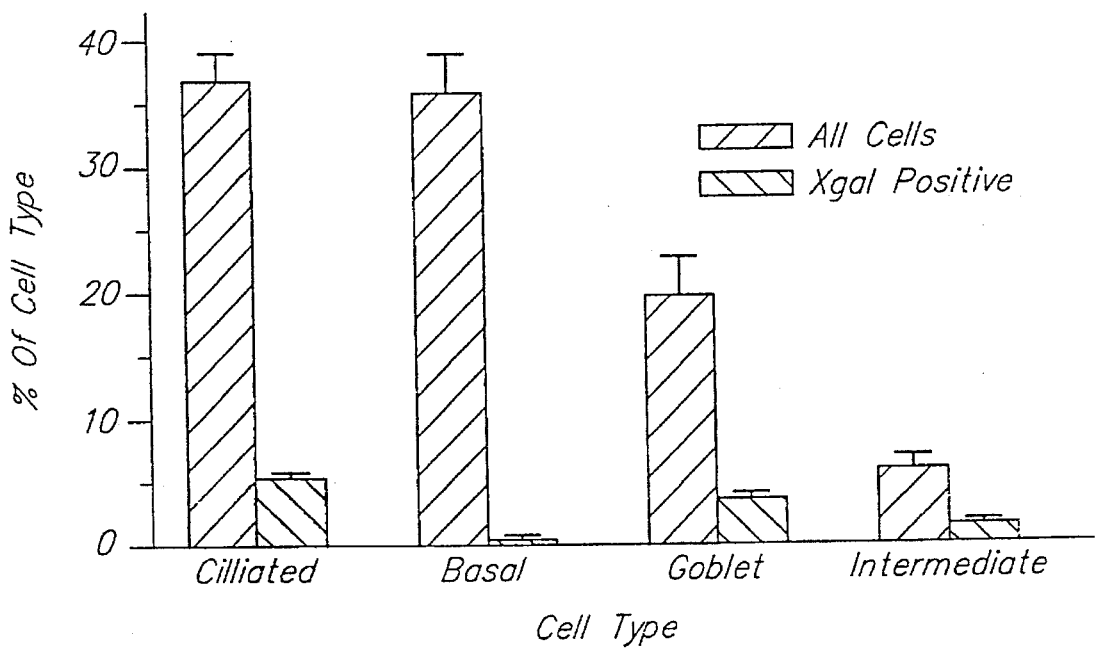

A series of analyses were performed to determine the distribution of transgene expression in the xenografts. Xgal-stained sections of xenografts infected with $1\times10^{12}$ pfu/ml of Ad.RSVβgal were analyzed by light microscopy to determine the percentage of each cell type that expressed the transgene. These results are summarized in FIG. 1B. The distribution of all cell types in the xenograft determined by light microscopy was identical to that established using ultrastructural criteria. The proportion of cells containing Xgal precipitate paralleled the distribution of cell types in the graft with the exception that very few basal cells expressed the transgene. The relative absence of lacZ expression in basal cells was demonstrated in grafts infected with either Ad.RSVβgal or Ad. CMVlacZ, suggesting that variation of the viral promoters driving transgene expression is not the cause for the exclusion of β-galactosidase activity found in basal cells.

Diffusion of Xgal precipitate made the quantification of cell types within large, highly expressing clusters difficult. A more precise definition of the cell types expressing the transgene was achieved by performing immunocytochemistry with antibodies to the reporter gene product β-galactosidase and to one specific for either basal cells (cytokeratin 14) or differentiated columnar cells (cytokeratin 18). Frozen sections (6μm) from xenografts infected with $1\times10^{11}$ pfu/ml Ad. CMVlacZ and harvested 3 days post-infection were analyzed by triple immunofluorescence (Nomarski) with antibodies to: β-galactosidase (conjugated to Texas Red); cytokeratin 14 (conjugated to AMCA); and cytokeratin 18 (conjugated to FITC). LacZ co-localized with the differentiated cell marker cytokeratin 18 in >99.9% transgene expressing cells (N=1500 cells counted) from both Ad.CMVlacZ and Ad.RSVβgal infected grafts, thereby confirming the observations made from Xgal stained grafts.

Additional experiments were performed with recombinant adenoviruses expressing human CFTR to establish the validity of this model for developing gene therapies for cystic fibrosis. Frozen sections (6 μm) from xenografts infected with either 1×10¹¹ pfu/ml of Ad.CB-CFTR or Ad.CMVlacZ and harvested 3 days post-infection were analyzed by in situ hybridization using a human CFTR R-domain probe, and by immunocytochemistry for CFTR protein using a polyclonal CFTR antibody. Engelhardt, J. F. et al., *Nature Genet.* 2:240–248 (1992). Hybridization above background was detected with the antisense CFTR probe in approximately 2–10% of cells in Ad.CB-CFTR infected grafts. A similar proportion of cells in these grafts demonstrated over-expression of CFTR protein based on immunocytochemistry with a CFTR specific antibody. Ad. CMVlacZ infected xenografts failed to demonstrate hybridization to the CFTR probe or binding to the CFTR antibody that was above endogenous levels. Over-expression of CFTR protein in Ad.CB-CFTR infected grafts was detected in all differentiated cell types including ciliated cells, goblet cells, and intermediate cells. The recombinant protein localized to the apical surface in most of the ciliated and goblet cells and to the cytosol of intermediate cells. Expression of recombinant CFTR protein was detected in grafts for at least 5 weeks after infection.

Expression of adenoviral proteins in epithelial cells of genetically reconstituted xenografts. Immunocytochemical techniques were used to analyze xenografts for expression of adenoviral proteins. Antibodies that recognize hexon, fiber, and the 72 kd E2a gene product, i.e. DNA binding protein (DBP), were used to detect adenoviral protein expression in xenografts infected with Ad. CMVlacZ, Ad.RSVβgal, or wild type Ad5. Frozen sections (6 βm) of xenografts infected with 1×10¹¹ pfu/ml Ad. CMVlacZ and harvested 3 days post-infection were analyzed by triple immunofluorescence (Nomarski) with antibodies to β-galactosidase (conjugated to AMCA); DBP (conjugated to Texas Red); and fiber (conjugated to FITC). Xenografts infected with wild type Ad5, harvested 20 hr post-infection and analyzed by double immunofluorescence (Nomarski) with antibodies revealed a subpopulation of cells that expressed high levels of hexon and fiber protein. Double immunofluorescence studies indicated that cells expressing the late gene products hexon and fiber also expressed low levels of the gene product DBP, which is expressed in the early phase of adenovirus infection. Similar analyses of xenografts infected with 1×10¹⁰, 1×10¹¹ and 10¹² pfu/ml of Ad.RSVβgal or Ad.CMVlacZ failed to demonstrate detectable levels of either fiber or hexon proteins despite substantial levels of β-galactosidase expression. However, with longer incubation times and higher concentrations of primary antibody low levels of fiber expression could be seen in nuclei of a few lacZ expressing cells. In contrast, high levels of DBP were found in 3–5% of β-galactosidase positive cells with an occasional cell expressing DBP in the absence of detectable β-galactosidase. Cells expressing DBP tended to express lower levels of β-galactosidase and were predominantly found in clusters. The percentage of DBP expressing β-galactosidase positive cells was the same for MOI's of 1×10¹⁰, 10¹⁰ and 10¹² pfu/ml Recovery of adenovirus from xenografts. Xenografts were subjected to sequential irrigations for a period of up to 24 days after infection. Effluents (1 ml) were collected at 3½-day intervals from xenografts infected with Ad. CMV-lacZ and were titered by Xgal-stained pfu assay on 293 cells. All plaques generated on 293 cells contained β-galactosidase as was evident by the formation of a blue precipitate. Recovered virus was plotted on a log scale versus the time after infusion of virus, measured in days. FIG. 2(A–E) presents representative experiments. The concentration of virus in the effluents dropped precipitously during the initial week following infection in all grafts except that presented in FIG. 2B, in which virus transiently increased before the exponential decline. The amount of virus recovered in the effluents stabilized at low but detectable levels during the remaining period of observation (days 14 to 24) in most but not all of the grafts.

Figure 2A:
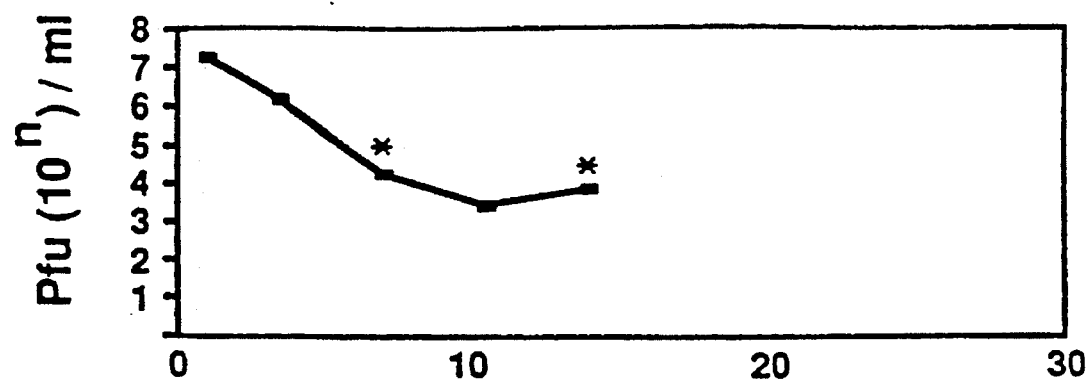
FIGS. 2(A–E) are graphs showing the recovery of recombinant virus in xenograft effluents.
Figure 2B:
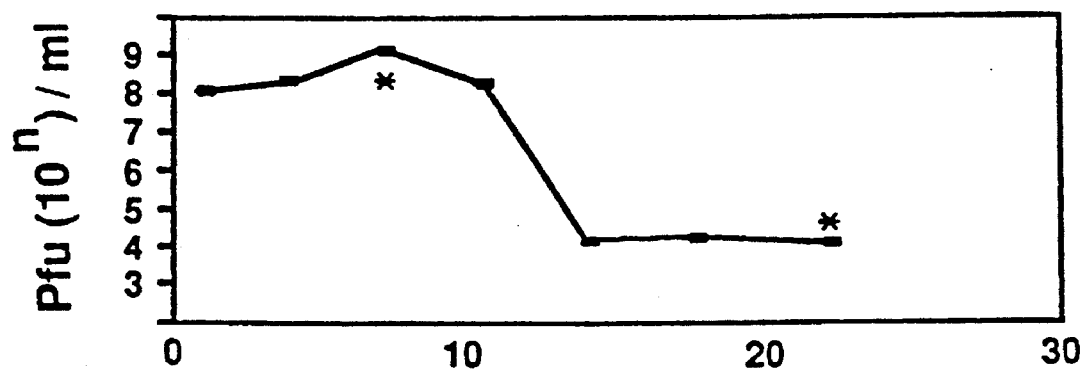
Figure 2C:
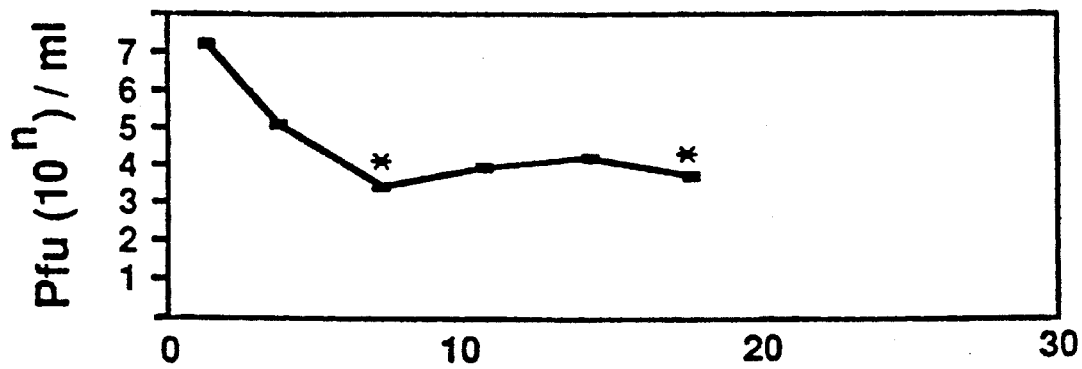
Figure 2D:
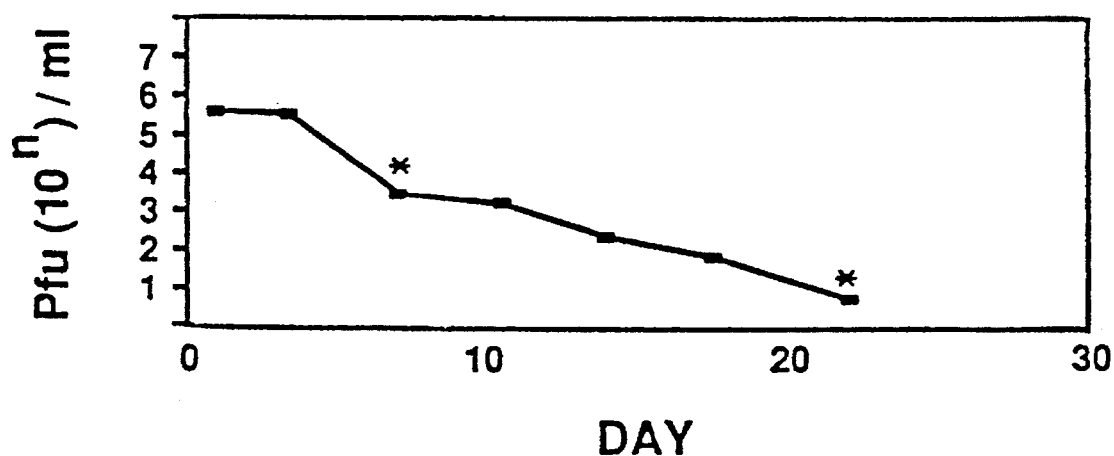
Figure 2E:
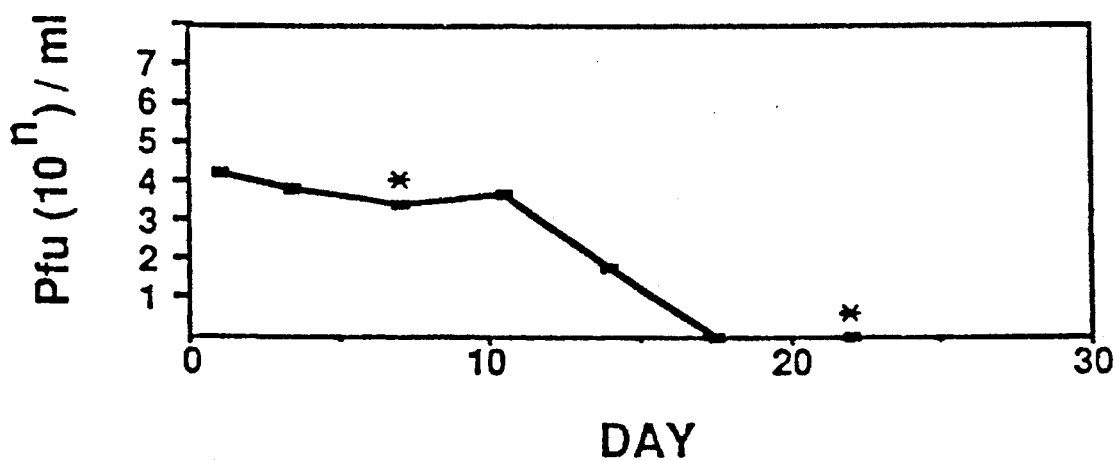

Following the completion of the experiment, the xenografts were harvested, Xgal-stained and evaluated for percentage genetic reconstitution in the surface epithelial cells. The quantity of virus recovered in effluents at the end of the experiment varied substantially between grafts and was proportional to the percentage of the epithelium that expresses the transgene: in FIG. 2(A–E), panels A–C, 5–20% lacZ positive cells; panel D, 1% lacZ positive cells; and panel E, less than 0.01% lacZ positive cells. The highest concentration of virus was detected in effluents from the xenograft with the greatest level of genetic reconstitution (FIG. 2A) whereas the graft that produced effluents with no detectable virus at 24 days was found to have very little transgene expression in its epithelium (FIG. 2E). All viruses recovered in the effluents were found to express lacZ, indicating that the xenografts were not grossly shedding wild type adenovirus.

To further address the possibility of wild type adenoviral contamination in the tissue samples or recombinant stocks, 100 µl of selected 1 ml effluents were used to infect 80% confluent layers of HeLa cells. In FIG. 2, asterisks mark effluents that were assayed for wild type adenovirus by the ability to cause cytopathic effects (CPE) on HeLa cells. Following infection, the media was changed every 48 hr for the first 4 days and every day for the following 17 days. No evidence of CPE was seen with any of the effluents. Finally, polymerase chain reaction (PCR) analysis of effluents failed to detect E1a sequences at a sensitivity of 100 molecules per ml effluent.

SPECIFIC EXAMPLE 2—Temperature-sensitive Vectors

Figure 3:
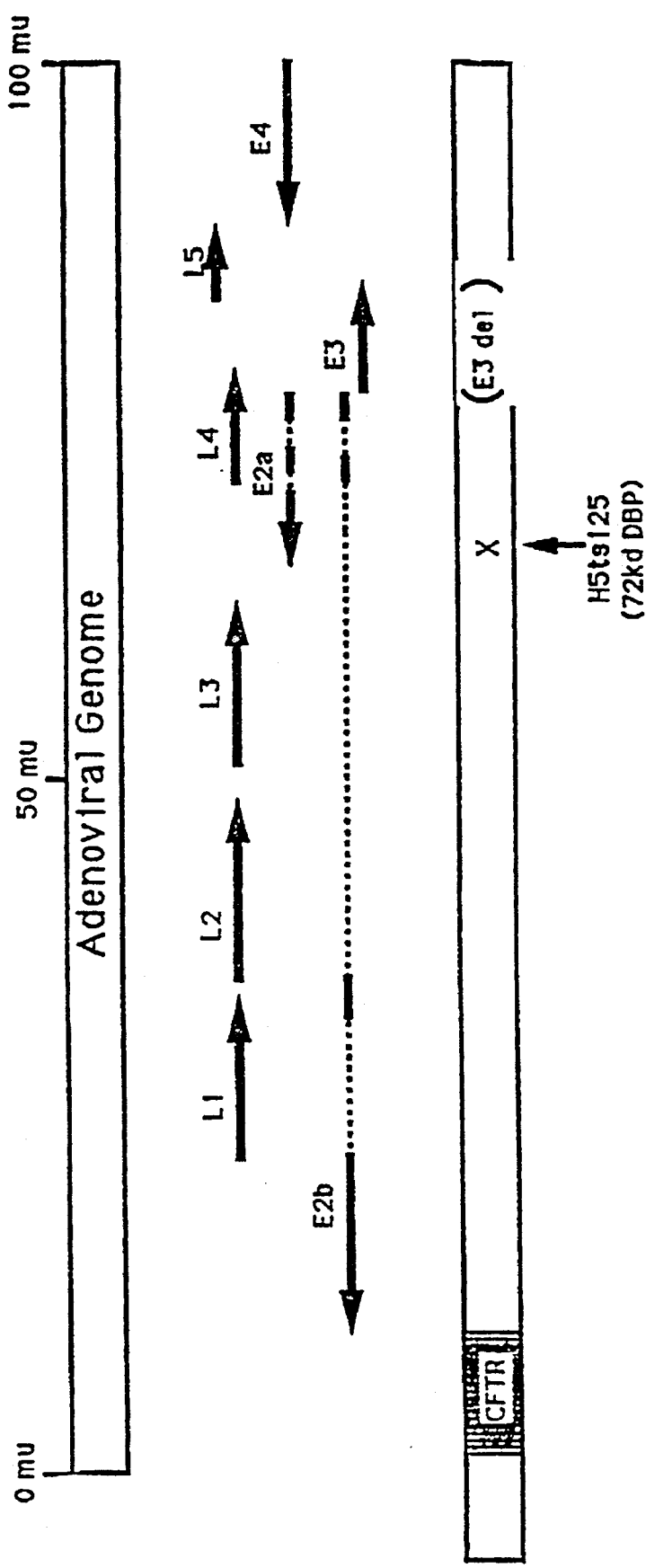
FIG. 3 is a map of two potential temperature-sensitive mutations in adenoviral replication.

Vectors with the CFTR minigene inserted into the E1-deleted region of sub360 and dl7001 backbones, also containing additional mutations in genes necessary for viral replication, have been produced. As further discussed below, the incorporation of the missense temperature-sensitive mutation found in the H5ts125 strain at 62.5 mu, is achieved by combining fragments from three independent DNA constructs including sub360 or dl7001, H5ts125, and a CFTR cDNA plasmid with E1a sequences placed 5' to the minigene cassette. These vectors are designated Ad.CB-CFTRts125sub360 and Ad.CB-CFTRts125dl7001. These vectors are identical except for the size of deleted regions in E3. FIG. 3 shows the location of the CFTR problem transgene within the E1-deleted region, E3-deletion, and the H5ts125 mutation with respect to other adenoviral genes. Due to the mutations in these vectors, there is reduced viral replication, reduction in expressed protein and an increase in the persistence of transgene expression. The following is a more detailed description of the production of the vectors of the present invention.

Temperature-sensitive vectors. In constructing the temperature-sensitive vectors of the present invention, temperature-sensitive (ts) adenovirus stocks, which served as "parental" stocks of vectors of the present invention, were generated. These vectors have ts mutations in the (DBP)E2a region. Specifically, a previously isolated temperature-sensitive mutant Hst125 of the adenovirus type 5 strain has been obtained. Vander Vliet, P. et al., *J. ViroL* 15:348–354 (1975). Hst125 has a single amino acid substitution (62.5 mu) at the carboxy end of the 72kd protein produced from the E2a gene. This protein product is a single-stranded DNA binding protein and is involved in the replication of adenoviral genomic DNA. At permissive temperatures (approximately 32° C.) this strain is capable of full life cycle growth on HeLa cells, while at non-permissive temperatures (approximately 38° C.) no replication of adenoviral DNA is seen. In addition, at non-permissive temperatures, decreased immunoreactive 72kd protein is seen in HeLa cells.

Two double mutant stocks have also been generated which contain the Hst125 mutation and E3 deletions. The E3 mutations are characteristic of the previously described mutant adenovirus type 5 strains, sub360 and dl7001. (sub360 published in Logan, J. et al., *Proc. Natl. Acad. Sci. (USA)* 81:3655–3659 (1984); dl7001 (kindly provided by Dr. William Wold, Washington University, St Louis)). Both mutant viruses contain a deletion in the E3 region of the adenoviral genome; in sub360, at 78.5 to 84.3 mu, and in dl7001, at 78.4 to 86 mu. The life cycle of both sub360 and dl7001 display wild type characteristics, as E3 is not required for replication of adenovirus.

The resultant new adenovirus mutants Hst125sub360 and Hst126dl7001 are used to generate CFTR recombinant adenovirus vectors which carry the Hts125 mutation and E3 deletion, wherein CFTR is inserted into the E1a/E1b-deleted regions. The CFTR gene cassette is driven by the CMV enhancer and β-actin promoter. As stated above, the resultant recombinant adenovirus vectors are designated Ad5.CB-CFTRst125sub360 and Ad5.CB-CFTRst125dl7001.

Temperature-sensitive CFTR vectors. The following is a more detailed description of the generation of the CFTR recombinant adenovirus of the present invention. The plasmid Pad.CB-CFTR was linearized by Nhe I cleavage. 293 cells were cotransfected with Ad.CB-CFTR and the large fragment of Cla I-cut Hst125dl7001 or Hst125sub360 DNA, to allow homologous recombination to occur. The recombinant adenoviral DNA was replicated and encapsidated into infectious virions, as evidenced by formation of plaques. Virus was isolated from individual plaques following incubation at 32° C., and amplified in 293 cells. As expected, no viral plaques were seen at 38° C., the nonpermissive temperature. Recombinant adenoviruses containing the human CFTR cDNA were identified by restriction cleavage and Southern blot analysis. Two of the recombinant viruses positive for CFTR were plaque-purified a second time, and designated Ad.CB-CFTRts125dl7001 and Ad.CB-CFTRts125sub360. These viruses were propagated in 293 cells by infection at 32° C. After 56 hr, viruses were recovered by 3 cycles of freeze thawing. All viral preparations were purified by CsCl density centrifugation and either followed by gel filtration to remove CsCl for immediate use, or stored at −20° C. after a 1:5 dilution into a glycerol/BSA solution. Titers of viral stocks were determined by plaque assay using 293 cells.

As those skilled in the art will realize, related adenoviral serotypes such as adenovirus type 2, as well as any of the forty-one adenoviral serotypes, may be substituted for the adenoviral type 5 vectors described in the present invention. Thus, it is not Applicants' intention to be bound by a specific adenoviral type.

SPECIFIC EXAMPLE 3—Primate Studies

The primate studies have attempted to simulate the clinical trials in order to assess toxicity and biological efficacy with first generation vectors. The results are tabulated in Tables I–X, which are set forth at the end of this Specific Example. Although transgene (CFTR) expression was achieved, side effects of the first generation vectors included lung tissue inflammation. One aspect of the preferred second generation vectors of the invention is to ameliorate such inflammation.

A. STUDY I—Feasibility

The goal of this study was to assess the feasibility of selectively delivering recombinant adenovirus to a single segment of a dependent lobe. The highest dose of virus proposed in the clinical trials was used in this experiment. A lacZ virus of similar structure to the Ad.CB-CFTR was used so that the distribution of gene expression in the whole lung could be accurately evaluated using sensitive and specific histochemical stains. More specifically, the lacZ transgene cassette is substituted for the CFTR transgene; all adenoviral sequences are the same. Specific goals were to assess short-term toxicity and to evaluate the distribution of recombinant gene expression within and beyond the targeted pulmonary segment.

Materials and Methods

Animal. A 12-year old, 32.5 kg baboon (Papio anubis) was used for this study (CFB1). During pre-transfection evaluation, it was found that the animal was hypoxemic ($PaO_2$ 54 mmHg) and hypercarbic ($PaCO_2$ 55 mmHg). Chest X-ray showed that his right upper and right middle lobes were collapsed. It was decided that he was unsuitable as a long-term animal and therefore was used for a short-term feasibility study. Subsequent experience led to the conclusion that the majority of the abnormalities in gas exchange were due to atelectasis that occurred during anesthesia, rather than intrinsic lung disease.

Anesthesia. The animal was sedated with intramuscular tiletamine/zolazepam (Telazol) (2.2 mg/kg). Repeated injections were used to maintain adequate sedation. An intravenous catheter was inserted into a saphenous vein and Ringer's lactate infused during the procedure. The animal breathed room air during the procedure.

Virus administration. The animal was intubated with a 9 mm cuffed endotracheal tube by the oral route. Benzocaine (20%) was sprayed into the endotracheal tube. An Olympus BF 1T20 flexible fiberoptic bronchoscope was introduced into the airway. Inspection of the airway revealed no proximal obstructing lesion which would explain the right upper and right middle lobe collapse seen on chest X-ray. The bronchial mucosa was slightly friable throughout the tracheobronchial tree. A 5 Fr double lumen balloon catheter was inserted into the left lung through the bronchoscope channel. The tip was guided into the orifice of the posterior segment of the left upper lobe and the balloon was inflated with 0.8 ml of air. Twenty-five ml of Ad. CMV-lacZ virus in normal saline ($1 \times 10^{11}$ pfu/ml) was injected through the catheter into the cannulated segment. Five ml of air was injected to clear the catheter of virus-containing fluid. The animal did not cough and no liquid was seen to leak from the bronchial orifice during the infusion. The catheter with balloon inflated was held in place for 8 minutes. At the end of that time, palpation of the animal's pulse detected several premature beats. The catheter and scope were removed. The animal was kept in the supine position for another 10 minutes. During this time, the animal was ventilated with an ambu-bag because 4–5 premature beats/minute were noted.

The animal did not cough during this period. Within 10 minutes, the premature beats were no longer detected and the animal was returned to his cage where he recovered uneventfully.

Follow-up: Necropsy. The animal was sedated with tiletamine/zolazepam (Telazol) (2.2 mg/kg) and sacrificed with pentobarbital/phenytoin. A necropsy was performed. The lung was inflation fixed and stained en bloc in Xgal.

Results

The animal tolerated the procedure well without clinical evidence of toxicity. Necropsy was performed with full gross and histopathology.

Figure 4:
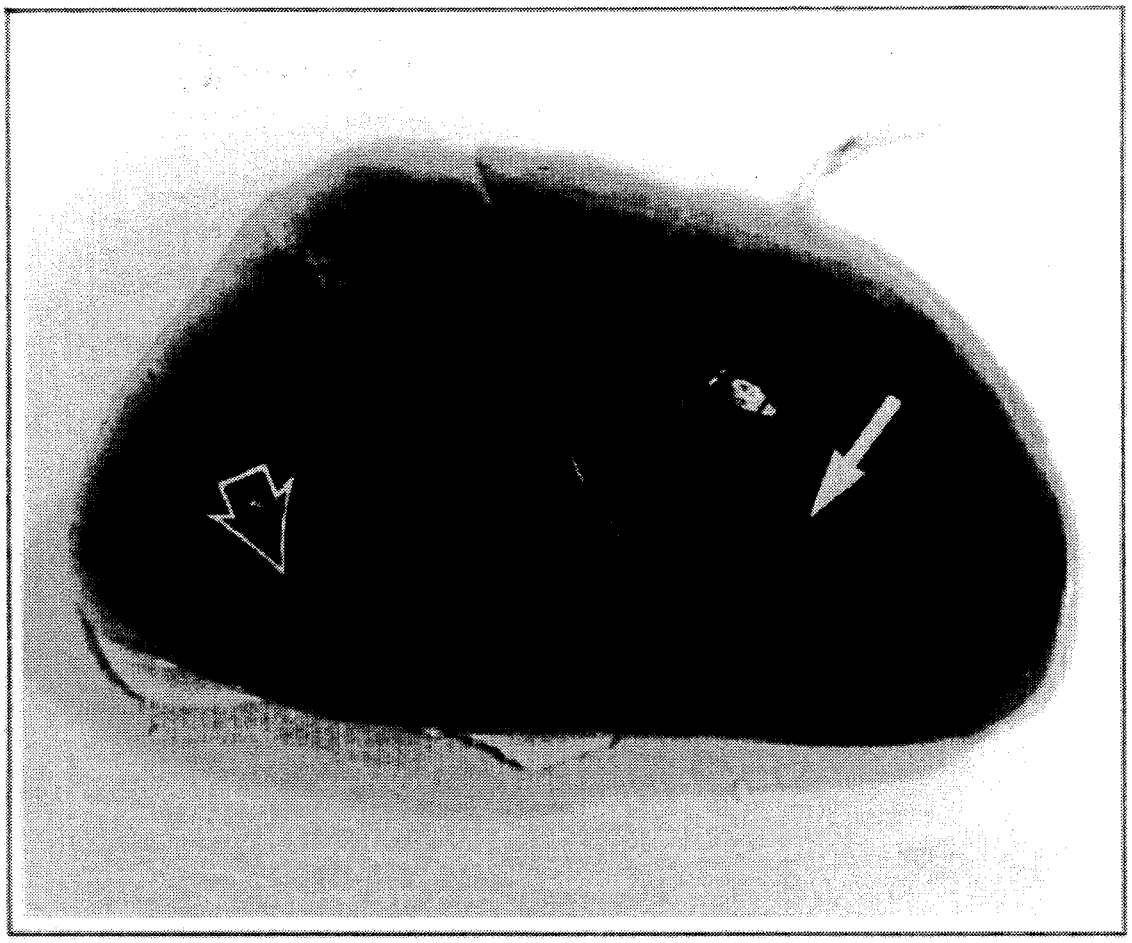
FIG. 4 is a photomicrograph of an Ad.CMVlacZ infected baboon lung stained in situ for β-galactosidase with Xgal.
Figure 5A:
FIGS. 5(A–B) are photomicrographs of Xgal stained tissue from CFTR and lacZ infused lobes of the CFB4 animal.
Figure 5B:
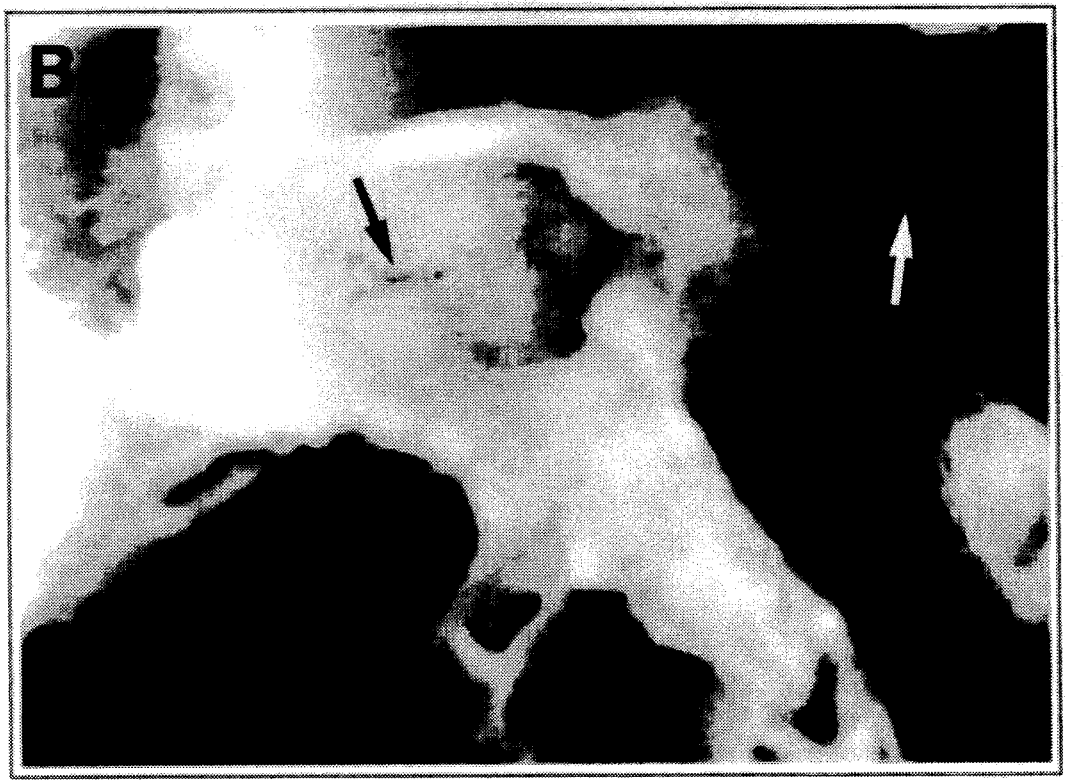
Figure 6A:
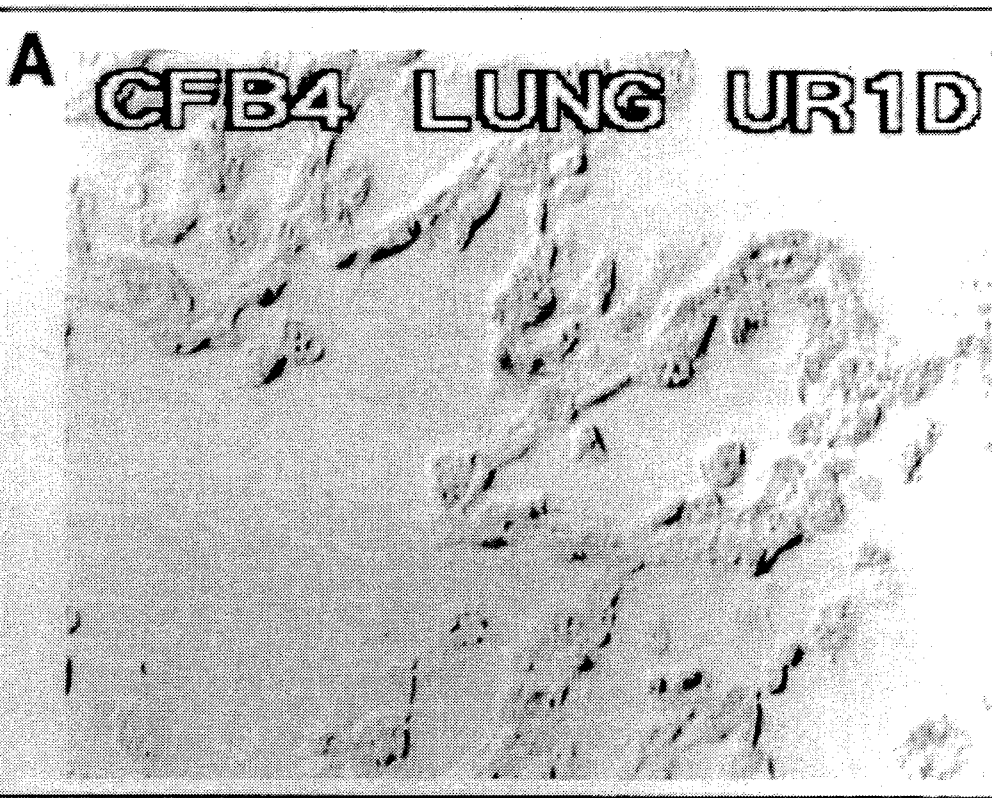
FIGS. 6(A–B) are photomicrographs of Xgal stained tissue from CFTR and lacZ infused lobes of the CFB4 animal.
Figure 6B:
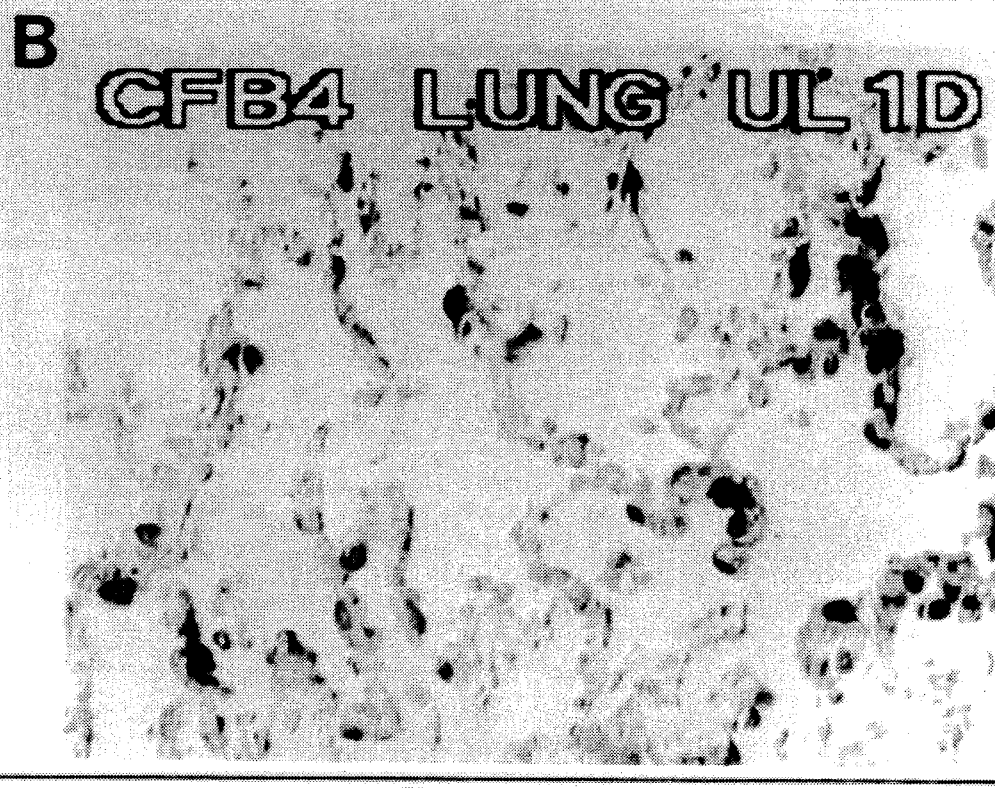

Three days post-infection, the baboon was euthanized and the main stem bronchi to the left lung was ligated to tubing. The baboon's two lungs were inflation fixed in 0.5% glutaraldehyde/PBS for 2 hr followed by rinsing in 1 mM $MgCl_2$/PBS two times for 15 min each. The lung was then stained en bloc in Xgal solution for 30 min at 37° C. by filling the lung with reaction mixture in addition to immersing the lung in the same buffer. The Xgal solution was then removed and the lungs were postfixed in buffered formulin. The reaction proceeded for two hours. Gross inspection of the left lung revealed intense Xgal reaction product apparently confined to the posterior segment of the left upper lobe. As shown in FIG. 4, a small focus of reaction product was seen in the left lower lobe. In FIG. 4, the solid arrowhead points to the Xgal reaction product in the segment infused with virus, while the open arrowhead marks an area in which virus leaked into an adjacent segment of a neighboring lobe. Histological sections revealed recombinant gene expression primarily in alveolar cells and patchy but sparse expression in conducting airway, similar to what was seen in Xgal stained tissue from CFTR and lacZ infused lobes of a CFB4 animal shown in FIGS. 5 and 6. (The protocol for the CFB4 animal was as follows: the most proximal segment of the right upper and left upper lobes of the CFB4 animal was infused with seven ml of Ad.CB-CFTR and Ad. CMVlacZ at a concentration of $1\times10^{10}$ pfu/ml. Samples from quadrant 1D were fixed in 0.5% glutaraldehyde/PBS and stained on block for β-galactosidase with Xgal for 30 min. Tissue was embedded in paraffin, sectioned at 5µm, and stained briefly in hematoxylin). The photomicrographs of FIG. 5 show on fos views from a dissecting microscope from the Ad.CB-CFTR infected lobe (FIG. 5A) and the Ad.CMVlacZ infected lobe (FIG. 5B). The black arrow points to Xgal positive cells in bronchus, while the white arrow points to Xgal positive regions in the alveoli. The photomicrographs of FIG. 6 show sections from the Ad.CB-CFTR infected lobe (FIG. 6A) and the AD.CMVlacZ infected lobe (FIG. 6B). On gross examination, the lungs appeared normal. Atelectasis complicated interpretation of the histologic sections. However, focal areas of alveolitis with nonsuppurative perivascular mononuclear cell infiltrates were seen confined to the areas of the lung in which the gene was instilled (discussed in more detail below).

B. STUDY II—Toxicity

The goal of this study was to assess the long term toxicity of recombinant adenovirus delivered to pulmonary segments. In addition, an attempt to evaluate the sensitivity and specificity of bronchoscopic techniques for detecting recombinant gene expression and adenoviral infection was made. A large baboon was administered maximal doses ($1\times10^{10}$ pfu/ml) of Ad.CMV-lacZ and Ad.CB-CFTR to individual pulmonary segments. The animal has been studied with several bronchoscopies with bronchoalveolar lavage and brushings, with specimens analyzed for pathology as well as lacZ and CFTR expressing cells.

Material and Methods

Animal. A 12-year old, 32.5 kg male baboon (Papio cynocephalus/anubis) was used for these studies (CFB2). He was maintained in a cage separate from other animals and fed a standard diet.

Anesthesia. The animal was sedated with intramuscular tiletamine/zolazepam (Telazol) (2.2 mg/kg). Sedation was maintained by supplemental injections with the same agent and with intramuscular butorphanol (0.02 mg/kg). An intravenous catheter was inserted into a saphenous vein and Ringer's lactate was infused during the procedure. On follow-up study days, the animal was initially sedated with intramuscular tiletamine/zolazepam, but supplemental sedation was accomplished with intravenous thiamylal (2.5 mg/kg) as needed.

Chest X-rays and specimen collection. Ventral-dorsal and left lateral recumbent chest X-rays were performed. Blood was drawn from the femoral artery and analyzed for arterial blood gases, chemistries, hematologic measurements, coagulation parameters, and viral cultures (see below). A urethral catheter was inserted into the urinary bladder and urine was obtained for routine analysis and viral culture. Cotton swabs were used to obtain rectal and pharyngeal samples for viral culture.

Bronchoscopic sampling. A 9 mm cuffed endotracheal tube was inserted into the trachea by the oral route. A FB-18X Pentax fiberoptic bronchoscope was passed into the trachea and advanced to a wedged position in the right middle lobe. Twenty five ml of sterile saline was instilled and immediately aspirated yielding 12 ml for analysis. Next, 3 bronchial brushes were used to obtain epithelial cells from the right middle lobe bronchus. Each brush was advanced approximately 3 cm into the lobar orifice and rubbed back and forth. The distal 4 cm of the brushes were cut off and dropped into Ham's F12 medium.

Virus administration. The fiberoptic bronchoscope was inserted into the trachea and advanced to the orifice of the posterior segment of the left upper lobe. A 5 Fr. double lumen balloon catheter was passed through the channel of the bronchoscope and advanced so that its balloon was just within the orifice of the segmental bronchus. The balloon was gently inflated to occlude the bronchus. Twenty ml of Ad.CMV-LacZ virus at $1\times10^{10}$ pfu in normal saline was infused into the segmental bronchus through the catheter lumen. The catheter was kept in place for 10 minutes and then removed. Next the bronchoscope was directed to the segmental orifice of the posterior segment of the right upper lobe. As on the left side, a balloon catheter was used to instill 20 ml of Ad.CB-CFTR into the segmental bronchus. Prior to and after the infusion of virus, the animal had apneic episodes, presumably from the accumulated effects of repeated intramuscular sedation. Intermittently during and after the infusion, the animal was ventilated by Ambu bag until spontaneous respirations became steady. Naloxone and doxepram were also given. The animal was returned to his cage and recovered uneventfully.

Follow-up studies. On days 3, 14, 21, 73, 77, 79, 93, 102, 116 and 152 the animal was anesthetized. Chest X-rays were obtained, and blood, urine, stool, and pharyngeal specimens were taken. On days 3 and 21, the trachea was intubated and the bronchoscope used to obtained bronchoalveolar lavage fluid and bronchial brush specimens from the posterior segment of the right and left upper lobes as outlined above.

Results

The animal tolerated the procedure well and experienced no obvious clinical toxicity. The animal continues to gain weight and its vital signs remain within normal limits. The laboratory results from the multiple studies performed were recorded together with the results of Study III in Tables II–X and FIGS. 8–12. To summarize the results for CFB2, the blood hematologies (Table II), coagulation profile (Table II), chemistries (Table III), and urinalyses (Table IV) have remained within normal limits with the exception of hepatic enzyme levels (Table III). Mild elevations of transaminase were seen prior to gene transfer. The elevated levels have either persisted or improved during the follow-up period. Arterial blood gases (Table V) showed baseline hypoxemia and hypercarbia (discussed below). To monitor for changes in gas exchange during the follow-up period, the $P(A-a)O_2$ was used. There was an increase in $P(A-a)O_2$ that peaked on day 21 and decreased to below baseline on day 116 post gene administration. Chest X-rays (Table VI) showed mild upper lobe haziness prior to gene administration. The abnormalities worsened by day 21 on the left side. Thereafter, the chest radiographs returned to normal.

Figure 7A:
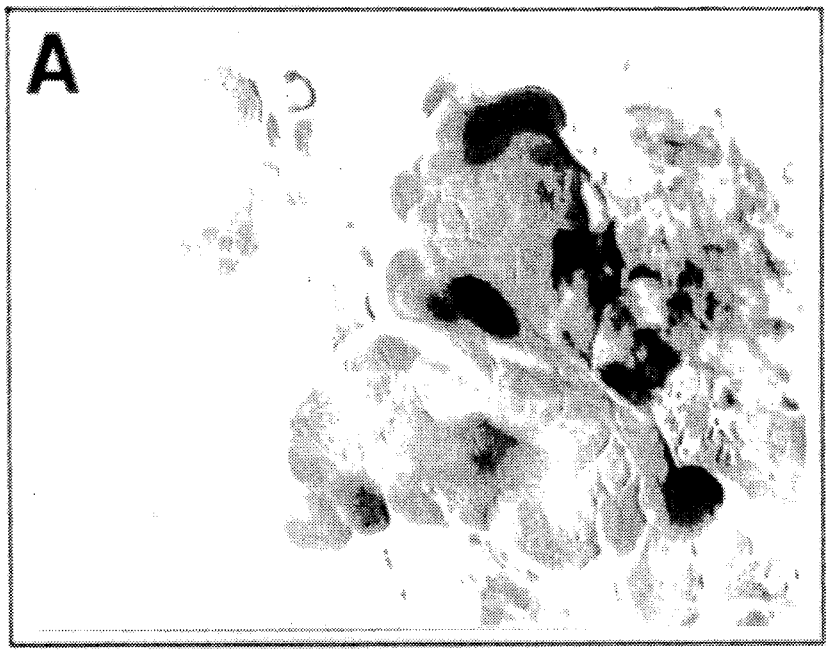
FIGS. 7(A–B) are photomicrographs showing transgene localization in bronchial brushings of the CFB4 animal.
Figure 7B:
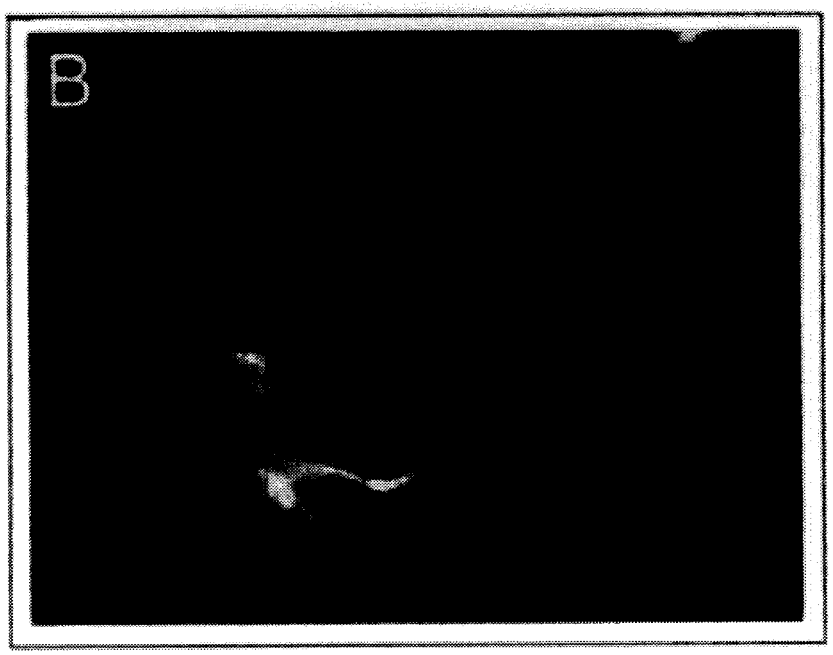

Analysis of BAL fluid cell number and differential (Table VII) is discussed in conjunction with the Dose/Toxicity Study III, below. As shown in the photomicrograph of FIG. 7A, histochemical Xgal staining of cytocentrifuged preparations of bronchial brushing, from the Ad.CMVlacZ infused left upper-lobe of the CFB4 aminal, showed lacZ expression in 5.2% of cells in BAL fluid that were recovered from the lacZ segment on day 4; a single lacZ cell was recovered on the contralateral side. CFTR expression was detected in 3.4% of cells in BAL fluid from the CFTR segment (see FIG. 7B). As shown in the photomicrograph of FIG. 7B, immunocytochemical CFTR staining of cytocentrifuged preparations of bronchial brushings from the Ad.CB-CFTR infused right upper lobe of the CFB4 animal showed CFTR in 2.1% of the cells that received the Ad.CB-CFTR (Table VIII). No transgene expression was detected in cells recovered from brushings or BAL beyond 4 days after infusion.

The results of culture for viral shedding and recovery is presented with the results from the Dose/Toxicity Study III below, (Tables IX and X).

C. STUDY III—Dose/Toxicity Study

This study used 12 baboons to determine the efficacy and toxicity of adenovirus-mediated gene transfer (Table I). Each of the 12 animals received intrabronchial instillation of Ad. CMV-lacZ into the posterior segment of the left upper lobe and Ad.CB-CFTR into the posterior segment of the right upper lobe. The animals were divided into four groups of 3 animals, with each group receiving a different concentration of virus in the fluid instilled into the bronchi: $1 \times 10^7$, $10^8$, $10^9$ or $10^{10}$ pfu/ml. One member of each of the four groups was necropsied on day 4 following gene infusion, another on day 21, and the remaining animal was kept alive for long-term evaluation.

Materials and Methods

Animals. The 12 baboons (Papio) used for the main dose-response study were 2 to 5-year old and weighed 7 to 14 kg (Table I). All animals were caged separately and fed standard diets.

Sedation. After allowing no oral intake for 12 hours, the animals were sedated by intramuscular injection of 2.2 mg/kg tiletamine/zolazepam (Telazol). Adequate sedation was maintained either with repeated intramuscular doses of the same agents or with intravenous thiamylal (2.5 mg/kg).

Specimen collection and chest radiographs. After sedation, arterial blood was drawn from the femoral artery into a heparinized syringe for measurement of blood gases, and aliquots were placed into sodium EDTA for measurement of blood counts, into glass tubes for measurements of serum chemistries and antibodies, into a heparinized tube for viral culture, and into sodium citrate for measurement of prothrombin and partial thromboplastin times. A urethral catheter was inserted into the bladder to obtain urine for routine analysis and viral culture. The clinical laboratories of University Hospital, Ann Arbor, MI were used to analyze the blood for cell counts, differential counts, coagulation measurements, and arterial blood gases; the serum for electrolytes, blood urea nitrogen and creatinine, calcium, phosphate, total protein, albumin, aspartate and alanine transaminase, alkaline phosphatase, lactic dehydrogenase, and bilirubin; and the urine specimens for routine urinalysis. Nasopharyngeal secretions and rectal stool samples were collected by cotton swabs. These samples together with blood, urine, and bronchoalveolar lavage fluid were cultured for adenoviruses. Ventral-dorsal and left lateral recumbent chest radiographs were performed.

Bronchoscopy. A FB-10X Pentax fiberoptic bronchoscope was inserted through a 5.5 mm uncuffed endotracheal tube. Bronchoalveolar lavage was performed by instilling normal saline (10 ml for the smaller animals) through a wedged bronchoscope as a single bolus. The fluid was immediately aspirated and placed onto ice. Bronchial brushings were performed using 3–4 cytology brushes (Olympus BC-12C) for each segment sampled. The brushes were advanced approximately 2–3 cm beyond to the lobar orifice, rubbed back and forth, and then removed. The distal 4 cm of the brushes were cut off and dropped into Ham's F12 medium.

Study protocol After sedation and intratracheal intubation, bronchoalveolar lavage fluid and bronchial brushings were obtained from the right middle lobe. Ad.CMV-lacZ in 1% glycerol/normal saline was infused into the posterior segment of the left upper lobe and Ad.CB-CFTR in 1% glycerol/normal saline into the posterior segment of the right upper lobe. Unlike the procedure used for the two larger pilot animals, the balloon catheter could not be used in the smaller 12 animals because of limitations in size of the channel in the smaller bronchoscope. Instead, the virus was infused (7 ml of $1 \times 10^7$, $10^8$, $10^9$ or $10^{10}$ pfu/ml) through the internal channel of the bronchoscope with the bronchoscope wedged into the bronchial orifice. After viral instillation, the bronchoscope was kept wedged for 10 minutes. The bronchoscope was removed and the animal maintained in the supine position for a minimum of 10 more minutes. This technique appeared less satisfactory than using the balloon catheter as was done in the larger animals, because complete occlusion of the airway was difficult to maintain during and after viral infusion.

Follow-up: Necropsy. One animal from each group was sacrificed on day 4 and another on day 21. Immediately before sacrifice, the animal was anesthetized as outlined above, chest X-rays were performed, and clinical specimens including blood, urine, stool and pharyngeal secretions were taken. The animal was then sacrificed with pentobarbital/phenytoin (Beuthanasia) and a necropsy was performed.

Follow-up studies: Long-term animals. One animal from each group was kept alive for repeated evaluations. On days 4, 15, and 21, the animals were anesthetized, chest X-rays were obtained, and blood, urine, stool and pharyngeal specimens were taken. On days 4 and 21, the trachea was intubated and the bronchoscope used to obtained bronchoalveolar lavage fluid and bronchial brush specimens from the posterior segments of the right and left upper lobes as outlined above. Additional blood samples and chest radiographs were obtained on at least a monthly basis for the long-term animals.

Concurrent studies. Animals CFB3, CFB4, and CFB6 also participated in a study of adenovirus-mediated gene transfer into the nasal mucosa. Immediately prior to intrabronchial instillation of adenovirus as outlined above, the animals were placed into the right lateral recumbent position. A polyethylene catheter was inserted 4–5 cm into each nose and 0.8 ml of virus was infused over a 15 minute period into the right nostril and 0.8 ml vehicle (3.3% glycerol/33% PBS/63.7% normal saline) alone into the left. CFB3 and CFB4 received Ad.CB-CFTR at $1 \times 10^7$ and $10^{10}$ pfu/ml, respectively; CFB6 received Ad. CMV-LacZ at $1 \times 10^{10}$ pfu/ml.

General response of animals. The animals tolerated the bronchoscopic instillation of Ad.CB-CFTR and Ad.CMV-LacZ without complication except that 3 animals vomited immediately after intratracheal intubation prior to gene infusion. Two of these animals also vomited when intubated during the follow-up bronchoscopies. In none of these episodes was intratracheal aspiration observed bronchoscopically. During the post-transfection period, the behavior of the animals was normal. They continued to eat normally and their weight changed less than 3% in the post-transfection period. Rectal temperatures when measured while the animals were sedated for studies were never elevated.

Figure 8A:
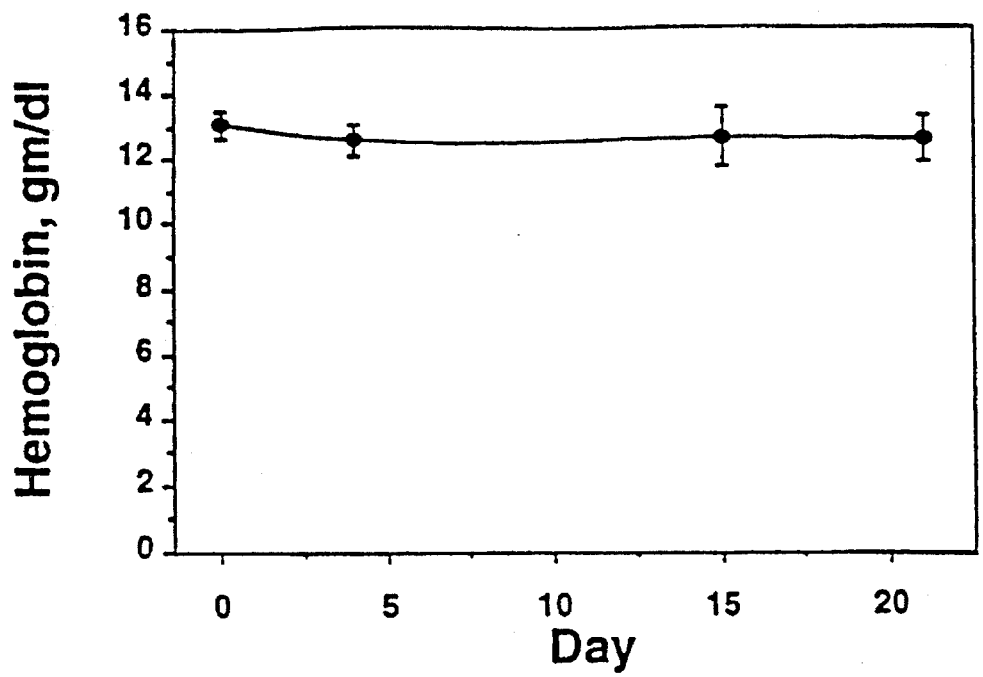
FIGS. 8(A–C) are graphs showing the effects of gene transfer on hematologic values.
Figure 8B:
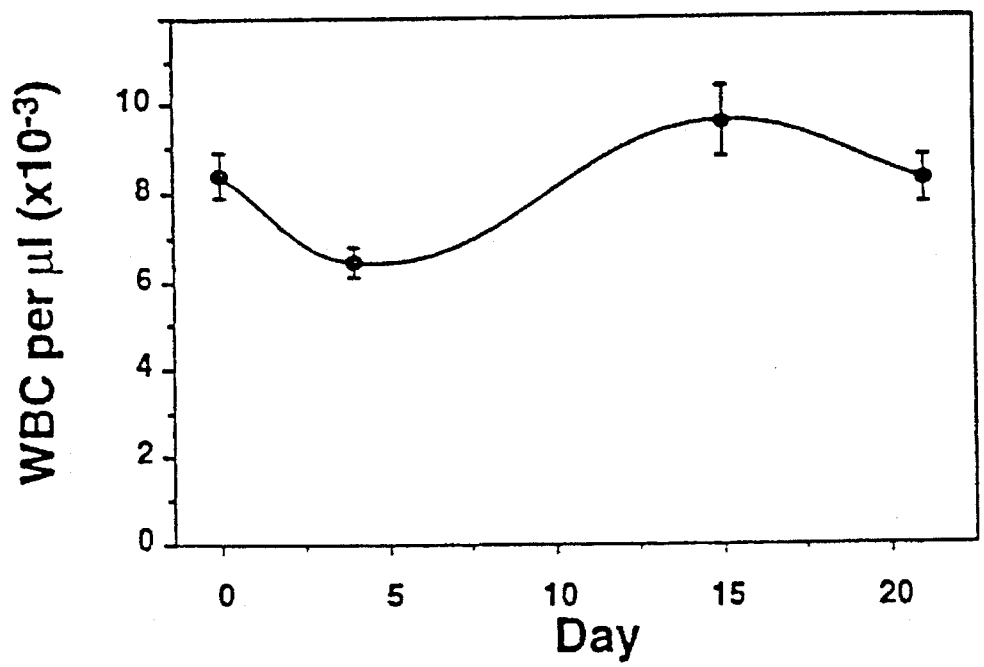
Figure 8C:
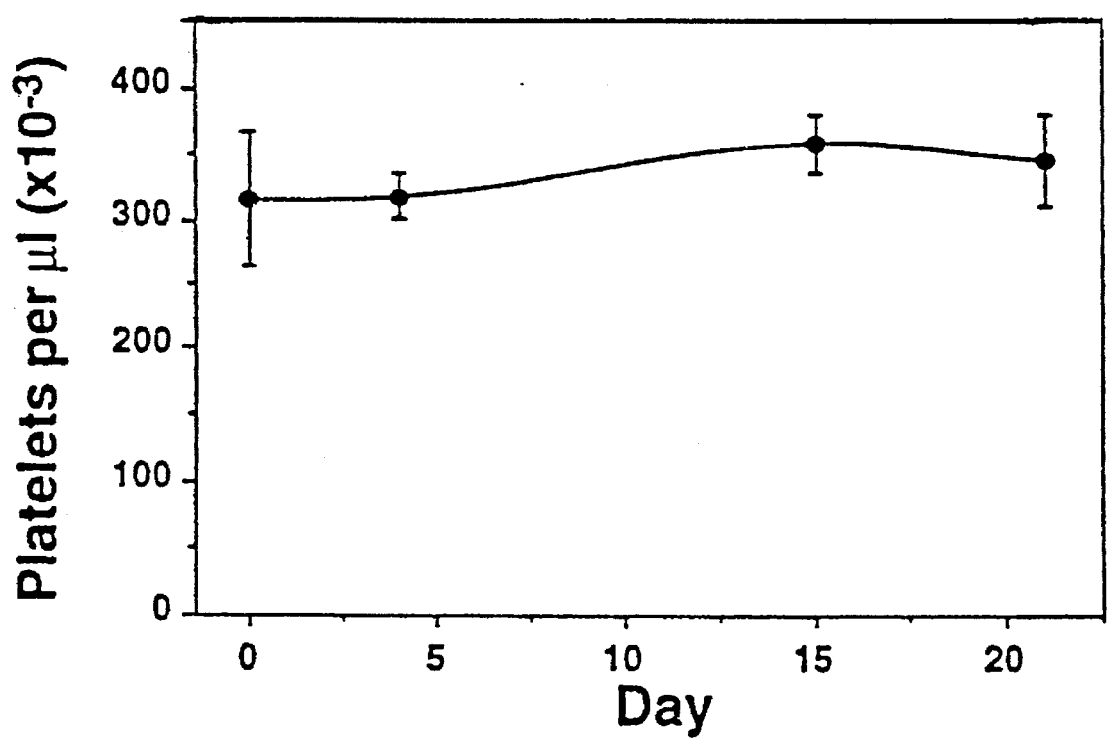
Figure 9:
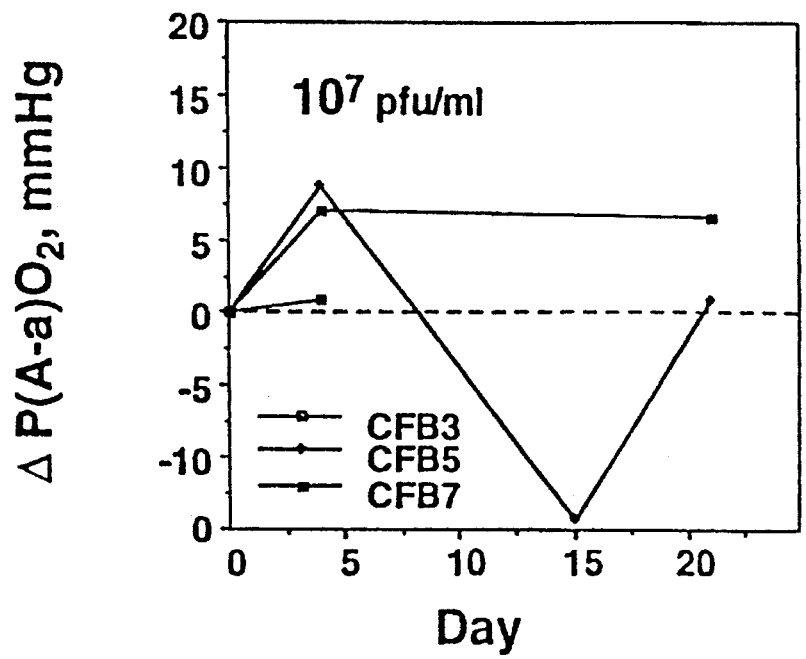
FIG. 9(A–D) are graphs showing the effects of gene transfer on the difference between alveolar and arterial oxygen tensions.
Figure 9:
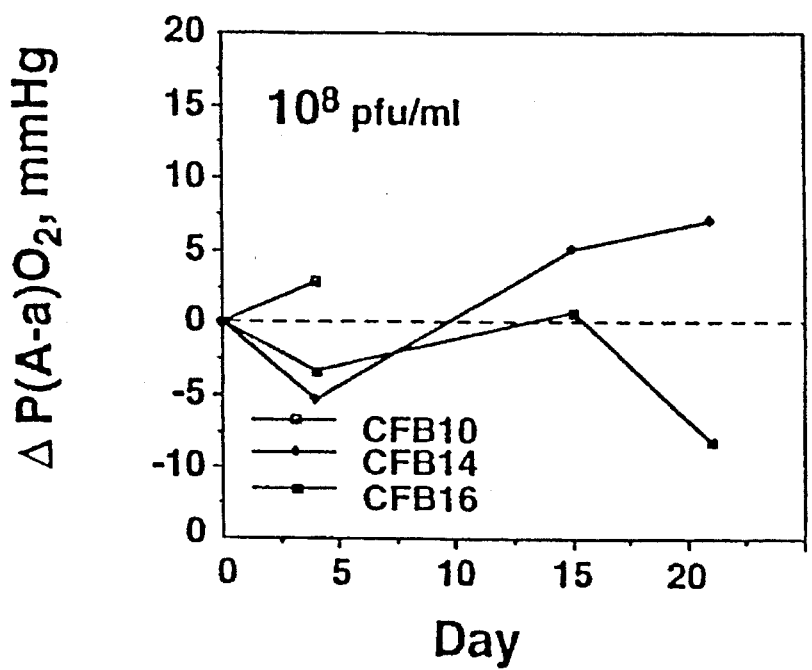
Figure 9C:
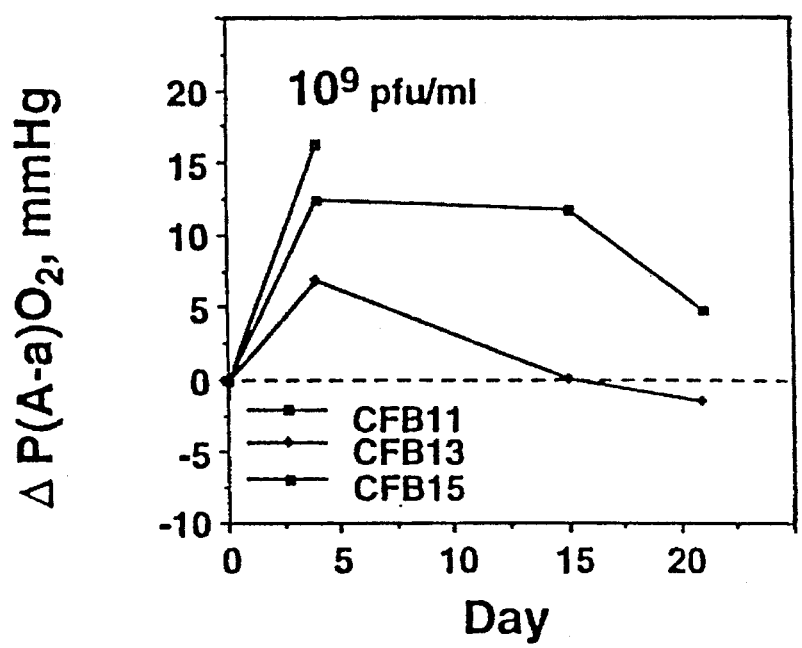
Figure 9D:
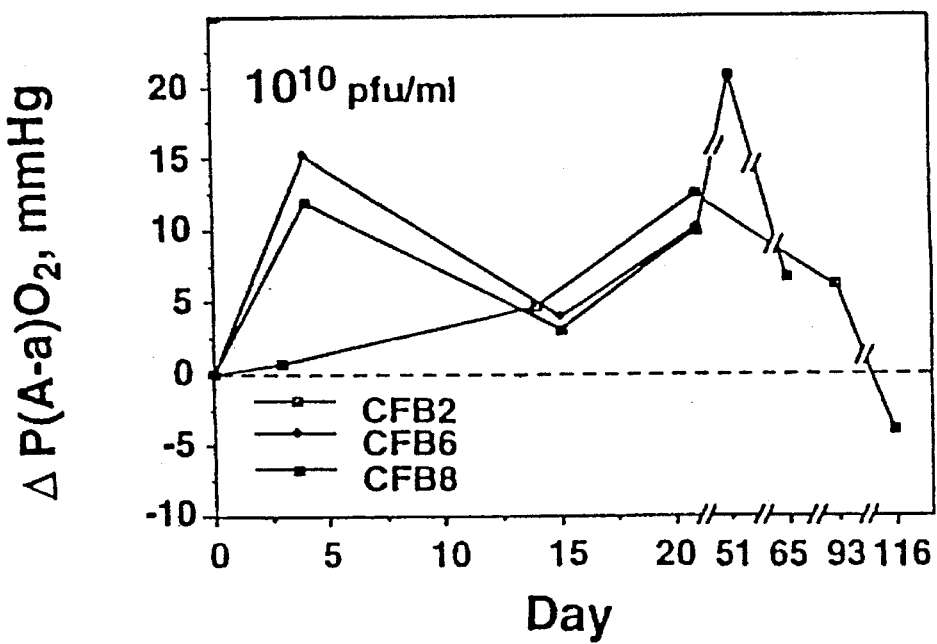

Hematologic counts and coagulation measurements. Blood was drawn into tubes containing sodium citrate from the femoral artery immediately prior to intrabronchial gene administration (day 0) and again on days 4, 15 and 21. As shown in FIG. 8A, blood hemoglobin concentrations remained within normal range in all animals during the 3 weeks following transfection. As shown in FIG. 8B, when the animals were analyzed as a single group, white blood cell counts decreased between day 0 and day 4 ($p<0.01$), but remained within the normal range. The extent of reduction was not directly related to viral dose. After day 4, the counts increased so that by day 15 they were no different from baseline ($p>0.1$). White blood cell differential counts were normal except that at some time during the study, 6 animals had mildly elevated percent monocytes (maximum of 11%). Three of these animals had monocyte elevations on day 0 prior to gene administration. The other 3 animals belong to groups that received $1 \times 10^7$, $10^8$, and $10^9$ pfu/ml doses. As shown in FIG. 8C, blood platelet counts (expressed as the mean±SEM of all animals tested) remained in the normal range on all measurements and did not change during the study. The prothrombin time and partial thromboplastin time remained within the normal range for during the study. Also, see Table II.

Serum electrolytes, proteins, enzymes and urinalyses. Serum concentrations of $Na^+$, $K^+$, and $Cl^-$ were normal and remained unchanged throughout the study. See Table III. Two animals had low serum $HCO_3^-$ levels on day 0 (15 and 17 mEq/L) prior to gene administration. Arterial blood pH was also low in these samples (discussed below). During the follow-up period, the $HCO_3^-$ increased toward the normal range. Calcium, phosphorous, total protein and albumin remained normal. Six animals had low levels of proteinuria on one or more urine samples during the study. See Table IV. Several of these were likely due to traumatic catheterizations since gross hematuria was also present in the catheterization specimen but not noted when the animals spontaneously voided later in the day. The proteinuria was not related to viral dose or the number of days post-transfection. Serum creatinine and blood urea nitrogen were normal in all animals throughout the study. Liver function tests (aspartate transaminase (AST), alanine transaminase (ALT), lactate dehydrogenase, alkaline phosphatase, and bilirubin were normal except for one animal that had mild enzyme elevations at baseline (e.g. AST 56 IU/L, ALT 85 IU/L) that remained stable or improved during the study. Prothrombin time and partial thromboplastin time were always normal.

Arterial blood gases. Arterial blood samples obtained while the animals were sedated prior to gene administration showed a moderately wide range of $PaCO_2$ levels with a mean±SD of 44.8±4.3 mmHg (range 36.7 to 54.7 mmHg). See Table V. The elevated $PaCO_2$ levels are likely due to hypoventilation and atelectasis which has been previously reported when baboon are sedated. The measured levels of $PaCO_2$ remained elevated throughout the study with no changes directly related to viral dose or to the number of days post-transfection.

As mentioned above, arterial blood pH levels were low in two animals at baseline prior to gene transfection (pH 7.15 and 7.28). The $PaCO_2$ levels were no higher in these two animals, so acute hypoventilation was not solely responsible. The anion gap ($Na^+-[K^++HCO_3^-]$) was increased indicating a metabolic acidosis. The unmeasured anions were not identified, but were unlikely to be ketone bodies because none were detected in the urine. During the study, the low pH levels improved in these animals; the pH of one animal increased from 7.15 to 7.32 by necropsy on day 4, and of the other animal from 7.28 to 7.39 by day 15.

Baseline $PaO_2$ was 78.1±11.0 mmHg (mean±SD, range 54.0 to 98.0 mmHg). To compensate for changes in $PaO_2$ caused by changes in ventilation, the $PaO_2$ data were analyzed using the calculated alveolar to arterial oxygen gradient ($P(A-a)O_2$) using measured arterial $PaO_2$ and $PaCO_2$. Blood was drawn from the femoral artery immediately prior to intrabronchial gene administration (day 0) and again on days 4, 15 and 21. Additional samples were obtained on later days from the long-term animals receiving $1 \times 10^{10}$ pfu/ml viral dose. The mean $P(A-a)O_2$ on day 0 prior to gene administration was 12.5±7.0 (SD) with a range of 0.0 to 26.6. Because the wide range of baseline $P(A-a)O_2$ levels might obscure a treatment-induced change in gas exchange, the data were analyzed using the change in $\Delta P(A-a)O_2$ from the day 0 level ($\Delta P(A-a)O_2$). When analyzed in this fashion, no statistically significant effect on $\Delta P(A-a)O_2$ was found for viral dose or from the time interval post-transfection. However, inspection of the relationship between $\Delta P(A-a)O_2$ and the number of days post-transfection did suggest a trend. FIGS. 9A–9D show the change in $P(A-a)O_2$ in mmHg from the level on day 0 ($\Delta P(A-a)O_2$) for groups of animals receiving each dose of virus. The higher dose animals ($1 \times 10^9$ and $10^{10}$ pfu/ml) were more likely to have an increase in $P(A-a)O_2$ while the lower dose animals ($1 \times 10^7$ and $10^8$ pfu/ml) were more equally distributed between increased and decreased $P(A-a)O_2$ after gene administration.

Figure 10:
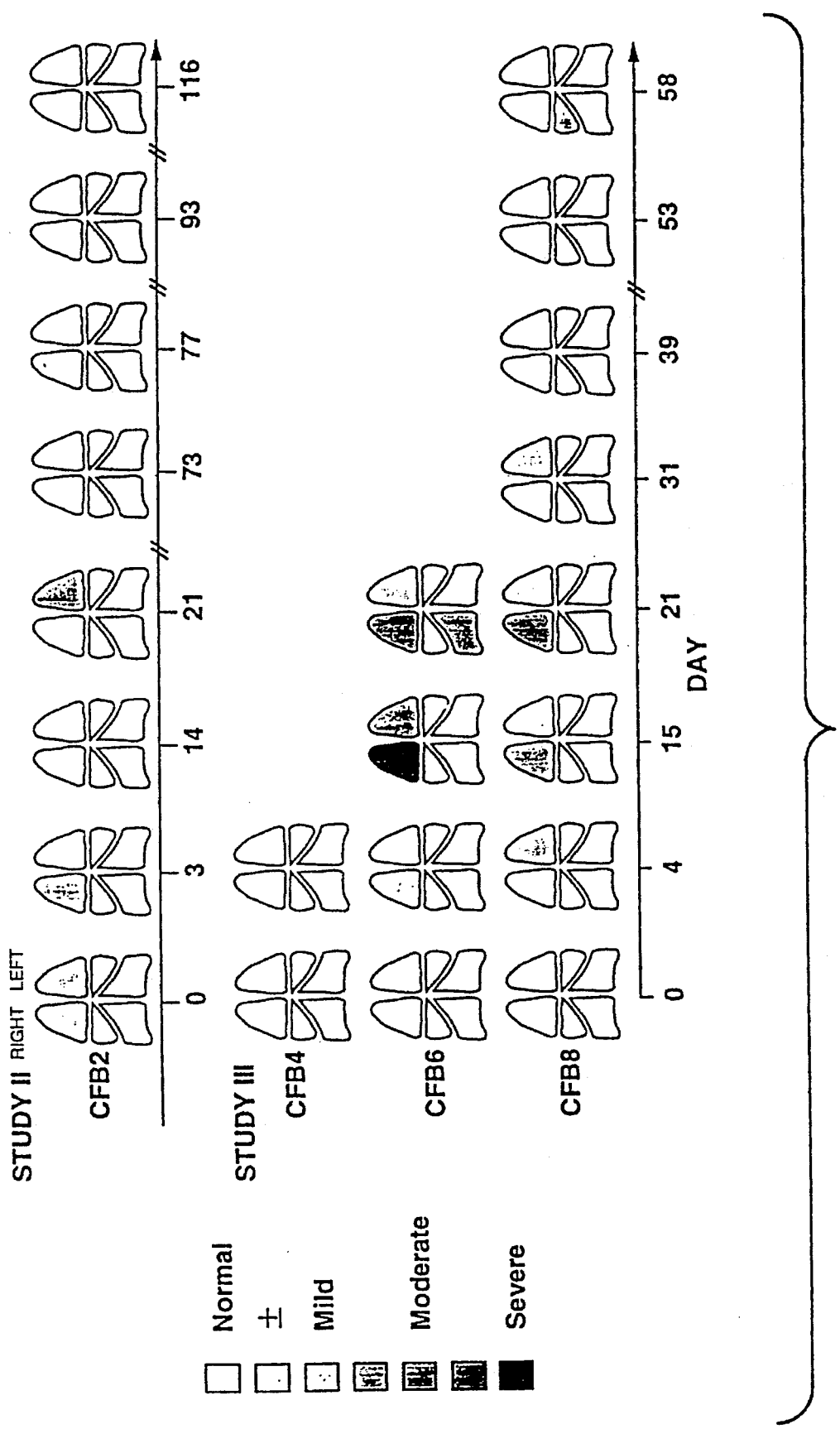
FIG. 10 is a schematic showing the location and extent of chest radiographic abnormalities detected before and after gene administration.

Chest radiographs. Supine ventral-dorsal chest radiographs were taken in all animals. See Table VI. Detection of infiltrates was complicated by transient atelectasis that apparently occurred when the animals were sedated. It was noted that the side of the animal on which the atelectasis occurred was often the side on which the animal was lying prior to taking the X-ray. Repositioning the animal into the opposite decubitus position for a minute and then rotating him to the supine position would expand the atelectatic area. After compensating of these artifacts, it was then possible to analyze the chest radiographs for appearance of abnormalities. No infiltrates appeared in any animal receiving $1 \times 10^7$, $10^8$, or $10^9$ pfu/ml doses. New alveolar infiltrates occurred only in 3 of the 4 animals receiving $1 \times 10^{10}$ pfu/ml dose. To localize and quantify the extent of infiltrate, a grading system was used. The upper, middle, and lower lung fields of each lung were graded for alveolar infiltrates: "mild"—minimally detectable infiltrate; "moderate" infiltrate occupying ¼ of lung field; "severe"—infiltrate occupying ½ or more of lung field. FIG. 10 shows the location and extent of chest radiographic abnormalties detected before and after gene administration in animals receiving a $1 \times 10^{10}$ pfu/ml dose. As shown in FIG. 10, the infiltrates generally first appeared on days 15 and 21 post-transfection. In one of the long-term animals, streaky infiltrates were present in both upper lobes on day 0 prior to transfection. The infiltrate worsened on day 21, but completely resolved by the radiograph taken on day 73. The infiltrate that appeared in the other long-term, $1 \times 10^{10}$ pfu/ml animal completely resolved by the X-ray performed on day 39.

Results

Figure 11A:
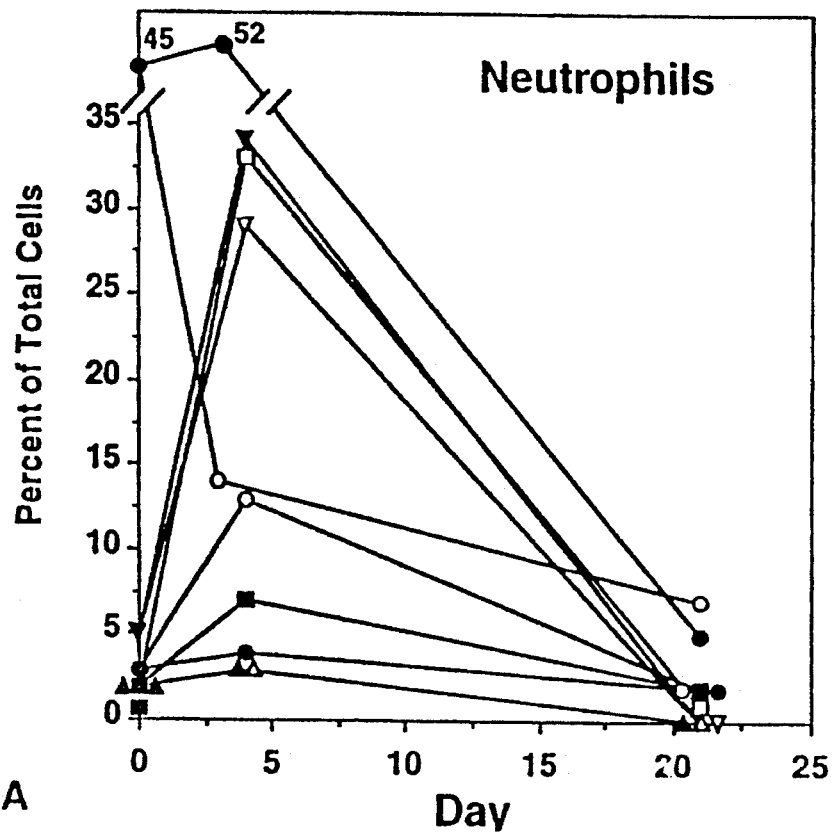
FIG. 11(A–B) are graphs showing bronchoalveolar lavage fluid differential cell counts before and after gene administration.
Figure 11B:
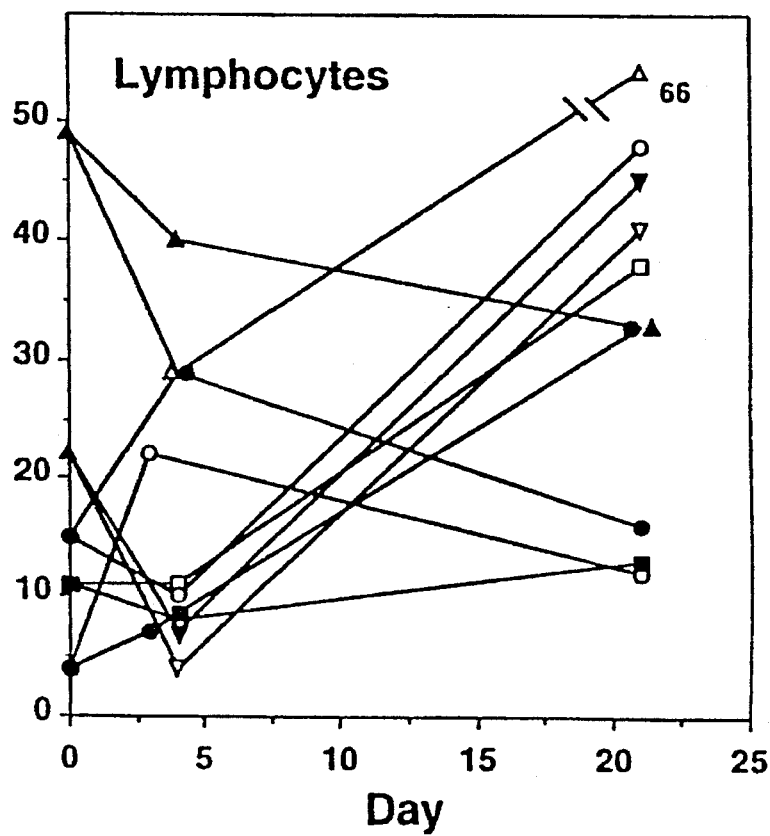

Bronchoscopic results. Bronchoalveolar lavages was performed on long-term animals 3 times during the study and the results are shown in FIG. 11A and 11B and Table VII. On day 0, the right middle lobe was lavaged (solid symbols in FIGS. 11A and 11B), and on days 4 and 21 the posterior segments of right (solid symbols in FIGS. 11A and 11B) and left (open symbols in FIGS. 11A and 11B) upper lobes were lavaged. Cytocentrifuge preparations were made and the cells stained with a modified Wright's stain. In FIGS. 11A and 11B, data from animals receiving $1 \times 10^7$ (□, ■), $10^8$ (△, ▲), $10^9$ (▽, ▼), or $10^{10}$ (○, •)pfu/ml are displayed separately. Approximately 50% of the instilled volume was recovered with no variation depending on viral dose or time following gene administration. The cell concentration of the bronchoalveolar lavage fluid obtained from the right middle lobe on the day of gene instillation was $2.32 \times 10^6 \pm 1.08 \times 10^6$ (SD) cells/mi. Cell numbers measured in lavage fluid from the follow-up bronchoscopies showed no relationship to day, dose, or side on which the lavage was performed. Analysis of the cell differential counts was complicated by the finding that on day 0, one animal had markedly elevated percent neutrophils and another had elevated percent lymphocytes. Even with these suspected outliers, the percent neutrophils when analyzed for all animals changed significantly over time ($p<0.03$) with a peak at 4 days and a reduction back to baseline at day 21. (See FIG. 11A). This pattern occurred independent of the dose of virus administered. The percent lymphocytes also changed significantly over time ($p<0.04$) with an increase occurring later than the neutrophils, between day 4 and day 21. This increase was not influenced by the dose of virus administered and was independent of the side lavaged. Sporadic increases were seen in percent eosinophils; often the eosinophils were present in only one of the two segments lavaged (not consistently the left or right side) and then only for a single point in time.

Cytocentrifuge smears were stained with Xgal to detect β-galactosidase activity (Table VII). Blue-staining cells were present within the cell populations obtained from animals receiving $1 \times 10^{10}$ pfu/ml doses at the day 3 or 4 time point. No cells stained positively for β-galactosidase from fluids obtained at other times or from animals receiving lower concentrations of virus. The cells obtained from one $1 \times 10^{10}$ pfu/ml dose animal were stained for CFTR using immunocytochemistry. Small numbers of cells (3.4%) stained positively on day 3 after gene administration.

Bronchial brushings. Cytocentrifuge smears of cells obtained by bronchial brushings were analyzed for transgene expression by staining for β-galactosidase with Xgal and for CFTR by immunocytochemistry. See Table VIII and FIG. 7A and 7B. Small numbers of cells stained positively in samples obtained from animals 3 or day 4 after receiving $1 \times 10^{10}$ pfu/ml doses.

Vital cultures. Specimens from blood, urine, nasopharynx, stool and bronchoalveolar lavage fluid were cultured for the presence of Ad. CMV-lacZ (by Xgal staining of 293 cell monolayers) and for adenoviruses by examining 293 monolayers for cytopathic effects. See Tables IX and X. Positive control data are also presented. All cultures yielded no growth except for one culture of bronchoalveolar lavage fluid obtained on day 3 after gene administration from an animal that received $1 \times 10^{10}$ pfu/ml dose.

Necropsy. Grossly, the lungs of all animals appeared normal with two exceptions. The animal that was sacrificed 21 days after receiving $1 \times 10^{10}$ pfu/ml virus had hemorrhagic and grayish patches located predominantly over the dorsal surfaces of the right upper, left upper and right lower lobes. Also, one animal had punctate green-black colored 1 mm spots scattered over the entire surface of both lungs.

Expression of β-galactosidase activity was examined using lung sections stained en bloc with Xgal. Alveolar tissue from the posterior segment of the left upper lobe of animals receiving $1 \times 10^{10}$ pfu/ml doses stained dark blue on day 3 or 4 (see FIG. 5). The animal receiving $1 \times 10^9$ pfu/ml had similar, but less intense staining on day 4. A few scattered areas of positively staining airway cells could be seen under the dissecting microscope from the animals receiving $1 \times 10^{10}$ pfu/ml on day 3 or 4. No staining was seen in any animal on day 21 or at lower viral doses. Xgal staining of frozen sections of lung tissue confirmed the conclusions made at the dissecting microscope level. (See FIG. 6).

Figure 12:
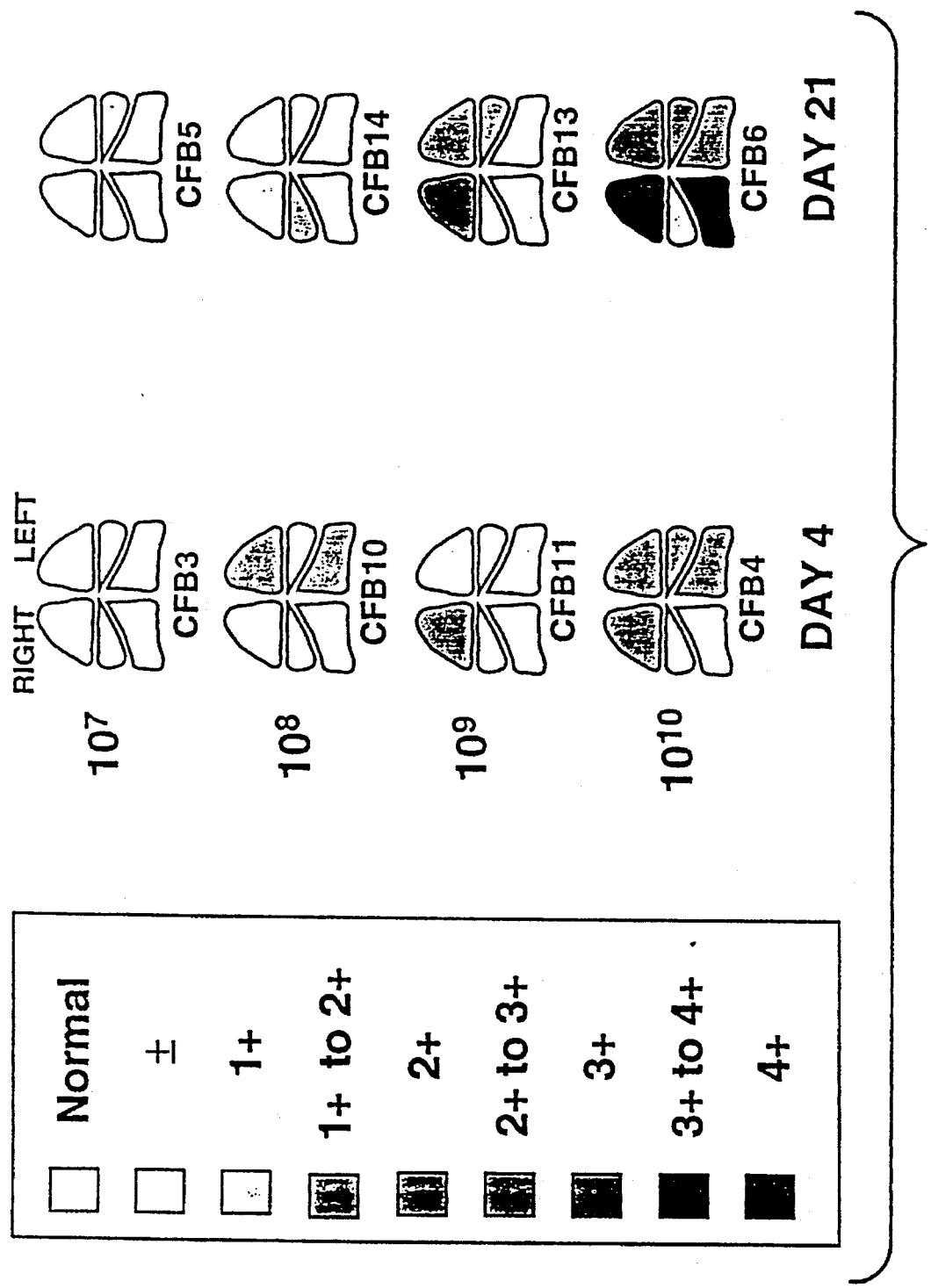
FIG. 12 is a schematic showing the location and extent of lymphocytic pneumonitis in the lungs of animals following gene administration.

Southern analysis was performed to determine the anatomical location, copy number and persistence of viral DNA. Total DNA was prepared from adjacent quadrants of the lung which were analyzed for transgene expression by histochemical and immunohistochemical techniques. In FIG. 12, each field (upper, middle, and lower) of the right and left lung is schematically represented for animals receiving $1 \times 10^7 - 10^{10}$pfu/ml viral doses and necropsied on days 4 and 21. The degree of inflammation depicted for each field represents an averaging of the level of inflammation seen on multiple (2 to 4) sections from each lobe. As shown in FIG. 12, CFTR recombinant adenoviral DNA was detectable only in the posterior segment of the upper right lobe and was confined to the area in which the Ad.CBCFTR. was instilled. Comparison of signals detected in lung DNA samples to standards of known quantities of purified Ad.CB-CFTR DNA gave an estimated number of viral DNA molecules per cellular genome at day 4 post-infection as follows: $1 \times 10^{10}$ pfu/ml-10 viral DNA molecules per cellular genome; $1 \times 10^9$pfu/ml-2 viral DNA molecules per cellular genome; $1 \times 10^8$ pfu/ml-0.2 viral DNA molecules per cellular genome; and $1 \times 10^7$ pfu/ml—undetectable levels of viral DNA. No adenoviral DNA was detectable in lung samples at any of the doses in animals necropsied at day 21 with the exception of the $1\times10^9$ pfu/ml dose in which trace amounts of DNA were visible on long exposures (less than 0.1 copies per cellular genome). In addition, no viral DNA was ever detected by Southern blot analysis in testes DNA harvested from animals necropsied at day 4 (all doses were analyzed).

To a varying degree and correlating with viral dose, the animals developed a lymphocytic perivascular infiltrate. At its mildest, small lymphocytic accumulations were seen surrounding small to medium-sized vessels within lung parenchyma. Increased numbers of alveolar macrophages were also present. With increasing severity of the abnormality, the lymphocytic infiltrate extended beyond the immediate perivascular area and into the alveolar interstitial spaces. Intra-alveolar lymphocytes occasionally accompanied the increased number of macrophages. In lung regions having a higher intensity of pneumonitis, the alveolar tissue was densely infiltrated with mononuclear cells and at its worse, intra-alveolar edema could be seen. FIG. 12 depicts the location and severity of the pneumonitis in the 8 animals on which detailed necropsies were performed. A grading system for the severity of inflammation was used to communicate the extent and location of inflammation: 1+, localized accumulations of lymphocytes in the immediate vicinity of small vessels with increase in intra-alveolar macrophages; 2+, inflammation extending out into neighboring alveolar septa; 3+, areas of confluent inflammation; and 4+, diffuse alveolar damage with intra-alveolar edema. Inflammation was absent or very mild in the lungs of all animals sacrificed on day 4 and in the lungs of animals receiving $1\times10^7$ and $10^8$ pfu/ml doses at day 21. Moderate to severe inflammation was seen in several areas of lung in the animal receiving $1\times10^{10}$ pfu/ml and in one area of lung in the animal receiving $1\times10^9$ pfu/ml dose. The inflammation was more likely present in regions of lung where virus was directly infused. However, it was also present outside these areas. This may represent spill over during instillation of virus since occasional Xgal positive cells were seen in frozen sections of lung tissue obtained from lung regions other than those directly infused. There seemed to be little if any difference in the degree of inflammation between the side receiving Ad.CMV-lacZ and the side receiving Ad.CB-CFTR. In scattered areas, eosinophils and rarely neutrophils could be seen. These cells were never the dominant type of inflammatory cell.

The majority of the inflammation was located within the distal lung parenchyma. There was no evidence of vessel wall necrosis although the lymphocytic infiltrate (1) seemed to arise around small vessels. The airways were relatively spared by the inflammation. Uncommonly, the well-demarcated bronchial associated lymphold aggregates would spread to infiltrate bronchial wall. In almost all instances, the epithelium remained intact with preservation of its pseudocolumnar pattern with abundant ciliated cells.

In three animals, all captured in the wild, scattered aggregates of macrophages were found diffusely throughout the lung parenchyma. The macrophages contained a dark greenish-black pigment that had within it refractlie material suggestive of silicates. In one of the three animals, a small number of lymphocytes surrounded the macrophage aggregates. The source of the material is unknown.

Non-pulmonary organs. Grossly and microscopically, the remaining organs contained no abnormalities referable to gene treatment. In one of the wild-caught animals, parasitic cysts were seen in skeletal muscle, in bone marrow, and in two areas within the liver. (Tables I–X).

It will be appreciated that the non-human primate studies described herein are representative of current human studies involving the second generation adenovirus vectors of the present invention.

SPECIFIC EXAMPLE 4—Human Protocol

The following is the protocol for human clinical trials for gene therapy using the vectors of the present invention containing an inserted CFTR gene. It will be appreciated that this protocol may also be used for gene therapy of genetic and epigenetic diseases other than cystic fibrosis.

Patient selection. Various criteria are used in evaluating cystic fibrosis patients for gene therapy using the adenovirus vectors of the present invention. The following criteria should be generally met by patients undergoing the clinical trials: (1) Proven diagnosis of cystic fibrosis. Proof will consist of documentation of both, sweat sodium or chloride greater than 60 mEq/l by the pilocarpine iontophoresis method or cystic fibrosis genotype and clinical manifestations of cystic fibrosis. (2) Age. Age greater than or equal to 18-years old. (3) Gender. Males or females may be used. Only patients who have no chance of procreating are entered into the study. Therefore, in the unlikely event that participation in the study induces mutations in the germline of the patient, these alterations will not be passed on to future generations. Males are eligible if they have documented azospermia. Over 95% of males with cystic fibrosis have congenital atrophy of the vas deferens and would thus fulfill this criterion. Females are eligible if they are documented to have had bilateral tubal ligations or a hysterectomy. (4) Severity of disease. To be eligible, a patient must be in adequate clinical condition to safely undergo the planned procedures, i.e. bronchoscopies. An acceptable reserve is defined as having a clinical condition such that the estimated 2-year survival is greater than 50%. Using the study of Kerem et al. (Kerem, E. et al., *N. Engl. J. Med.* 326:1187–1191 (1992)), patients are considered to have a greater than 50% chance of two year survival if they fulfill all of the following: a) $FEV_1$ greater than or equal to 30% predicted; b) $PaO_2$ greater than 55 mmHg while breathing room air; and c) $PaCO_2$ less than 50 mmHg while breathing room air. Although the disease severity criteria have been selected to avoid entering patients with near terminal pulmonary disease, the intent nevertheless is to study those with at least moderate to severe lung disease and a substantially shortened predicted survival. To select only those with an estimated chance of 5-year survival of less than or equal to 50%, the patient must fulfill the following criterion (Shwachman, *Am. J. Dis. Child* 96:6–15 (1958)): d) Shwachman-Kulczycki clinical score less than or equal to 50.

Patients are excluded from clinical trials if they exhibit:
(1) Risk of Complications. Conditions which would place them at increased risk for complications from participating in the study. These conditions include: a) Pneumothorax within the last 12 months; b) Insulin-dependent diabetes; c) Asthma or allergic bronchopulmonary aspergillosis requiring glucocorticoid therapy within the last two months; d) Sputum culture growing a pathogen which does not have in vitro sensitivity to at least two types of antibiotics which could be administered to the patient; e) History of major hemoptysis: Coughing up greater that 250 ml of blood within a 24 hour period during the last year; and f) Any medical condition or laboratory abnormality which, according to the opinion of the investigators, would place the patient at increased risk for complications.

(2) Evidence of Active Adenoviral Infection. The patient is carefully evaluated for evidence of active adenoviral infection. History and physical examination is used to identify clinical evidence for adenoviral syndromes such as coryza, pharyngitis, tonsillitis, bronchitis, pneumonia, conjunctivitis or diarrhea. A variety of specimens are evaluated for adenoviruses using culture techniques as well as immunofluorescent and enzyme-linked immunosorbent assays performed directly on the specimen. Evidence of active adenoviral infection at the time of therapy is a basis for exclusion. Another relevant question relates to previous exposure of the gene therapy recipient to Ad5 and similar serotypes based on adenovirus specific neutralizing antibodies. It is expected that virtually all adult patients will have been exposed to adenoviruses that confer humoral immunity to Ad5. This expectation is based on a large body of literature which indicate that the lower numbered adenoviruses Ad1, Ad2, Ad5, and Ad6 are endemic in most countries. In the United States, adenovirus-specific neutralizing antibodies are estimated to be present in 0% of individuals by the age of three. Sterner, *Acta Paediatr. Scand. Suppl.* 142-1 (1962); Hall, et al., *Am. J. Epichemiol.* 94:367 (1971); Foy, et al., "Viral Infections in Man," p. 5310 Ed. Evans AS Raven Press, NY (1976)). All patients enrolled in the protocol are evaluated for previous exposure to Ad5 and related types using a variety of serologic assays. It is expected that essentially every candidate patient will be seropositive. In fact, any patient who is not seropositive is excluded from the protocol. Existing humoral immunity to the virus is considered a safety feature which would prevent dissemination of the recombinant virus beyond the localized area of lung to which the recombinant virus is exposed.

(3) Drug therapy. Patients are excluded if they have been treated with systemic glucocorticoids within two months prior to initiation of the study.

(4) Inability to comply with protocol. Patients are excluded if, in the opinion of the investigators, the patient has characteristics which would make compliance with the protocol unlikely, e.g. drug abuse, alcoholism, psychiatric instability, inadequate motivation.

(5) Participation in Other Studies. Patients are excluded if they have participated in another investigational therapeutic study within the previous 90 days.

Patient evaluation. The following evaluations are performed at various times throughout the study:

(1) History and physical examination. A history relevant to the manifestations of both cystic fibrosis and unrelated diseases is taken. A full review of systems, medication usage, and drug allergy history is obtained.

(2) Clinical laboratory evaluations: a) Blood: hemoglobin, hematocrit, white blood cell count, white blood cell differential count, platelet count, Westergren sedimentation rate, serum electrolytes (sodium, potassium, chloride, bicarbonate), BUN, creatinine, glucose, uric acid, total protein, albumin, calcium, phosphate, total bilirubin, conjugated bilirubin, AST, ALT, alkaline phosphatase, LDH; b) urine analysis: qualitative protein, blood, glucose, ketones, pH and microscopic examination.

(3) Pulmonary function tests. Testing should meet the standards set by the American Thoracic Society (1987a, 1987b): a) spirometry using the normal predicted values of Crapo et al. (1981); b) absolute lung volumes (total lung capacity, thoracic gas volume, residual volume); and c) diffusion capacity, single breath.

(4) Arterial blood gases and pulse oximetry—while breathing room air.

(5) Electrocardiogram (12-lead).

(6) Postero-anterior and lateral chest X-ray.

(7) Thin-cut computerized tomography of the chest.

(8) Aerobic bacterial culture of sputum with antibiotic sensitivities.

(9) Shwachman-Kulczycki score calculation.

(10) Sperm count for males. If a sperm count has not been done previously with the results documented, semen analysis is performed by the Department of Urology, University of Michigan Center.

(11) Bronchoscopy. Patients are allowed nothing by mouth for 6 hours prior to the procedure. They are premedicated with 0.2 mg glycopyrrolate and 50 mg meperidine intravenously 30 minutes before bronchoscopy. Electrocardiogram, pulse rate, and pulse oximetry is continuously monitored. Blood pressure is monitored every 5 minutes by an automated noninvasive system. Viscous lidocaine 2% (30 ml) is gargled and expectorated. Lidocaine 4% is sprayed onto the posterior pharynx and larynx by a hand held atomizer. The bronchoscope is introduced through the nose in patients without nasal obstruction or evidence of polyps. If the nasal approach cannot be used, the bronchoscope is introduced orally. In patients undergoing bronchoscopy by the nasal route, oxymetazoline hydrochloride 0.05% is applied topically to the mucosa of one nasal passage with a cotton swab. Lidocaine jelly 2% is instilled into the same nasal passage. Supplemental oxygen by cannula is administered at the mouth at 6 liters/minute. Midazolam is administered intravenously in 1 mg boluses over 15 seconds every 5 minutes until the patient is relaxed but still arousable by verbal stimuli. Additional midazolam is administered in 1 mg boluses up to every 15 minutes to maintain this level of sedation. A flexible fiberoptic bronchoscope is introduced transnassally. Lidocaine 2% is injected through the bronchoscope to anesthetize the larynx and airways as needed.

(12) Bronchoalveolar lavage. 50 ml aliquots of normal saline is injected through the bronchoscope that has been gently wedged into segmental bronchus. The lavagate is aspirated into a suction trap. The procedure is repeated until three aliquots have been administered and recovered.

(13) Mucosal epithelial cell brushing. A sleeved catheter with internal brush is introduced into the bronchus (Kelsen, *Am. J. Respir. Cell Mol. Bio.* 17:66–72 (1992)). The brush is rubbed against the epithelial mucosa and the adherent cells removed by agitating the brush in sterile medium.

(14) Transbronchial biopsies. A biopsy forceps is introduced into the bronchus and under fluoroscopic guidance six pieces of tissue are taken.

Clinical protocol. The following is the protocol for screening evaluation of the patient: Screening evaluation must be performed within four weeks of gene therapy. Written informed consent should be obtained prior to participation in the screening evaluation. Information obtained during screening is: history and physical exam; clinical laboratory blood tests; sperm count on males; pulmonary function tests; pulse oximetry and arterial blood gas; electrocardiography (12-lead); PA and lateral chest X-ray; thin-cut CT scan; sputum culture with antibiotic sensitivities; and Shwachman-Kulczycki Score calculation.

The following is the protocol for treatment of the patient prior to transfection: Beginning 2 weeks prior to transfection, the patient begins an intensified treatment protocol to reduce respiratory infection and maximize overall condition. For two weeks, the patient receives two anti-Pseudomonal antibiotics to which their cultured organism is sensitive. Twice a day postural drainage and percussion is performed. The patient continues on the remainder of their chronic treatment regimen. This phase is accomplished either as an inpatient or outpatient. During the subsequent studies, the patient continues on their previously prescribed medical program. This includes continuation of any oral antibiotics, pancreatic enzymes, theophylline, and vitamin supplements. Aerosolized bronchodilators and antibiotics are continued.

The following is the protocol for selection of the lung segment for transfection: The chest X-ray and thin cut CT scan is used to select an anatomical pulmonary segment that: a) has a degree of disease involvement average for that patient; and b) is in a location such that the patient can be positioned at bronchoscopy so that the segmental bronchus is gravitationally dependent.

The following is the transfection procedure: The patient is prepared for bronchoscopy as indicated above. The bronchoscope is introduced and advanced to the orifice of the segment chosen for the transfection. Secretions present within the segmental bronchus is aspirated through the bronchoscope. Transepithelial electrical potential difference is measured in the segment selected for transfection and in the segmental bronchus that is located in the same position in the opposite lung. A balloon catheter is introduced through the bronchoscope channel and advanced one centimeter into the orifice of the lung segment to be transfected. The balloon is inflated under direct vision until the orifice is minimally occluded. Fifty ml of virus at a concentration of $1 \times 10^{10}$ pfu/ml in normal saline at 37° C. is instilled through the balloon catheter. The catheter with balloon inflated is held in place for 30 minutes, after which time any remaining fluid is aspirated. The balloon is deflated and the catheter and bronchoscope removed.

A single dose of virus, $1 \times 10^{10}$ pfu/ml in a total volume of 50 ml is used. This particular dose was selected based on experience with human CF xenografts. Englehardt et al., *Nature Genetics* 4:27–34 (1993). It has been found that increasing the concentration of virus above $1 \times 10^{10}$ pfu/ml does not appreciably increase the efficiency of gene transfer. Lower doses are not used in this protocol because of the very real possibility that the efficiency of gene transfer would be insignificant.

The following is the protocol for post bronchoscopy monitoring: Vital signs including blood pressure, pulse, temperature, and respiratory rate are measured and recorded every five minutes for the first hour, every 15 minutes for the next two hours, every one hour for the next six hours, and every two hours for the next 15 hours, and every four hours for the rest of the week post-transfection. Continuous electrocardiographic and pulse oximetry are measured for the first 24 hours. The clinical laboratory blood tests that are listed above, pulse oximetry, and PA and lateral chest X-rays are performed daily for the first week, twice a week for the second week, and weekly thereafter for six weeks. Thin-cut CT scans are performed on the day prior to the follow-up bronchoscopy.

Following the administration of virus, the patients are kept in an isolation room with full respiratory precautions. The isolation room is a negative pressure room in which the air is filtered and delivered outside. Anyone entering the room wears a gown, mask, eye protection, and gloves. The patient is in isolation for at least 10 days after initiation of therapy. While in the hospital the patient has his or her sputum, nasal swab, urine and stool analyzed for replication competent adenoviruses of any serotype using standard adenovirus assays. These samples are also evaluated for CFTR recombinant virus using a PCR assay, known in the art. In the unlikely event that the patient continues to shed recombinant CFTR adenovirus in the airway, he or she is kept in the hospital for a longer period of time.

The following is a schedule for post-transfection bronchoscopies: Day 4 (transfection on day 0); Day 42; and Day 90.

The following samples and measurements are obtained during post-transfection bronchoscopies: a) transepithelial electrical potential difference at four sites within the transfected segment and within the segmental bronchus of its mirror image in the opposite lung: b) bronchoalveolar lavage of transfected segment and its mirror image in the opposite lung; c) six cytological brushings of alveolar surface from the transfected segment; and d) six transbronchial biopsies from the transfected segment.

Evaluation of therapy. The patient is carefully monitored for toxicity, immunological response to CFTR protein or adenoviral proteins and efficiency and stability of gene transfer. The following protocol is followed:

(1) Toxicity. Ser. examinations to include PFT's, blood chemistry, hematology and cultures for adenovirus is performed. Bronchoalveolar lavage fluid obtained during each follow-up bronchoscopy is carefully analyzed for wild type and recombinant virus.

(2) Immunological responses. A major aspect of this protocol is to evaluate the serological response of the patient. The patient's serum and bronchoalveolar lavage fluid is evaluated for serological responses to wild type CFTR and adenoviral proteins.

(3) Efficiency and stability of gene transfer. Bronchoscopy performed following gene transfer provides an opportunity to assess gene transfer and CFTR expression. Transepithelial electrical potential differences is performed at four sites within the transfected segment. Superficial airway epithelial cells are harvested by brushing and plated in culture. These cells are analyzed for CFTR protein and adenoviral protein expression using immunocytochemistry. Functional correction is assessed in cultured cells using the functional assay described. Transbronchial biopsy material, containing airway and airspace tissue, is analyzed for CFTR expression by immunocytochemistry and in situ hybridization.

SPECIFIC EXAMPLE 5—Mutation and Selection Schemes

In addition to utilization of published temperature sensitive (ts) mutants, novel recombinant vectors are generated carrying ts mutations in the adenoviral genes E2, E4, L1, L2, L3, L4 and L5. Novel ts mutant adenoviral strains (potentially applying to all adenoviral serotypes including Ad2 through Ad41) are isolated as previously described. See Ensinger et al., *J. Virol.* 10:328–339 (1972). Stocks of wild type adenoviral DNA and/or virus are mutagenized by three different methods: 1) nitrous acid, 2) hydroxylamine, and 3) nitrosoguanidine. 293 cells are transfected or infected with mutated DNA or virus. Temperature sensitive mutant strains are isolated by a plaque enlargement technique in which mutagenized stocks are plaqued by agar overlay at 32° C. At day 14 post-infection plaques are stained in Neutral Red for 24 to 48 hr at 32° C. (permissive temperature) and circumference of plaques outlined. Plates are then shifted to 39.5°

C. (non-permissive temperature) for 48 hr and only plaques which do not enlarge are picked for screening for their ability to cause complete temperature-sensitive CPE on HeLa cells. The ts mutants thus derived are classified by functional complementation of viral strains carrying known mutations. Once potentially useful ts mutants have been identified, they are cloned by homologous recombination into recombinant vectors (as described above) to give new ts recombinant adenoviral stocks. In addition, recombinant adenovirus containing multiple ts mutations may be generated.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the specification and following claims.

All publications and applications cited herein are incorporated by reference.

TABLE I

Animal Identification and Viral Doses

| Study # | Animal ID | Dose pfu/ml | Species | Sex | Wt lbs | Date of Birth (Age) |
|---|---|---|---|---|---|---|
| I | CFB1 | 1.0E+10 | P. anubis | M | 71.5 | Unknown (approx. 12 yr) |
| II | CFB2 | 1.0E+10 | P. cynocephalus/anubis | M | 71.5 | Unknown (approx. 12 yr) |
| III | CFB3 | 1.0E+07 | P. papio | M | 23 | 10/01/88 |
| | CFB5 | 1.0E+07 | P. papio | M | 26.5 | 09/12/88 |
| | CFB7 | 1.0E+07 | P. papio | M | 25 | 12/31/87 |
| | CFB10 | 1.0E+08 | P. papio | M | 13.5 | 09/11/90 |
| | CFB14 | 1.0E+08 | P. papio | M | 19.2 | Unknown (2–5 yr) |
| | CFB16 | 1.0E+08 | P. papio | M | 20.3 | Unknown (2–5 yr) |
| | CFB11 | 1.0E+09 | P. papio | M | 14.7 | 10/25/90 |
| | CFB13 | 1.0E+09 | P. papio | M | 19.4 | Unknown (2–5 yr) |
| | CFB15 | 1.0E+09 | P. papio | M | 20.5 | Unknown (2–5 yr) |
| | CFB4 | 1.0E+10 | P. papio | M | 17 | Unknown (2–5 yr) |
| | CFB6 | 1.0E+10 | P. papio | M | 30 | Unknown (2–5 yr) |
| | CFB8 | 1.0E+10 | P. papio | M | 23 | Unknown (2–5 yr) |

TABLE IIa

Hematology for Baboon Toxicity Studies

| | HGB | HCT | PLATELETS | WBC | SEGS |
|---|---|---|---|---|---|
| NORMAL ADULT BABOON | 12.1–15.3 | 38–48 | 205–451 | 5.9–20.8 | 22–85 |
| NORMAL JUVENILE BABOON | 8.7–13.9 | 31–43 | 225–544 | 3.3–19.0 | 23–78 |

| | STABS | LYMPHS | MONO | EOSIN | BASO |
|---|---|---|---|---|---|
| NORMAL ADULT BABOON | 0–4 | 12.0–75 | 0–4 | 0–5 | 0–1 |
| NORMAL JUVENILE BABOON | 0–6 | 14–76 | 0–3 | 0–8 | 0–1 |

| | PTT | PT | INR |
|---|---|---|---|
| NORMAL ADULT BABOON | N/A | N/A | N/A |
| NORMAL JUVENILE BABOON | N/A | N/A | N/A |

TABLE IIb

Hematology for Baboon Toxicity Studies - Study I

| VIRUS | NECROPSY | ANIMAL | DATE | DAY | HGB | HCT | PLATELETS | WBC |
|---|---|---|---|---|---|---|---|---|
| 1.0E + 10 | 4 DAY | CFB1 | ND | | | | | |

| VIRUS | NECROPSY | ANIMAL | DATE | DAY | SEGS | STBS | LYMPHS | MONO |
|---|---|---|---|---|---|---|---|---|
| 1.0E + 10 | 4 DAY | CFB1 | ND | | | | | |

| VIRUS | NECROPSY | ANIMAL | DATE | DAY | EOSIN | BASO | PTT | PT |
|---|---|---|---|---|---|---|---|---|
| 1.0E + 10 | 4 DAY | CFB1 | ND | | | | | |

TABLE IIb-continued

Hematology for Baboon Toxicity Studies - Study I

| VIRUS | NECROPSY | ANIMAL | DATE | DAY | INR |
|---|---|---|---|---|---|
| 1.0E + 10 | 4 DAY | CFB1 | ND | | |

TABLE IIc

Hematology for Baboooon Toxicity Studies - Study II

| VIRUS | NECROPSY | ANIMAL | DATE | DAY | HGB | HCT | PLATELETS | WBC |
|---|---|---|---|---|---|---|---|---|
| 1.0E + 10 | LONG-TERM | CFB2 | 11/06/92 | −3 | 14.0 | 43.2 | 273 | 8.3 |
| | | | 11/09/92 | 0 | 13.9 | 40.9 | 296 | 7.1 |
| | | | 11/12/92 | 3 | 13.8 | 40.6 | 256 | 5.7 |
| | | | 11/23/92 | 14 | 14.2 | 41.5 | 428 | 9.8 |
| | | | 11/30/92 | 21 | 13.8 | 42.4 | 375 | 10.1 |
| | | | 01/21/93 | 73 | 14.1 | 42.2 | 321 | 12.0 |
| | | | 01/25/93 | 77 | 13.8 | 40.8 | 338 | 8.7 |
| | | | 02/19/93 | 102 | 14.2 | 42.4 | 300 | 7.3 |
| | | | 03/05/93 | 116 | 13.8 | 41.1 | 287 | 5.5 |
| | | | 04/10/93 | 152 | 10.0 | 41.6 | 333 | 10.0 |

| VIRUS | NECROPSY | ANIMAL | DATE | DAY | SEGS | STABS | LYMPHS | MONO |
|---|---|---|---|---|---|---|---|---|
| 1.0E + 10 | LONG-TERM | CFB2 | 11/06/92 | −3 | 62 | 2 | 33 | 2 |
| | | | 11/09/92 | 0 | 74 | — | 19 | 5 |
| | | | 11/12/92 | 3 | 63 | 0 | 25 | 11 |
| | | | 11/23/92 | 14 | 66 | — | 31 | 1 |
| | | | 11/30/92 | 21 | 60 | — | 31 | 3 |
| | | | 01/21/93 | 73 | 80 | — | 18 | 1 |
| | | | 01/25/93 | 77 | 71 | — | 24 | 4 |
| | | | 02/19/93 | 102 | 61 | — | 33 | 5 |
| | | | 03/05/93 | 116 | 58 | — | 36 | 5 |
| | | | 04/10/93 | 152 | 77 | — | 20 | 3 |

| VIRUS | NECROPSY | ANIMAL | DATE | DAY | EOSIN | BASO | PTT | PT |
|---|---|---|---|---|---|---|---|---|
| 1.0E + 10 | LONG-TERM | CFB2 | 11/06/92 | −3 | 1 | 0 | ND | ND |
| | | | 11/09/92 | 0 | 1 | 2 | ND | ND |
| | | | 11/12/92 | 3 | 1 | 0 | 27.8 | 12.0 |
| | | | 11/23/92 | 14 | 1 | 1 | 29.1 | 11.8 |
| | | | 11/30/92 | 21 | 2 | 4 | 27.0 | 12.5 |
| | | | 01/21/93 | 73 | 0 | 0 | ND | ND |
| | | | 01/25/93 | 77 | 1 | 0 | ND | ND |
| | | | 02/19/93 | 102 | 1 | 0 | ND | ND |
| | | | 03/05/93 | 116 | 1 | 0 | 25.0 | 12.2 |
| | | | 04/10/93 | 152 | 1 | 0 | | |

| VIRUS | NECROPSY | ANIMAL | DATE | DAY | INR |
|---|---|---|---|---|---|
| 1.0E + 10 | LONG-TERM | CFB2 | 11/06/92 | −3 | ND |
| | | | 11/09/92 | 0 | ND |
| | | | 11/12/92 | 3 | 0.9 |
| | | | 11/23/92 | 14 | 0.9 |
| | | | 11/30/92 | 21 | 1.0 |
| | | | 01/21/93 | 73 | ND |
| | | | 01/25/93 | 77 | ND |
| | | | 02/19/93 | 102 | ND |
| | | | 03/05/93 | 116 | 0.9 |
| | | | 04/10/93 | 152 | |

TABLE IId

Hematology for Baboooon Toxicity Studies - Study III

| VIRUS | NECROPSY | ANIMAL | DATE | DAY | HGB | HCT | PLATELETS | WBC |
|---|---|---|---|---|---|---|---|---|
| 1.0E + 07 | 4 DAY | CFB3 | 01/18/93 | 0 | 13.3 | 38.9 | 298 | 6.7 |
| | | | 01/22/93 | 4 | 12.9 | 37.8 | 313 | 5.6 |
| | 21 DAY | CFB5 | 01/18/93 | 0 | 13.5 | 40.2 | 404 | 11.6 |
| | | | 01/22/93 | 4 | 12.5 | 36.0 | 444 | 8.1 |
| | | | 02/02/93 | 15 | 12.8 | 38.2 | 421 | 12.1 |
| | | | 02/08/93 | 21 | 12.5 | 37.8 | 442 | 6.6 |
| | LONG-TERM | CFB7 | 01/18/93 | 0 | 13.6 | 39.5 | 256 | 10.3 |
| | | | 01/22/93 | 4 | 12.7 | 38.1 | 238 | 6.7 |

TABLE IId-continued

Hematology for Babooon Toxicity Studies - Study III

| | | | 02/02/93 | 15 | 13.2 | 39.7 | 322 | 8.0 |
|---|---|---|---|---|---|---|---|---|
| | | | 02/08/93 | 21 | 12.7 | 38.6 | 319 | 7.2 |
| | | | 03/10/93 | 51 | 13.8 | 41.2 | 272 | 6.3 |
| | | | 04/10/93 | 82 | 13.9 | 41.2 | 324 | 5.9 |

| VIRUS | NECROPSY | ANIMAL | DATE | DAY | SEGS | STABS | LYMPHS | MONO |
|---|---|---|---|---|---|---|---|---|
| 1.0E + 07 | 4 DAY | CFB3 | 01/18/93 | 0 | 46 | — | 45 | 4 |
| | | | 01/22/93 | 4 | 53 | 1 | 41 | 2 |
| | 21 DAY | CFB5 | 01/18/93 | 0 | 74 | 0 | 26 | 0 |
| | | | 01/22/93 | 4 | 58 | — | 38 | 2 |
| | | | 02/02/93 | 15 | 79 | — | 19 | 1 |
| | | | 02/08/93 | 21 | 35 | 0 | 60 | 2 |
| | LONG-TERM | CFB7 | 01/18/93 | 0 | 67 | — | 28 | 4 |
| | | | 01/22/93 | 4 | 52 | — | 40 | 6 |
| | | | 02/02/93 | 15 | 50 | 3 | 38 | 8 |
| | | | 02/08/93 | 21 | 55 | 0 | 43 | 2 |
| | | | 03/10/93 | 51 | 49 | 1 | 45 | 4 |
| | | | 04/10/93 | 82 | 28 | | 53 | 16 |

| VIRUS | NECROPSY | ANIMAL | DATE | DAY | EOSIN | BASO | PTT | PT |
|---|---|---|---|---|---|---|---|---|
| 1.0E + 07 | 4 DAY | CFB3 | 01/18/93 | 0 | 3 | 3 | ND | ND |
| | | | 01/22/93 | 4 | 1 | 0 | 23.8 | 13.2 |
| | 21 DAY | CFB5 | 01/18/93 | 0 | 0 | 0 | 23.0 | 13.4 |
| | | | 01/22/93 | 4 | 2 | 0 | 23.8 | 12.8 |
| | | | 02/02/93 | 15 | 1 | 0 | 25.1 | 12.9 |
| | | | 02/08/93 | 21 | 3 | 0 | 22.9 | 12.4 |
| | LONG-TERM | CFB7 | 01/18/93 | 0 | 1 | 0 | 24.7 | 13.2 |
| | | | 01/22/93 | 4 | 2 | 0 | 23.1 | 12.7 |
| | | | 02/02/93 | 15 | 1 | 0 | 27.0 | 13.0 |
| | | | 02/08/93 | 21 | 0 | 0 | 24.6 | 12.9 |
| | | | 03/10/93 | 51 | 1 | 0 | ND | ND |
| | | | 04/10/93 | 82 | 3 | 0 | | |

| VIRUS | NECROPSY | ANIMAL | DATE | DAY | INR |
|---|---|---|---|---|---|
| 1.0E + 07 | 4 DAY | CFB3 | 01/18/93 | 0 | ND |
| | | | 01/22/93 | 4 | 1.1 |
| | 21 DAY | CFB5 | 01/18/93 | 0 | 1.1 |
| | | | 01/22/93 | 4 | 1.0 |
| | | | 02/02/93 | 15 | 1.1 |
| | | | 02/08/93 | 21 | 1.0 |
| | LONG-TERM | CFB7 | 01/18/93 | 0 | 1.1 |
| | | | 01/22/93 | 4 | 1.0 |
| | | | 02/02/93 | 15 | 1.1 |
| | | | 02/08/93 | 21 | 1.1 |
| | | | 03/10/93 | 51 | ND |
| | | | 04/10/93 | 82 | |

TABLE IIe

Hematology for Babooon Toxicity Studies - Study III

| VIRUS | NECROPSY | ANIMAL | DATE | DAY | HGB | HCT | PLATELETS | WBC | SEGS |
|---|---|---|---|---|---|---|---|---|---|
| 1.0E + 08 | 4 DAY | CFB10 | 02/03/93 | −13 | 13.0 | 39.5 | 244 | 14.3 | 39 |
| | | | 02/10/93 | −6 | 12.4 | 37.3 | 295 | 10.1 | 44 |
| | | | 02/16/93 | 0 | 12.5 | 37.7 | 236 | 6.9 | 27 |
| | | | 02/20/93 | 4 | 12.5 | 37.4 | 280 | 5.6 | 22 |
| | 21 DAY | CFB14 | 01/29/93 | −18 | 12.0 | 35.5 | 338 | 5.8 | 53 |
| | | | 02/16/93 | 0 | 12.3 | 36.3 | CLUMPED | 9.5 | 63 |
| | | | 02/20/93 | 4 | 12.1 | 35.9 | 251 | 6.8 | 52 |
| | | | 03/02/93 | 14 | 12.5 | 38.0 | CLUMPED | 13.7 | 63 |
| | | | 03/09/93 | 21 | 12.6 | 37.6 | CLUMPED | 9.9 | 68 |
| | LONG-TERM | CFB16 | 01/29/93 | −18 | 12.2 | 36.7 | CLUMPED | 7.6 | 42 |
| | | | 02/16/93 | 0 | 12.7 | 38.9 | CLUMPED | 10.0 | 52 |
| | | | 02/20/93 | 4 | 11.7 | 35.1 | 268 | 5.6 | 19 |
| | | | 03/02/93 | 14 | 11.0 | 33.6 | 240 | 6.8 | 46 |
| | | | 03/09/93 | 21 | 11.1 | 33.1 | 211 | 8.0 | 45 |
| | | | 04/10/93 | 53 | 11.7 | 35.0 | 311 | 9.5 | 42 |

TABLE IIe-continued

Hematology for Babooon Toxicity Studies - Study III

| VIRUS | NECROPSY | ANIMAL | DATE | DAY | STABS | LYMPHS | MONO | EOSIN | BASO |
|---|---|---|---|---|---|---|---|---|---|
| 1.0E + 08 | 4 DAY | CFB10 | 02/03/93 | −13 | 0 | 55 | 4 | 2 | 0 |
| | | | 02/10/93 | −6 | 1 | 49 | 3 | 3 | 0 |
| | | | 02/16/93 | 0 | 0 | 68 | 2 | 3 | 0 |
| | | | 02/20/93 | 4 | 0 | 69 | 4 | 5 | 0 |
| | 21 DAY | CFB14 | 01/39/93 | −18 | — | 42 | 4 | 1 | 0 |
| | | | 02/16/93 | 0 | 0 | 36 | 1 | 0 | 0 |
| | | | 02/20/93 | 4 | 0 | 45 | 2 | 0 | 1 |
| | | | 03/02/93 | 14 | 0 | 33 | 3 | 1 | 0 |
| | | | 03/09/93 | 21 | 1 | 29 | 1 | 0 | 0 |
| | LONG-TERM | CFB16 | 01/29/93 | −18 | 0 | 47 | 3 | 3 | 0 |
| | | | 02/16/93 | 0 | 0 | 47 | 1 | 0 | 0 |
| | | | 02/20/93 | 4 | 0 | 74 | 4 | 3 | 0 |
| | | | 03/02/93 | 14 | 4 | 45 | 5 | 0 | 0 |
| | | | 03/09/93 | 21 | 0 | 47 | 7 | 1 | 0 |
| | | | 04/10/93 | 53 | 54 | 4 | 0 | 0 | 0 |

| VIRUS | NECROPSY | ANIMAL | DATE | DAY | PTT | PT | INR |
|---|---|---|---|---|---|---|---|
| 1.0E + 08 | 4 DAY | CFB10 | 02/03/93 | −13 | ND | ND | ND |
| | | | 02/10/93 | −6 | ND | ND | ND |
| | | | 02/16/93 | 0 | 24.7 | 13.0 | 1.1 |
| | | | 02/20/93 | 4 | 24.0 | 13.1 | 1.0 |
| | 21 DAY | CFB14 | 01/29/93 | −18 | ND | ND | ND |
| | | | 02/16/93 | 0 | 25.0 | 12.5 | 1.0 |
| | | | 02/20/93 | 4 | 24.8 | 12.1 | 0.9 |
| | | | 03/02/93 | 14 | 24.5 | 12.2 | 1.0 |
| | | | 03/09/93 | 21 | 25.1 | 12.1 | 0.9 |
| | LONG-TERM | CFB16 | 01/29/93 | −18 | ND | ND | ND |
| | | | 02/16/93 | 0 | 22.0 | 12.1 | 0.9 |
| | | | 02/20/93 | 4 | 22.6 | 12.2 | 1.0 |
| | | | 03/02/93 | 14 | 22.3 | 12.5 | 1.0 |
| | | | 03/09/93 | 21 | 22.4 | 11.9 | 0.9 |
| | | | 04/10/93 | 53 | | | |

TABLE IIf

Hematology for Babooon Toxicity Studies - Study III

| VIRUS | NECROPSY | ANIMAL | DATE | DAY | HGB | HCT | PLATELETS | WBC | SEGS |
|---|---|---|---|---|---|---|---|---|---|
| 1.0E + 09 | 4 DAY | CFB11 | 02/03/93 | −13 | 12.6 | 38.5 | 337 | 6.1 | 69 |
| | | | 02/16/93 | 0 | 12.9 | 38.5 | 313 | 5.5 | 54 |
| | | | 02/20/93 | 4 | 12.4 | 37.6 | 315 | 4.9 | 58 |
| | 21 DAY | CFB13 | 01/29/93 | −18 | 12.3 | 36.6 | 447 | 5.5 | 39 |
| | | | 02/16/93 | 0 | 12.8 | 38.3 | 269 | 6.1/40 | |
| | | | 02/20/93 | 4 | 12.8 | 38.3 | 403 | 5.9 | 61 |
| | | | 03/02/93 | 14 | 13.1 | 39.5 | 385 | 6.7 | 52 |
| | | | 03/09/93 | 21 | 12.9 | 38.4 | 305 | 6.1/46 | |
| | LONG-TERM | CFB15 | 02/03/93 | −13 | 13.0 | 39.2 | 332 | 4.4 | 51 |
| | | | 02/16/93 | 0 | 12.9 | 38.8 | 322 | 8.7 | 78 |
| | | | 02/20/93 | 4 | 12.2 | 37.7 | 352 | 5.5 | 53 |
| | | | 03/02/93 | 14 | 12.1 | 37.2 | 334 | 9.9 | 73 |
| | | | 03/09/93 | 21 | 12.6 | 38.2 | 224 | 7.3 | 56 |
| | | | 04/10/93 | 53 | 13.2 | 39.5 | 259 | 5.7 | 48 |

| VIRUS | NECROPSY | ANIMAL | DATE | DAY | STABS | LYMPHS | MONO | EOSIN | BASO |
|---|---|---|---|---|---|---|---|---|---|
| 1.0E + 09 | 4 DAY | CFB11 | 02/03/93 | −13 | — | 28 | 2 | 0 | '1 |
| | | | 02/16/93 | 0 | — | 44 | 1 | 1 | 0 |
| | | | 02/20/93 | 4 | — | 38 | 3 | 1 | 1 |
| | 21 DAY | CFB13 | 01/29/93 | −18 | 0 | 51 | 7 | 3 | 0 |
| | | | 02/16/93 | 0 | 0 | 50 | 1 | 0 | 0 |
| | | | 02/20/93 | 4 | 0 | 34 | 5 | 0 | 0 |
| | | | 03/02/93 | 14 | 0 | 44 | 2 | 1 | 1 |
| | | | 03/09/93 | 21 | 0 | 48 | 4 | 2 | 0 |
| 1.0E + 09 | LONG-TERM | CFB15 | 02/03/93 | −13 | — | 41 | 5 | 2 | 1 |
| | | | 02/16/93 | 0 | 0 | 17 | 4 | 1 | 0 |
| | | | 02/20/93 | 4 | 0 | 38 | 7 | 1 | 1 |
| | | | 03/02/93 | 14 | — | 20 | 6 | 1 | 0 |
| | | | 03/09/93 | 21 | 2 | 34 | 3 | 4 | 1 |
| | | | 04/10/93 | 53 | | 44 | 4 | 3 | 1 |

TABLE IIf-continued

Hematology for Babooon Toxicity Studies - Study III

| VIRUS | NECROPSY | ANIMAL | DATE | DAY | PTT | PT | INR |
|---|---|---|---|---|---|---|---|
| 1.0E + 09 | 4 DAY | | 02/03/93 | −13 | ND | ND | ND |
| | | | 02/16/93 | 0 | 25.4 | 12.6 | 1.0 |
| | | | 02/20/93 | 4 | 24.2 | 12.3 | 1.0 |
| | 21 DAY | CFB13 | 01/29/93 | −18 | ND | ND | ND |
| | | | 02/16/93 | 0 | NA | 13.9 | 1.2 |
| | | | 02/20/93 | 4 | 25.6 | 12.3 | 1.0 |
| | | | 03/02/93 | 14 | 25.3 | 12.4 | 1.0 |
| | | | 03/09/93 | 21 | 23.8 | 12.0 | 0.9 |
| | LONG-TERM | CFB15 | 02/03/93 | −13 | ND | ND | ND |
| | | | 02/16/93 | 0 | 23.1 | 13.1 | 1.1 |
| | | | 02/20/93 | 4 | 24.1 | 13.1 | 1.1 |
| | | | 03/02/93 | 14 | 24.2 | 13.7 | 1.2 |
| | | | 03/09/93 | 21 | 22.8 | 12.6 | 1.0 |
| | | | 04/10/93 | 53 | | | |

TABLE IIg

Hematology for Babooon Toxicity Studies - Study III

| VIRUS | NECROPSY | ANIMAL | DATE | DAY | HGB | HCT | PLATELETS | WBC | SEGS |
|---|---|---|---|---|---|---|---|---|---|
| 1.0E + 10 | 4 DAY | CFB4 | 01/18/93 | 0 | 13.4 | 39.3 | 342 | 9.8 | 29 |
| | | | 01/22/93 | 4 | 12.5 | 36.8 | 338 | 8.9 | 25 |
| | 21 DAY | CFB6 | 01/18/93 | 0 | 12.8 | 37.7 | 364 | 8.8 | 67 |
| | | | 01/22/93 | 4 | 12.8 | 38.1 | 341 | 8.2 | 60 |
| | | | 02/02/93 | 15 | 12.0 | 36.1 | 343 | 8.9 | 63 |
| | | | 02/08/93 | 21 | 12.3 | 37.6 | 425 | 9.6 | 74 |
| | LONG-TERM | CFB8 | 01/18/93 | 0 | 12.9 | 39.4 | 372 | 8.2 | 48 |
| | | | 01/22/93 | 4 | 12.6 | 37.8 | 347 | 6.3 | 25 |
| | | | 02/02/93 | 15 | 13.2 | 40.3 | 387 | 10.6 | 63 |
| | | | 02/08/93 | 21 | 12.9 | 39.7 | 462 | 9.8 | 50 |
| | | | 03/10/93 | 51 | 12.7 | 38.6 | 381 | 10.3 | 64 |
| | | | 04/10/93 | 82 | 13.2 | 39.9 | 429 | 9.1 | 45 |

| VIRUS | NECROPSY | ANIMAL | DATE | DAY | STABS | LYMPHS | MONO | EOSIN | BASO |
|---|---|---|---|---|---|---|---|---|---|
| 1.0E + 10 | 4 DAY | CFB4 | 01/18/93 | 0 | 0 | 67 | 3 | 1 | 0 |
| | | | 01/22/93 | 4 | 0 | 71 | 4 | 0 | 0 |
| | 21 DAY | CFB6 | 01/18/93 | 0 | — | 28 | 4 | 1 | 0 |
| | | | 01/22/93 | 4 | — | 36 | 2 | 1 | 1 |
| | | | 02/02/93 | 15 | 6 | 25 | 6 | 0 | 0 |
| | | | 02/08/93 | 21 | — | 24 | 2 | 1 | 0 |
| | LONG-TERM | CFB8 | 01/18/93 | 0 | 0 | 48 | 1 | 2 | 1 |
| | | | 01/22/93 | 4 | 0 | 68 | 3 | 3 | 0 |
| | | | 02/02/93 | 15 | — | 32 | 2 | 2 | 1 |
| | | | 02/08/93 | 21 | 0 | 47 | 2 | 1 | 0 |
| | | | 03/10/93 | 51 | — | 30 | 2 | 1 | 3 |
| | | | 04/10/93 | 82 | | 42 | 11 | 2 | |

| VIRUS | NECROPSY | ANIMAL | DATE | DAY | PTT | PT | INR |
|---|---|---|---|---|---|---|---|
| 1.03 + 10 | 4 DAY | CFB4 | 01/18/93 | 0 | 26.6 | 12.9 | 1.1 |
| | | | 01/22/93 | 4 | 26.0 | 12.4 | 1.0 |
| | 21 DAY | CFB6 | 01/18/93 | 0 | 24.8 | 13.2 | 1.1 |
| | | | 01/22/93 | 4 | 22.3 | 12.8 | 1.0 |
| | | | 02/02/93 | 15 | 24.7 | 13.0 | 1.1 |
| | | | 02/08/93 | 21 | 23.4 | 12.8 | 1.0 |
| | LONG-TERM | CFB8 | 01/18/93 | 0 | 26.8 | 13.3 | 1.1 |
| | | | 01/22/93 | 4 | 24.4 | 12.4 | 1.0 |
| | | | 02/02/93 | 15 | 24.1 | 12.8 | 1.1 |
| | | | 02/08/93 | 21 | 24.9 | 12.7 | 1.0 |
| | | | 03/10/93 | 51 | ND | ND | ND |
| | | | 04/10/93 | 82 | | | |

TABLE IIIa

Blood Chemistries for Toxicity Studies

| | SODIUM | POTASSIUM | CHLORIDE | HCO3 |
|---|---|---|---|---|
| NORMAL ADULT BABOON | 147–153 | 3.6–4.9 | 100–108 | N/A |
| NORMAL JUVENILE BABOON | 143–158 | 3.2–4.3 | 104–118 | N/A |

TABLE IIIa-continued

| Blood Chemistries for Toxicity Studies | | | | |
|---|---|---|---|---|
| | BUN | CREATININE | GLUCOSE | CALCIUM |
| NORMAL ADULT BABOON | 16–22 | 1.3–1.9 | 57–120 | 7.1–10.1 |
| NORMAL JUVENILE BABOON | 9.0–25 | 0.8–1.4 | 50–129 | 8.0–9.6 |
| | PHOSPHOROUS | T. PROTEIN | ALBUMIN | GLOBULIN |
| NORMAL ADULT BABOON | 2.2–5.3 | 5.7–7.7 | 2.8–3.9 | 2.8–4.1 |
| NORMAL JUVENILE BABOON | 4.7–7.7 | 5.8–7.8 | 2.9–4.2 | 2.4–4.4 |
| | SGOT | SGPT | LDH | ALK. PHOS. |
| NORMAL ADULT BABOON | 19–34 | 20–62 | 123–327 | 82–209 |
| NORMAL JUVENILE BABOON | 16–39 | 12.0–81 | 99–488 | 154–1105 |
| | T. BILIRUBIN | CHOLESTEROL | | |
| NORMAL ADULT BABOON | 0.4 | 68–111 | | |
| NORMAL JUVENILE BABOON | 0.3–0.7 | 68–232 | | |

TABLE IIIb

| Blood Chemistries for Toxicity Studies - Study I (Virus = 1.0E + 10) | | | | | | | |
|---|---|---|---|---|---|---|---|
| NECROPSY | ANIMAL | DATE | DAY | SODIUM | POTASSIUM | CHLORIDE | HCO3 |
| 4 DAY | CFB1 | 10/20/92 | −2 | 145 | 3.6 | 102 | 25 |
| NECROPSY | ANIMAL | DATE | DAY | BUN | CREATININE | GLUCOSE | CALCIUM |
| 4 DAY | CFB1 | 10/20/92 | −2 | | | | |
| NECROPSY | ANIMAL | DATE | DAY | PHOSPHORUS | T. PROTEIN | ALBUMIN | GLOBULIN |
| 4 DAY | CFB1 | 10/20/92 | −2 | | | | |
| NECROPSY | ANIMAL | DATE | DAY | SGOT | SGPT | LDH | ALK. PHOS. |
| 4 DAY | CFB1 | 10/20/92 | −2 | | | | |
| NECROPSY | ANIMAL | DATE | DAY | T. BILIRUBIN | CHOLESTEROL | | |
| 4 DAY | CFB1 | 10/20/92 | −2 | | | | |

TABLE IIIc

| Blood Chemistries for Toxicity Studies | | | | | | | |
|---|---|---|---|---|---|---|---|
| NECROPSY | ANIMAL | DATE | DAY | SODIUM | POTASSIUM | CHLORIDE | HCO3 |
| LONG-TERM | CFB2 | 11/06/92 | −3 | 142 | 3.1 | 110 | 25 |
| | | 11/09/92 | 0 | 147 | 4.3 | 107 | 28 |
| | | 11/12/92 | 3 | 142 | 4.5 | 104 | 31 |
| | | 11/23/92 | 14 | 147 | 4.6 | 107 | 27 |
| | | 11/30/92 | 21 | 150 | 4.2 | 106 | 31 |
| | | 01/21/93 | 73 | 147 | 3.5 | 102 | 29 |
| | | 01/25/93 | 77 | 144 | 4.0 | 102 | 29 |
| | | 02/19/93 | 102 | 144 | 3.9 | 101 | 29 |
| | | 03/05/93 | 116 | 147 | 3.9 | 104 | 28 |
| | | 04/10/93 | 152 | 146 | 3.8 | 105 | 29 |
| NECROPSY | ANIMAL | DATE | DAY | BUN | CREATININE | GLUCOSE | CALCIUM |
| LONG-TERM | CFB2 | 11/06/92 | −3 | 13 | 1.3 | 71 | 9.8 |
| | | 11/09/92 | 0 | 19 | 1.3 | 58 | 9.3 |
| | | 11/12/92 | 3 | 16 | 1.2 | 83 | 9.0 |
| | | 11/23/92 | 14 | 19 | 1.1 | 75 | 9.3 |
| | | 11/30/92 | 21 | 23 | 1.1 | 66 | 9.5 |
| | | 01/21/93 | 73 | 24 | 1.1 | 34 | 9.4 |
| | | 01/25/93 | 77 | 23 | 1.2 | 62 | 9.2 |

TABLE IIIc-continued

Blood Chemistries for Toxicity Studies

|  |  | 02/19/93 | 102 | 22 | 1.1 | 59 | 9.2 |
|  |  | 03/05/93 | 116 | 26 | 1.1 | 71 | 9.5 |
|  |  | 04/10/93 | 152 | 27 | 1.2 | 53 | 9.2 |

| NECROPSY | ANIMAL | DATE | DAY | PHOSPHORUS | T. PROTEIN | ALBUMIN | GLOBULIN |
| --- | --- | --- | --- | --- | --- | --- | --- |
| LONG-TERM | CFB2 | 11/06/92 | −3 | 4.3 | 7.2 | 4.4 | −4.4 |
|  |  | 11/09/92 | 0 | 6.3 | 6.5 | 3.8 | −3.8 |
|  |  | 11/12/92 | 3 | 5.1 | 6.1 | 3.1 | −3.1 |
|  |  | 11/23/92 | 14 | 5.8 | 6.9 | 3.5 | −3.5 |
|  |  | 11/30/92 | 21 | 4.7 | 6.5 | 3.5 | −3.5 |
|  |  | 01/21/93 | 73 | 4.0 | 7.1 | 4.1/−4.1 |  |
|  |  | 01/25/93 | 77 | 4.1 | 6.6 | 3.6 | −3.6 |
|  |  | 02/19/93 | 102 | 4.5 | 6.7 | 3.8 | 2.9 |
|  |  | 03/05/93 | 116 | 4.3 | 6.2 | 3.6 | 2.6 |
|  |  | 04/10/93 | 152 | 4.1 | 6.7 | 3.8 | 2.9 |

| NECROPSY | ANIMAL | DATE | DAY | SGOT | SGPT | LDH | ALK. PHOS. |
| --- | --- | --- | --- | --- | --- | --- | --- |
| LONG-TERM | CFB2 | 11/06/92 | −3 | 122 | 121 | 237 | 280 |
|  |  | 11/09/92 | 0 | 56 | 85 | 501 | 130 |
|  |  | 11/12/92 | 3 | 62 | 66 | 655 | 133 |
|  |  | 11/23/92 | 14 | 50 | 110 | 457 | 490 |
|  |  | 11/30/92 | 21 | 44 | 96 | 472 | 338 |
|  |  | 01/21/93 | 73 | 47 | 57 | 762 | 222 |
|  |  | 01/25/93 | 77 | 34 | 74 | 235 | 250 |
|  |  | 02/19/93 | 102 | 63 | 100 | 334 | 200 |
|  |  | 03/05/93 | 116 | 20 | 57 | 134 | 170 |
|  |  | 04/10/93 | 152 | 46 | 95 | 203 | 214 |

| NECROPSY | ANIMAL | DATE | DAY | T. BILIRUBIN | CHOLESTEROL |
| --- | --- | --- | --- | --- | --- |
| LONG-TERM | CFB2 | 11/06/92 | −3 | 0.2 | 70 |
|  |  | 11/09/92 | 0 | 0.2 | 83 |
|  |  | 11/12/92 | 3 | 0.3 | 68 |
|  |  | 11/23/92 | 14 | 0.2 | 92 |
|  |  | 11/30/92 | 21 | 0.2 | 81 |
|  |  | 01/21/93 | 73 | 0.2 | 82 |
|  |  | 01/25/93 | 77 | 0.4 | 84 |
|  |  | 02/19/93 | 102 | 0.5 | 75 |
|  |  | 03/05/93 | 116 | 0.2 | 70 |
|  |  | 04/10/93 | 152 | 0.5 | 76 |

TABLE IIId

Blood Chemistries for Toxicity Studies - Study III (Virus = 1.0E+07)

| NECROPSY | ANIMAL | DATE | DAY | SODIUM | POTASSIUM | CHLORIDE | HCO3 |
| --- | --- | --- | --- | --- | --- | --- | --- |
| 4 DAY | CFB3 | 01/18/93 | 0 | 149 | 3.5 | 100 | 31 |
|  |  | 01/22/93 | 4 | 148 | 4.4 | 102 | 34 |
| 21 DAY | CFB5 | 01/18/93 | 0 | 159 | 3.8 | 110 | 34 |
|  |  | 01/22/93 | 4 | 149 | 3.6 | 102 | 32 |
|  |  | 02/02/93 | 15 | 148 | 3.5 | 102 | 32 |
|  |  | 02/08/93 | 21 | 149 | 3.1 | 101 | 31 |
| LONG-TERM | CFB7 | 01/18/93 | 0 | 146 | 3.9 | 103 | 28 |
|  |  | 01/22/93 | 4 | 148 | 3.8 | 102 | 36 |
|  |  | 02/02/93 | 15 | 143 | 4.0 | 99 | 28 |
|  |  | 02/08/93 | 21 | 148 | 3.6 | 100 | 29 |
|  |  | 03/10/93 | 51 | 146 | 3.6 | 101 | 32 |
|  |  | 04/10/93 | 82 | 146 | 3.5 | 102 | 28 |

| NECROPSY | ANIMAL | DATE | DAY | BUN | CREATININE | GLUCOSE | CALCIUM |
| --- | --- | --- | --- | --- | --- | --- | --- |
| 4 DAY | CFB3 | 01/18/93 | 0 | 18 | 0.6 | 68 | 10.2 |
|  |  | 01/22/93 | 4 | 16 | 0.7 | 52 | 10.3 |
| 21 DAY | CFB5 | 01/18/93 | 0 | 27 | 1.0 | 85 | 10.1 |
|  |  | 01/22/93 | 4 | 17 | 0.8 | 84 | 9.9 |
|  |  | 02/02/93 | 15 | 16 | 0.7 | 65 | 9.6 |
|  |  | 02/08/93 | 21 | 18 | 0.7 | 86 | 9.7 |
| LONG-TERM | CFB7 | 01/18/93 | 0 | 24 | 0.8 | 80 | 9.5 |
|  |  | 01/22/93 | 4 | 21 | 0.7 | 80 | 9.5 |
|  |  | 02/02/93 | 15 | 20 | 0.8 | 61 | 9.1 |
|  |  | 02/08/93 | 21 | 18 | 0.7 | 60 | 9.3 |

TABLE IIId-continued

Blood Chemistries for Toxicity Studies - Study III (Virus = 1.0E+07)

| | | 03/10/93 | 51 | 18 | 0.7 | 67 | 9.4 |
| | | 04/10/93 | 82 | 21 | 0.7 | 70 | 8.9 |

| NECROPSY | ANIMAL | DATE | DAY | PHOSPHORUS | T. PROTEIN | ALBUMIN | GLOBULIN |
|---|---|---|---|---|---|---|---|
| 4 DAY | CFB3 | 01/18/93 | 0 | 6.0 | 7.5 | 4 | 3.5 |
| | | 01/22/93 | 4 | 5.9 | 6.8 | 3.9 | 2.9 |
| 21 DAY | CFB5 | 01/18/93 | 0 | 6.0 | 7.1 | 4 | 3.1 |
| | | 01/22/93 | 4 | 4.3 | 7.1 | 4.2 | 2.9 |
| | | 02/02/93 | 15 | 5.8 | 6.8 | 3.9 | 2.9 |
| | | 02/08/93 | 21 | 5.2 | 6.6 | 3.7 | 2.9 |
| LONG-TERM | CFB7 | 01/18/93 | 0 | 6.1 | 6.5 | 3.7 | 2.8 |
| | | 01/22/93 | 4 | 5.7 | 6.5 | 3.6 | 2.9 |
| | | 02/02/93 | 15 | 5.1 | 7 | 3.8 | 3.2 |
| | | 02/08/93 | 21 | 6.2 | 6.7 | 3.7 | 3.0 |
| | | 03/10/93 | 51 | 6.1 | 6.3 | 3.6 | 2.7 |
| | | 04/10/93 | 82 | 5.7 | 6.5 | 3.6 | 2.9 |

| NECROPSY | ANIMAL | DATE | DAY | SGOT | SGPT | LDH | ALK. PHOS. |
|---|---|---|---|---|---|---|---|
| 4 DAY | CFB3 | 01/18/93 | 0 | 46 | 28 | 406 | 706 |
| | | 01/22/93 | 4 | 45 | 29 | 438 | 676 |
| 21 DAY | CFB5 | 01/18/93 | 0 | 17 | 14 | 217 | 772 |
| | | 01/22/93 | 4 | 25 | 20 | 320 | 702 |
| | | 02/02/93 | 15 | 34 | 23 | 332 | 727 |
| | | 02/08/93 | 21 | 36 | 20 | 455 | 632 |
| LONG-TERM | CFB7 | 01/18/93 | 0 | 24 | 19 | 232 | 1127 |
| | | 01/22/93 | 4 | 28 | 20 | 299 | 862 |
| | | 02/02/93 | 15 | 32 | 18 | 296 | 991 |
| | | 02/08/93 | 21 | 26 | 20 | 272 | 872 |
| | | 03/10/93 | 51 | 29 | 19 | 255 | 967 |
| | | 04/10/93 | 82 | 19 | 9 | 229 | 824 |

| NECROPSY | ANIMAL | DATE | DAY | T. BILIRUBIN | CHOLESTEROL | | |
|---|---|---|---|---|---|---|---|
| 4 DAY | CFB3 | 01/18/93 | 0 | 0.2 | 100 | | |
| | | 01/22/93 | 4 | 0.2 | 83 | | |
| 21 DAY | CFB5 | 01/18/93 | 0 | 0.2 | 95 | | |
| | | 01/22/93 | 4 | 0.2 | 86 | | |
| | | 02/02/93 | 15 | 0.2 | 84 | | |
| | | 02/08/93 | 221 | 0.2 | 79 | | |
| LONG-TERM | CFB7 | 01/18/93 | 0 | 0.3 | 80 | | |
| | | 01/22/93 | 4 | 0.2 | 86 | | |
| | | 02/02/93 | 15 | 0.2 | 86 | | |
| | | 02/08/93 | 21 | 0.2 | 81 | | |
| | | 03/10/93 | 51 | 0.2 | 84 | | |
| | | 04/10/93 | 82 | 0.2 | 84 | | |

TABLE IIIe

Blood Chemistries for Toxicity Studies

| NECROPSY | ANIMAL | DATE | DAY | SODIUM | POTASSIUM | CHLORIDE | HCO3 |
|---|---|---|---|---|---|---|---|
| 4 DAY | CFB10 | 02/03/93 | -13 | 147 | 3.6 | 101 | 19 |
| | | 02/10/93 | -6 | 146 | 3.4 | 102 | 23 |
| | | 02/16/93 | 0 | 147 | 3.4 | 102 | 29 |
| | | 02/20/93 | 4 | 146 | 3.3 | 101 | 27 |
| 21 DAY | CFB14 | 01/29/93 | -18 | 146 | 4.3 | 104 | 25 |
| | | 02/16/93 | 0 | 146 | 3.1 | 101 | 28 |
| | | 02/20/93 | 4 | 145 | 3.6 | 100 | 28 |
| | | 03/02/93 | 14 | 145 | 3.6 | 101 | 24 |
| | | 03/09/93 | 21 | 144 | 3.5 | 100 | 27 |
| LONG-TERM | CFB16 | 01/29/93 | -18 | 146 | 3.7 | 104 | 16 |
| | | 02/16/93 | 0 | 147 | 4.0 | 102 | 24 |
| | | 02/20/93 | 4 | 144 | 3.9 | 99 | 25 |
| | | 03/02/93 | 14 | 144 | 4.0 | 101 | 26 |
| | | 03/09/93 | 21 | 146 | 4.0 | 102 | 24 |
| | | 04/10/93 | 53 | 144 | 3.6 | 104 | 25 |

| NECROPSY | ANIMAL | DATE | DAY | BUN | CREATININE | GLUCOSE | CALCIUM |
|---|---|---|---|---|---|---|---|
| 4 DAY | CFB10 | 02/03/93 | -13 | 14 | 0.6 | 110 | 9.1 |
| | | 02/10/93 | -6 | 23 | 0.6 | 87 | 9.3 |
| | | 02/16/93 | 0 | 19 | 0.6 | 10 | 9.6 |
| | | 02/20/93 | 4 | 15 | 0.7 | 77 | 9.1 |

TABLE IIIe-continued

Blood Chemistries for Toxicity Studies

| 21 DAY | CFB14 | 01/29/93 | −18 | 8 | 0.5 | 92 | 10.1 |
|---|---|---|---|---|---|---|---|
| | | 02/16/93 | 0 | 11 | 0.4 | 69 | 10.1 |
| | | 02/20/93 | 4 | 11 | 0.5 | 90 | 10.1 |
| | | 03/02/93 | 14 | 12 | 0.5 | 90 | 10.0 |
| | | 03/09/93 | 21 | 12 | 0.6 | 82 | 10.0 |
| LONG-TERM | CFB16 | 01/29/93 | −18 | 9 | 0.7 | 98 | 9.6 |
| | | 02/16/93 | 0 | 10 | 0.6 | 72 | 10.4 |
| | | 02/20/93 | 4 | 13 | 0.5 | 76 | 10.1 |
| | | 03/02/93 | 14 | 15 | 0.5 | 69 | 9.8 |
| | | 03/09/93 | 21 | 14 | 0.5 | 65 | 10.3 |
| | | 04/10/93 | 53 | 15 | 0.6 | 74 | 9.9 |

| NECROPSY | ANIMAL | DATE | DAY | PHOSPHORUS | T. PROTEIN | ALBUMIN | GLOBULIN |
|---|---|---|---|---|---|---|---|
| 4 DAY | CFB10 | 02/03/93 | −13 | 4.7 | 7.2 | 3.6 | 3.6 |
| | | 02/10/93 | −6 | 4.4 | 6.9 | 3.5 | 3.4 |
| | | 02/16/93 | 0 | 3.9 | 6.7 | 3.5 | 3.2 |
| | | 02/20/93 | 4 | 5.2 | 6.7 | 3.4 | 3.3 |
| 21 DAY | CFB14 | 01/29/93 | −18 | 6.4 | 7.5 | 3.9 | 3.6 |
| | | 02/16/93 | 0 | 7.1 | 7 | 3.7 | 3.3 |
| | | 02/20/93 | 4 | 6.7 | 7 | 3.8 | 3.2 |
| | | 03/02/93 | 14 | 7.0 | 6.9 | 3.8 | 3.1 |
| | | 03/09/93 | 21 | 6.7 | 6.8 | 3.8 | 3.0 |
| LONG-TERM | CFB16 | 01/29/93 | −18 | 5.8 | 7.4 | 4.4 | 3.0 |
| | | 02/16/93 | 0 | 7.3 | 7.8 | 4.6 | 3.2 |
| | | 02/20/93 | 4 | 6.1 | 7.4 | 4.2 | 3.2 |
| | | 03/02/93 | 14 | 6.1 | 7.2 | 4.0 | 3.2 |
| | | 03/09/93 | 21 | 5.6 | 7.2 | 4.1 | 3.1 |
| | | 04/10/93 | 53 | 5.3 | 6.9 | 4.0 | 2.9 |

| NECROPSY | ANIMAL | DATE | DAY | SGOT | SGPT | LDH | ALK. PHOS. |
|---|---|---|---|---|---|---|---|
| 4 DAY | CFB10 | 02/03/93 | −13 | 33 | 25 | 328 | 633 |
| | | 02/10/93 | −6 | 20 | 21 | 227 | 620 |
| | | 02/16/93 | 0 | 36 | 29 | 326 | 592 |
| | | 02/20/93 | 4 | 20 | 25 | 234 | 639 |
| 21 DAY | CFB14 | 01/29/93 | −18 | 28 | 32 | 285 | 771 |
| | | 02/16/93 | 0 | 28 | 74 | 256 | 663 |
| | | 02/20/93 | 4 | 16 | 41 | 173 | 703 |
| | | 03/02/93 | 14 | 15 | 43 | 179 | 874 |
| | | 03/09/93 | 21 | 23 | 41 | 180 | 902 |
| LONG-TERM | CFB16 | 01/29/93 | −18 | 22 | 29 | 208 | 630 |
| | | 02/16/93 | 0 | 17 | 34 | 230 | 581 |
| | | 02/20/93 | 4 | 11 | 28 | 188 | 493 |
| | | 03/02/93 | 14 | 16 | 32 | 191 | 600 |
| | | 03/09/93 | 21 | 18 | 35 | 180 | 594 |
| | | 04/10/93 | 53 | 17 | 25 | 168 | 673 |

| NECROPSY | ANIMAL | DATE | DAY | T. BILIRUBIN | CHOLESTEROL |
|---|---|---|---|---|---|
| 4 DAY | CFB10 | 02/03/93 | −13 | 0.3 | 102 |
| | | 02/10/93 | −6 | 0.1 | 105 |
| | | 02/16/93 | 0 | 0.1 | 102 |
| | | 02/20/93 | 4 | 0.2 | 107 |
| 21 DAY | CFB14 | 01/29/93 | −18 | 0.5 | 156 |
| | | 02/16/93 | 0 | 0.3 | 140 |
| | | 02/20/93 | 4 | 0.2 | 140 |
| | | 03/02/93 | 14 | 0.2 | 128 |
| | | 03/09/93 | 21 | 0.2 | 124 |
| LONG-TERM | CFB16 | 01/29/93 | −18 | 0.5 | 202 |
| | | 02/16/93 | 0 | 0.2 | 177 |
| | | 02/20/93 | 4 | 0.2 | 137 |
| | | 03/02/93 | 14 | 0.2 | 139 |
| | | 03/09/93 | 21 | 0.2 | 136 |
| | | 04/10/93 | 53 | 0.3 | 131 |

TABLE IIIf

Blood Chemistries for Toxicity Studies - Study III (Virus = 1.0E+09)

| NECROPSY | ANIMAL | DATE | DAY | SODIUM | POTASSIUM | CHLORIDE | HCO3 |
|---|---|---|---|---|---|---|---|
| 4 DAY | CFB11 | 02/03/93 | −13 | 150 | 3.8 | 103 | 17 |
| | | 02/16/93 | 0 | 147 | 4.1 | 101 | 15 |
| | | 02/20/93 | 4 | 148 | 4.0 | 101 | 19 |

TABLE IIIf-continued

| Blood Chemistries for Toxicity Studies - Study III (Virus = 1.0E+09) | | | | | | | |
|---|---|---|---|---|---|---|---|
| 21 DAY | CFB13 | 01/29/93 | −18 | 147 | 4.0 | 104 | 27 |
| | | 02/16/93 | 0 | 148 | 3.5 | 103 | 28 |
| | | 02/20/93 | 4 | 143 | 3.8 | 99 | 27 |
| | | 03/02/93 | 14 | 145 | 4.1 | 100 | 27 |
| | | 03/09/93 | 21 | 146 | 3.6 | 101 | 29 |
| LONG-TERM | CFB15 | 02/03/93 | −13 | 146 | 4.2 | 101 | 22 |
| | | 02/16/93 | 0 | 147 | 4.3 | 10.3 | 17 |
| | | 02/20/93 | 4 | 147 | 4.2 | 102 | 19 |
| | | 03/02/93 | 14 | 147 | 4.0 | 102 | 25 |
| | | 03/09/93 | 21 | 147 | 4.3 | 103 | 18 |
| | | 04/10/93 | 53 | 145 | 3.7 | 103 | 21 |

| NECROPSY | ANIMAL | DATE | DAY | BUN | CREATININE | GLUCOSE | CALCIUM |
|---|---|---|---|---|---|---|---|
| 4 DAY | CFB11 | 02/03/93 | −13 | 18 | 0.9 | 90 | 10.1 |
| | | 02/16/93 | 0 | 21 | 0.9 | 58 | 10.3 |
| | | 02/20/93 | 4 | 14 | 0.8 | 80 | 10.0 |
| 21 DAY | CFB13 | 01/29/93 | −18 | 13 | 0.8 | 88 | 9.7 |
| | | 02/16/93 | 0 | 15 | 0.6 | 62 | 9.7 |
| | | 02/20/93 | 4 | 16 | 0.7 | 66 | 9.7 |
| | | 03/02/93 | 14 | 17 | 0.6 | 63 | 9.9 |
| | | 03/09/93 | 21 | 17 | 0.6 | 56 | 10.1 |
| LONG-TERM | CFB15 | 02/03/93 | −13 | 22 | 0.9 | 100 | 10.2 |
| | | 02/16/93 | 0 | 18 | 0.7 | 83 | 10.0 |
| | | 02/20/93 | 4 | 18 | 0.7 | 91 | 9.5 |
| | | 03/02/93 | 14 | 18 | 0.7 | 69 | 9.6 |
| | | 03/09/93 | 21 | 22 | 0.7 | 73 | 10.0 |
| | | 04/10/93 | 53 | 22 | 0.7 | 79 | 9.8 |
| 4 DAY | CFB11 | 02/03/93 | −13 | 6.8 | 7.1 | 4.1 | 3.0 |
| | | 02/16/93 | 0 | 8.8 | 6.4 | 4 | 2.4 |
| | | 02/20/93 | 4 | 7.3 | 7.3 | 4.3 | 3.0 |
| 21 DAY | CFB13 | 01/29/93 | −18 | 4.5 | 7.2 | 3.6 | 3.6 |
| | | 02/16/93 | 0 | 7.8 | 7.4 | 3.8 | 3.6 |
| | | 02/20/93 | 4 | 5.7 | 6.9 | 3.7 | 3.2 |
| | | 03/02/93 | 14 | 6.9 | 7.2 | 4.0 | 3.2 |
| | | 03/09/93 | 21 | 6.7 | 7.2 | 4.0 | 3.2 |
| LONG-TERM | CFB15 | 02/03/93 | −13 | 5.5 | 7.2 | 4 | 3.2 |
| | | 02/16/93 | 0 | 8.5 | 7.4 | 4 | 3.4 |
| | | 02/20/93 | 4 | 6.8 | 7.2 | 4 | 3.2 |
| | | 03/02/93 | 21 | 6.4 | 7.1 | 4.1 | 3.0 |
| | | 03/09/93 | 21 | 6.4 | 7.1 | 4.1 | 3.0 |
| | | 04/10/93 | 53 | 6.2 | 6.9 | 3.9 | 3.0 |

| NECROPSY | ANIMAL | DATE | DAY | SGOT | SGPT | LDH | ALK. PHOS. |
|---|---|---|---|---|---|---|---|
| 4 DAY | CFB11 | 02/03/93 | −13 | 14 | 32 | 261 | 1202 |
| | | 02/16/93 | 0 | 18 | 39 | 243 | 937 |
| | | 02/20/93 | 4 | 14 | 30 | 241 | 995 |
| 21 DAY | CFB13 | 01/29/93 | −18 | 26 | 162 | 166 | 641 |
| | | 02/16/93 | 0 | 28 | 45 | 227 | 561 |
| | | 02/20/93 | 4 | 21 | 33 | 179 | 521 |
| | | 03/02/93 | 14 | 31 | 76 | 206 | 725 |
| | | 03/09/93 | 21 | 30 | 51 | 229 | 743 |
| LONG-TERM | CFB15 | 02/03/93 | −13 | 8 | 27 | 152 | 672 |
| | | 02/16/93 | 0 | 11 | 31/ 156 | 683 | |
| | | 02/20/93 | 4 | 9 | 31 | 172 | 649 |
| | | 03/02/93 | 14 | 26 | 49 | 217 | 675 |
| | | 03/09/93 | 21 | 36 | 52 | 264 | 659 |
| | | 04/10/93 | 53 | 17.0 | 30 | 210 | 833 |

| NECROPSY | ANIMAL | DATE | DAY | T. BILIRUBIN | CHOLESTEROL |
|---|---|---|---|---|---|
| 4 DAY | CFB11 | 02/03/93 | −13 | 0.1 | 131 |
| | | 02/16/93 | 0 | 0.1 | 131 |
| | | 02/20/93 | 4 | 0.2 | 149 |
| 21 DAY | CFB13 | 01/29/93 | −18 | 0.2 | 109 |
| | | 02/16/93 | 0 | 0.2 | 107 |
| | | 02/20/93 | 4 | 0.2 | 100 |
| | | 03/02/93 | 14 | 0.1 | 102 |
| | | 03/09/93 | 21 | 0.2 | 99 |
| LONG-TERM | CFB15 | 02/03/93 | −13 | 0 | 116 |
| | | 02/16/93 | 0 | 0.2 | 128 |
| | | 02/20/93 | 4 | 0.2 | 128 |
| | | 03/02/93 | 14 | 0.1 | 113 |

TABLE IIIf-continued

| | | | | |
|---|---|---|---|---|
| | 03/09/93 | 21 | 0.1 | 113 |
| | 04/10/93 | 53 | 0.1 | 111 |

Blood Chemistries for Toxicity Studies - Study III (Virus = 1.0E+09)

TABLE IIIg

Blood Chemistries for Toxicity Studies - Study III (Virus = 1.0E+10)

| NECROPSY | ANIMAL | DATE | DAY | SODIUM | POTASSIUM | CHLORIDE | HCO3 |
|---|---|---|---|---|---|---|---|
| 4 DAY | CFB4 | 01/18/93 | 0 | 145 | 3.6 | 100 | 31 |
| | | 01/22/93 | 4 | 145 | 3.6 | 102 | 30 |
| 21 DAY | CFB6 | 01/18/93 | 0 | 149 | 4.4 | 102 | 31 |
| | | 01/22/93 | 4 | 150 | 4.0 | 101 | 24 |
| | | 02/02/93 | 15 | 146 | 4.3 | 100 | 31 |
| | | 02/08/93 | 21 | 149 | 3.7 | 103 | 29 |
| LONG-TERM | CFB8 | 01/18/93 | 0 | 148 | 3.7 | 106 | 25 |
| | | 01/22/93 | 4 | 146 | 3.9 | 101 | 29 |
| | | 02/02/93 | 15 | 148 | 3.8 | 104 | 28 |
| | | 02/08/93 | 21 | 149 | 3.6 | 104 | 23 |
| | | 03/10/93 | 51 | 149 | 3.8 | 102 | 32 |
| | | 04/10/93 | 82 | 147 | 3.4 | 106 | 25 |

| NECROPSY | ANIMAL | DATE | DAY | BUN | CREATININE | GLUCOSE | CALCIUM |
|---|---|---|---|---|---|---|---|
| 4 DAY | CFB4 | 01/18/93 | 0 | 17 | 0.5 | 70 | 10.0 |
| | | 01/22/93 | 4 | 19 | 0.5 | 56 | 10.0 |
| 21 DAY | CFB6 | 01/18/93 | 0 | 16 | 0.9 | 95 | 10.2 |
| | | 01/22/93 | 4 | 18 | 1.0 | 75 | 10.1 |
| | | 02/02/93 | 15 | 14 | 1.0 | 92 | 9.4 |
| | | 02/08/93 | 21 | 14 | 0.8 | 93 | 9.6 |
| LONG-TERM | CFB8 | 01/18/93 | 0 | 14 | 0.7 | 79 | 9.9 |
| | | 01/22/93 | 4 | 14 | 0.6 | 79 | 9.7 |
| | | 02/02/93 | 15 | 14 | 0.8 | 64 | 9.5 |
| | | 02/08/93 | 21 | 12 | 0.8 | 83 | 9.3 |
| | | 03/10/93 | 51 | 16 | 0.8 | 66 | 9.3 |
| | | 04/10/93 | 82 | 16 | 0.7 | 79 | 9.5 |

| NECROPSY | ANIMAL | DATE | DAY | PHOSPHORUS | T. PROTEIN | ALBUMIN | GLOBULIN |
|---|---|---|---|---|---|---|---|
| 4 DAY | CFB4 | 01/18/93 | 0 | 5.6 | 6.9 | 3.6 | 3.3 |
| | | 01/22/93 | 4 | 5.5 | 6.7 | 3.5 | 3.2 |
| 21 DAY | CFB6 | 01/18/93 | 0 | 5.5 | 7.2 | 4.1 | 3.1 |
| | | 01/22/93 | 4 | 5.6 | 7.4 | 4.3 | 3.1 |
| | | 02/02/93 | 15 | 4.6 | 6.6 | 3.5 | 3.1 |
| | | 02/08/93 | 21 | 4.5 | 6.8 | 3.8 | 3.0 |
| LONG-TERM | CFB8 | 01/18/93 | 0 | 6.4 | 6.5 | 3.7 | 2.8 |
| | | 01/22/93 | 4 | 4.7 | 6.5 | 3.6 | 2.9 |
| | | 02/02/93 | 15 | 5.4 | 6.3 | 3.4 | 2.9 |
| | | 02/08/93 | 21 | 5.5 | 6.2 | 3.5 | 2.7 |
| | | 03/10/93 | 51 | 5.5 | 6.6 | 3.7 | 2.9 |
| | | 04/10/93 | 82 | 5.5 | 6.4 | 3.6 | 2.8 |

| NECROPSY | ANIMAL | DATE | DAY | SGOT | SGPT | LDH | ALK. PHOS. |
|---|---|---|---|---|---|---|---|
| 4 DAY | CFB4 | 01/18/93 | 0 | 28 | 32 | 216 | 877 |
| | | 01/22/93 | 4 | 45 | 34 | 512 | 822 |
| 21 DAY | CFB6 | 01/18/93 | 0 | 17 | 28 | 178 | 579 |
| | | 01/22/93 | 4 | 23 | 26 | 291 | 503 |
| | | 02/02/93 | 15 | 23 | 26 | 253 | 483 |
| | | 02/08/93 | 21 | 28 | 33 | 291 | 486 |
| LONG-TERM | CFB8 | 01/18/93 | 0 | 32 | 29 | 283 | 782 |
| | | 01/22/93 | 4 | 25 | 25 | 312 | 677 |
| | | 02/02/93 | 15 | 32 | 24 | 327 | 723 |
| | | 02/08/93 | 21 | 31 | 30 | 335 | 724 |
| | | 03/10/93 | 51 | 30 | 28 | 321 | 728 |
| | | 04/10/93 | 82 | 34 | 27 | 326 | 855 |

| NECROPSY | ANIMAL | DATE | DAY | T. BILIRUBIN | CHOLESTEROL |
|---|---|---|---|---|---|
| 4 DAY | CFB4 | 01/18/93 | 0 | 0.2 | 97 |
| | | 01/22/93 | 4 | 0.2 | 102 |
| 21 DAY | CFB6 | 01/18/93 | 0 | 0.2 | 79 |
| | | 01/22/93 | 4 | 0.2 | 88 |
| | | 02/02/93 | 15 | 0.2 | 76 |
| | | 02/08/93 | 21 | 0.2 | 81 |
| LONG-TERM | CFB8 | 01/18/93 | 0 | 0.1 | 78 |

TABLE IIIg-continued

Blood Chemistries for Toxicity Studies - Study III (Virus = 1.0E+10)

| | | | |
|---|---|---|---|
| 01/22/93 | 4 | 0.1 | 85 |
| 02/02/93 | 15 | 0.2 | 78 |
| 02/08/93 | 21 | 0.1 | 79 |
| 03/10/93 | 51 | 0.1 | 81 |
| 04/10/93 | 82 | 0.2 | 82 |

TABLE IVa

Urinalysis for Baboon Toxicity Studies (Study I)

| VIRUS | NECROPSY | ANIMAL | DATE | DAY | Urine | Specific gravity | pH | Leuk esterase |
|---|---|---|---|---|---|---|---|---|
| 1.0E+10 | 4 DAY | CFB1 | 10/20/92 | −2 | ND | ND | ND | ND |

| VIRUS | NECROPSY | ANIMAL | DATE | DAY | Nitrite | Protein | Glucose | Ketones |
|---|---|---|---|---|---|---|---|---|
| 1.0E+10 | 4 DAY | CFB1 | 10/20/92 | −2 | ND | ND | ND | ND |

| VIRUS | NECROPSY | ANIMAL | DATE | DAY | Urobilin | Bilirubin | Blood | RBC/hpf |
|---|---|---|---|---|---|---|---|---|
| 1.0E+10 | 4 DAY | CFB1 | 10/20/92 | −2 | ND | ND | ND | ND |

| VIRUS | NECROPSY | ANIMAL | DATE | DAY | WBC/hpf | Casts | | |
|---|---|---|---|---|---|---|---|---|
| 1.0E+10 | 4 DAY | CFB1 | 10/20/92 | −2 | ND | ND | | |

TABLE IVb

Urinalysis for Baboon Toxicity Studies (Study II)

| VIRUS | NECROPSY | ANIMAL | DATE | DAY | Urine | Specific gravity | pH | Leuk esterase |
|---|---|---|---|---|---|---|---|---|
| 1.0E + 10 | LONG-TERM | CFB2 | 11/09/92 | 0 | ND | ND | 6 | 0 |
| | | | 11/12/92 | 3 | YELLOW, CLEAR | 1.005 | 5 | 0 |
| | | | 11/30/92 | 21 | ND | ND | 6 | 0 |
| | | | 01/25/93 | 77 | ND | ND | 6 | 0 |

| VIRUS | NECROPSY | ANIMAL | DATE | DAY | Nitrite | Protein | Glucose | Ketones |
|---|---|---|---|---|---|---|---|---|
| 1.0E + 10 | LONG-TERM | CFB2 | 11/09/92 | 0 | ND | 0 | 0 | 0 |
| | | | 11/12/92 | 3 | 0 | 0 | 0 | 0 |
| | | | 11/30/92 | 21 | ND | 0 | 0 | 0 |
| | | | 01/25/93 | 77 | ND | 0 | 0 | 0 |

| VIRUS | NECROPSY | ANIMAL | DATE | DAY | Urobilin | Bilirubin | Blood | RBC/hpf |
|---|---|---|---|---|---|---|---|---|
| 1.0E + 10 | LONG-TERM | CFB2 | 11/09/92 | 0 | ND | ND | 0 | ND |
| | | | 11/12/92 | 3 | 0 | 0 | 0 | occ |
| | | | 11/30/92 | 21 | ND | ND | 0 | ND |
| | | | 01/25/93 | 77 | ND | ND | 1 | ND |

| VIRUS | NECROPSY | ANIMAL | DATE | DAY | WBC/hpf | Casts | | |
|---|---|---|---|---|---|---|---|---|
| 1.0E + 10 | LONG-TERM | CFB2 | 11/09/92 | 0 | ND | ND | | |
| | | | 11/12/92 | 3 | occ | 0 | | |
| | | | 11/30/92 | 21 | ND | ND | | |
| | | | 01/25/93 | 77 | ND | ND | | |

TABLE IVc

Urinalysis for Baboon Toxicity Studies (Study III)

| VIRUS | NECROPSY | ANIMAL | DATE | DAY | Urine | Specific gravity | pH | Leuk esterase |
|---|---|---|---|---|---|---|---|---|
| 1.0E + 07 | 4 DAY | CFB3 | 01/18/93 | 0 | YELLOW, HAZY | 1.005 | 7 | 0 |
| | | | 01/22/93 | 4 | YELLOW, HAZY | 1.005 | 7 | 0 |
| | 21 DAY | CFB6 | 01/18/93 | 0 | YELLOW, CLEAR | 1.012 | 7 | 0 |

TABLE IVc-continued

Urinalysis for Baboon Toxicity Studies (Study III)

|  |  |  | 02/08/93 | 21 | YELLOW, CLEAR | 1.005 | 7 | 0 |
|---|---|---|---|---|---|---|---|---|
|  | LONG-TERM | CFB7 | 01/18/93 | 0 | YELLOW, HAZY | 1.019 | 5 | 0 |
|  |  |  | 01/22/93 | 4 | YELLOW, HAZY | 1.005 | 8 | 0 |
|  |  |  | 02/02/93 | 15 | YELLOW, CLEAR | 1.018 | 8 | 0 |
|  |  |  | 02/08/93 | 21 | YELLOW, CLEAR | 1.017 | 8 | 0 |

| VIRUS | NECROPSY | ANIMAL | DATE | DAY | Nitrite | Protein | Glucose | Ketones |
|---|---|---|---|---|---|---|---|---|
| 1.0E + 07 | 4 DAY | CFB3 | 01/18/93 | 0 | 0 | 0 | 0 | 0 |
|  |  |  | 01/22/93 | 4 | 0 | 0 | 0 | 0 |
|  | 21 DAY | CFB5 | 01/18/93 | 0 | 0 | 0 | 0 | 0 |
|  |  |  | 02/08/93 | 21 | 0 | 0 | 0 | 0 |
|  | LONG-TERM | CFB7 | 01/18/93 | 0 | 0 | 0 | 0 | 0 |
|  |  |  | 01/22/93 | 4 | 0 | 0 | 0 | 0 |
|  |  |  | 02/02/93 | 15 | 0 | 0 | 0 | 0 |
|  |  |  | 02/08/93 | 21 | 0 | 0 | 0 | 0 |

| VIRUS | NECROPSY | ANIMAL | DATE | DAY | Urobilin | Bilirubin | Blood | RBC/hpf |
|---|---|---|---|---|---|---|---|---|
| 1.0E + 07 | 4 DAY | CFB3 | 01/18/93 | 0 | 0 | 0 | 0 | 0 |
|  |  |  | 01/22/93 | 4 | 0 | 0 | 0 | 0 |
|  | 21 DAY | CFBS | 01/18/93 | 0 | 0 | 0 | 0 | ND |
|  |  |  | 02/08/93 | 21 | 0 | 0 | 0 | ND |
|  | LONG-TERM | CFB7 | 01/18/93 | 0 | 0 | 0 | 0 | 0 |
|  |  |  | 01/22/93 | 4 | 0 | 0 | 0 | ND |
|  |  |  | 02/02/93 | 15 | 0 | 0 | 0 | ND |
|  |  |  | 02/08/93 | 21 | 0 | 0 | ND |  |

| VIRUS | NECROPSY | ANIMAL | DATE | DAY | WBC/hpf | Casts |
|---|---|---|---|---|---|---|
| 1.0E + 07 | 4 DAY | CFB3 | 01/18/93 | 0 | 0 | 0 |
|  |  |  | 01/22/93 | 4 | 0 | 0 |
|  | 21 DAY | CFBS | 01/18/93 | 0 | ND | ND |
|  |  |  | 02/08/93 | 21 | ND | ND |
|  | LONG-TERM | CFB7 | 01/18/93 | 0 | occ | 0 |
|  |  |  | 01/22/93 | 4 | ND | ND |
|  |  |  | 02/02/93 | 15 | ND | ND |
|  |  |  | 02/08/93 | 21 | ND | ND |

TABLE IVd

Urinalysis for Baboon Toxicity Studies (Study III)

| VIRUS | NECROPSY | ANIMAL | DATE | DAY | Urine | Specific gravity | pH | Leuk esterase |
|---|---|---|---|---|---|---|---|---|
| 1.0E + 08 | 4 DAY | CFB10 | 02/16/93 | 0 | YELLOW, CLEAR | 1.004 | 6 | 0 |
|  |  |  | 02/20/93 | 4 | YELLOW, CLEAR | 1.003 | 6 | 0 |
|  | 21 DAY | CFB14 | 02/16/93 | 0 | YELLOW, HAZY | 1.005 | 7 | 0 |
|  |  |  | 02/20/93 | 4 | YELLOW, CLEAR | 1.010 | 5 | 0 |
|  |  |  | 03/02/93 | 14 | YELLOW, CLEAR | 1.003 | 7 | 0 |
|  |  |  | 03/09/93 | 21 | YELLOW, CLEAR | 1.004 | 7 | 0 |
|  | LONG-TERM | CFB16 | 02/16/93 | 0 | STRAW, CLEAR | 1.001 | 5 | 0 |
|  |  |  | 02/20/93 | 4 | YELLOW, CLOUDY | 1.024 | 5 | 0 |
|  |  |  | 03/02/93 | 14 | YELLOW, HAZY | 1.028 | 8 | 0 |
|  |  |  | 03/09/93 | 21 | YELLOW, CLEAR | 1.011 | 8 | 0 |

| VIRUS | NECROPSY | ANIMAL | DATE | DAY | Nitrite | Protein | Glucose | Ketones |
|---|---|---|---|---|---|---|---|---|
| 1.0E + 08 | 4 DAY | CFB10 | 02/16/93 | 0 | 0 | 0 | 0 | 0 |
|  |  |  | 02/20/93 | 4 | 0 | 0 | 0 | 0 |
|  | 21 DAY | CFB14 | 02/16/93 | 0 | 0 | 0 | 0 | 0 |
|  |  |  | 02/20/93 | 4 | 0 | 0 | 0 |  |
|  |  |  | 03/02/93 | 14 | 0 | 0 | 0 | 0 |
|  |  |  | 03/09/93 | 21 | 0 | 0 | 0 | 0 |
|  | LONG-TERM | CFB16 | 02/16/93 | 0 | 0 | 0 | 0 |  |
|  |  |  | 02/20/93 | 4 | 0 | 30 | 0 | 0 |
|  |  |  | 03/02/93 | 14 | 0 | 15 | 0 | 0 |
|  |  |  | 03/09/93 | 21 | 0 | 15 | 0 | 0 |

| VIRUS | NECROPSY | ANIMAL | DATE | DAY | Urobilin | Bilirubin | Blood | RBC/hpf |
|---|---|---|---|---|---|---|---|---|
| 1.0E + 08 | 4 DAY | CFB10 | 02/16/93 | 0 | 0 | 0 | 0 | ND |
|  |  |  | 02/20/93 | 4 | 0 | 0 | 0 | ND |
|  | 21 DAY | CFB14 | 02/16/93 | 0 | 0 | 0 | 0 | ND |
|  |  |  | 02/20/93 | 4 | 0 | 0 | 300 | 0 to 3 |
|  |  |  | 03/02/93 | 14 | 0 | 0 | 0 | ND |

TABLE IVd-continued

Urinalysis for Baboon Toxicity Studies (Study III)

|  |  |  | 03/09/93 | 21 | 0 | 0 | 0 | ND |
|---|---|---|---|---|---|---|---|---|
|  | LONG-TERM | CFB16 | 02/16/93 | 0 | 0 | 0 | 0 | ND |
|  |  |  | 02/20/93 | 4 | 0 | 0 | 0 | 5 to 10 |
|  |  |  | 03/02/93 | 14 | 0 | 0 | 60 | 50 to 75 |
|  |  |  | 03/09/93 | 21 | 0 | 0 | 10 | 5 to 10 |

| VIRUS | NECROPSY | ANIMAL | DATE | DAY | WBC/hpf | Casts |
|---|---|---|---|---|---|---|
| 1.0E + 08 | 4 DAY | CFB10 | 02/16/93 | 0 | ND | ND |
|  |  |  | 02/20/93 | 4 | ND | ND |
|  | 21 DAY | CFB14 | 02/16/93 | 0 | ND | ND |
|  |  |  | 02/20/93 | 4 | occ | 0 |
|  |  |  | 03/02/93 | 14 | ND | ND |
|  |  |  | 03/09/93 | 21 | ND | ND |
|  | LONG-TERM | CFB16 | 02/16/93 | 0 | ND | ND |
|  |  |  | 02/20/93 | 4 | 0 | 0 |
|  |  |  | 03/02/93 | 14 | 0 to 3 | 0 |
|  |  |  | 03/09/93 | 21 | 0 to 3 | 0 |

TABLE IVe

Urinalysis for Baboon Toxicity Studies (Study III)

| VIRUS | NECROPSY | ANIMAL | DATE | DAY | Urine | Specific gravity | pH | Leuk esterase |
|---|---|---|---|---|---|---|---|---|
| 1.0E + 09 | 4 DAY | CFB11 | 02/16/93 | 0 | YELLOW, HAZY | 1.020 | 5 | 0 |
|  |  |  | 02/20/93 | 4 | YELLOW, CLEAR | 1.016 | 7 | 0 |
|  | 21 DAY | CFB13 | 02/16/93 | 0 | STRAW, CLEAR | 1.005 | 5 | 0 |
|  |  |  | 02/20/93 | 4 | YELLOW, CLEAR | 1.005 | 7 | 0 |
|  |  |  | 03/02/93 | 14 | YELLOW, CLOUDY | 1.021 | 8 | 0 |
|  |  |  | 03/09/93 | 21 | YELLOW, CLEAR | 1.005 | 5 | 0 |
|  | LONG-TERM | CFB15 | 02/16/93 | 0 | YELLOW, CLEAR | 1.020 | 7 | 0 |
|  |  |  | 02/20/93 | 4 | YELLOW, CLEAR | 1.021 | 5 | 0 |
|  |  |  | 03/02/93 | 14 | YELLOW, CLEAR | 1.011 | 7 | 0 |
|  |  |  | 03/09/93 | 21 | YELLOW, CLEAR | 1.020 | 7 | 0 |

| VIRUS | NECROPSY | ANIMAL | DATE | DAY | Nitrite | Protein | Glucose | Ketones |
|---|---|---|---|---|---|---|---|---|
| 1.0E + 09 | 4 DAY | CFB11 | 02/16/93 | 0 | 0 | 100 | 0 | 0 |
|  |  |  | 02/20/93 | 4 | 0 | 15 | 0 | 0 |
|  | 21 DAY | CFB13 | 02/16/93 | 0 | 0 | 0 | 0 | 0 |
|  |  |  | 02/20/93 | 4 | 0 | 0 | 0 | 0 |
|  |  |  | 03/02/93 | 14 | 0 | 0 | 0 | 0 |
|  |  |  | 03/09/93 | 21 | 0 | 0 | 0 | 0 |
|  | LONG-TERM | CFB15 | 02/16/93 | 0 | 0 | 0 | 0 | 0 |
|  |  |  | 02/20/93 | 4 | 0 | 30 | 0 | 0 |
|  |  |  | 03/02/93 | 14 | 0 | 0 | 0 | 0 |
|  |  |  | 03/09/93 | 21 | 0 | 30 | 0 | 0 |

| VIRUS | NECROPSY | ANIMAL | DATE | DAY | Urobilin | Bilirubin | Blood | RBC/hpf |
|---|---|---|---|---|---|---|---|---|
| 1.0E + 09 | 4 day | cfb11 | 02/16/93 | 0 | 0 | 0 | 300 | 75 to 100 |
|  |  |  | 02/20/93 | 4 | 0 | 0 | 60 | 5 to 10 |
|  | 21 DAY | CFB13 | 02/16/93 | 0 | 0 | 0 | 0 | ND |
|  |  |  | 02/20/93 | 4 | 0 | 0 | 0 | ND |
|  |  |  | 03/02/93 | 14 | 0 | 0 | 0 | ND |
|  |  |  | 03/09/93 | 21 | 0 | 0 | 0 | ND |
|  | LONG-TERM | CFB15 | 02/16/93 | 0 | 0 | 0 | 0 | ND |
|  |  |  | 02/20/93 | 4 | 0 | 0 | 0 | occ |
|  |  |  | 03/02/93 | 14 | 0 | 0 | 0 | ND |
|  |  |  | 03/09/93 | 21 | 0 | 0 | 10 | 3 to 5 |

| VIRUS | NECROPSY | ANIMAL | DATE | DAY | WBC/hpf | Casts |
|---|---|---|---|---|---|---|
| 1.0E + 09 | 4 DAY | CFB11 | 02/16/93 | 0 | 3 to 5 | 0 |
|  |  |  | 02/20/93 | 4 | 0 to 3 | 0 |
|  | 21 DAY | CFB13 | 02/16/93 | 0 | ND | ND |
|  |  |  | 02/20/93 | 4 | ND | ND |
|  |  |  | 03/02/93 | 14 | ND | ND |
|  |  |  | 03/09/93 | 21 | ND | ND |
|  | LONG-TERM | CFB15 | 02/16/93 | 0 | ND | ND |
|  |  |  | 02/20/93 | 4 | 0 | 0 |
|  |  |  | 03/02/93 | 14 | ND | ND |
|  |  |  | 03/09/93 | 21 | 0 | 0 |

TABLE IVf

Urinalysis for Baboon Toxicity Studies (Study III)

| VIRUS | NECROPSY | ANIMAL | DATE | DAY | Urine | Specific gravity | pH | Leuk esterase |
|---|---|---|---|---|---|---|---|---|
| 1.0E + 10 | 4 DAY | CFB4 | 01/18/93 | 0 | YELLOW, CLEAR | 1.015 | 8 | 0 |
| | | | 01/22/93 | 4 | YELLOW, HAZY | 1.003 | 8 | 0 |
| | 21 DAY | CFB6 | 01/18/93 | 0 | YELLOW, CLOUDY | 1.023 | 8 | 0 |
| | | | 02/02/93 | 15 | YELLOW, HAZY | 1.017 | 7 | 0 |
| | | | 02/08/93 | 21 | YELLOW, CLEAR | 1.013 | 8 | 0 |
| | LONG-TERM | CFB8 | 01/22/93 | 4 | YELLOW, CLEAR | 1.008 | 8 | 0 |
| | | | 02/02/93 | 21 | YELLOW, HAZY | 1.018 | 7 | 0 |

| VIRUS | NECROPSY | ANIMAL | DATE | DAY | Nitrite | Protein | Glucose | Ketones |
|---|---|---|---|---|---|---|---|---|
| 1.0E + 10 | 4 DAY | CFB4 | 01/18/93 | 0 | 0 | 0 | 0 | 0 |
| | | | 01/22/93 | 4 | 0 | 0 | 0 | 0 |
| | 21 DAY | CFB6 | 01/18/93 | 0 | 0 | 0 | 0 | 0 |
| | | | 02/02/93 | 15 | 0 | 30 | 0 | 0 |
| | | | 02/08/93 | 21 | 0 | 0 | 0 | 0 |
| | LONG-TERM | CFB8 | 01/22/93 | 4 | 0 | 0 | 0 | 0 |
| | | | 02/02/93 | 21 | 0 | 15 | 0 | 0 |

| VIRUS | NECROPSY | ANIMAL | DATE | DAY | Urobilin | Bilirubin | Blood | RBC/hpf |
|---|---|---|---|---|---|---|---|---|
| 1.0E + 10 | 4 DAY | CFB4 | 01/18/93 | 0 | 0 | 0 | 0 | 0 |
| | | | 01/22/93 | 4 | 0 | 0 | 0 | ND |
| | 21 DAY | CFB6 | 01/18/93 | 0 | 0 | 0 | 0 | 10 to 25 |
| | | | 02/02/93 | 15 | 0 | 0 | 0 | occ |
| | | | 02/08/93 | 21 | 0 | 0 | 0 | ND |
| | LONG-TERM | CFB8 | 01/22/93 | 4 | 0 | 0 | 0 | ND |
| | | | 02/02/93 | 21 | 0 | 0 | 0 | occ |

| VIRUS | NECROPSY | ANIMAL | DATE | DAY | WBC/hpf | Casts |
|---|---|---|---|---|---|---|
| 1.0E + 10 | 4 DAY | CFB4 | 01/18/93 | 0 | occ | 0 |
| | | | 01/22/93 | 4 | ND | ND |
| | 21 DAY | CFB6 | 01/18/93 | 0 | occ | 0 |
| | | | 02/02/93 | 15 | 3 to 5 | 0 |
| | | | 02/08/93 | 21 | ND | ND |
| | LONG-TERM | CFB8 | 01/22/93 | 4 | ND | ND |
| | | | 02/02/93 | 21 | occ | 0 |

TABLE V

Arterial Blood Gases for Baboon Toxicity Studies

| | VIRUS | NECROPSY | ANIMAL | DATE | DAY | pH | PCO$_2$ | PO$_2$ | HCO$_3$ calc | P(A-a)O$_2$ | ΔP(A-a)O$_2$ |
|---|---|---|---|---|---|---|---|---|---|---|---|
| STUDY III | 1.0E + 08 | 4 DAY | CFB10 | 02/03/93 | −13 | 7.29 | 41.2 | 84.0 | 19.8 | 14.5 | 0.0 |
| | | | | 02/10/93 | −6 | 7.33 | 43.3 | 64 | 28.2 | 9.2 | −5.3 |
| | | | | 02/16/93 | 0 | 7.39 | 46.3 | 80.0 | 28.2 | 9.2 | −5.3 |
| | | | | 02/20/93 | 4 | 7.38 | 46.1 | 78.0 | 27.3 | 12.1 | −2.4 |
| | | 21 DAY | CFB14 | 01/29/93 | −18 | 7.37 | 43.8 | 76.0 | 25.6 | 16.7 | 2.0 |
| | | | | 02/16/93 | 0 | 7.40 | 44.1 | 77.0 | 27.3 | 14.7 | 0.0 |
| | | | | 02/20/93 | 4 | 7.38 | 44.3 | 83.0 | 26.5 | 9.4 | −5.3 |
| | | | | 03/02/93 | 14 | 7.35 | 43.8 | 72.0 | 24.5 | 19.8 | 5.1 |
| | | | | 03/09/93 | 21 | 7.37 | 47.3 | 67.0 | 27.4 | 21.7 | 7.0 |
| | | LONG-TERM | CFB16 | 01/29/93 | −18 | 7.28 | 34.9 | 89.0 | 16.6 | 14.8 | −4.5 |
| | | | | 02/16/93 | 0 | 7.37 | 42.1 | 76 | 24.6 | 19.3 | 0.0 |
| | | | | 02/20/93 | 4 | 7.37 | 41.6 | 80 | 24.3 | 15.9 | −3.4 |
| | | | | 03/02/93 | 14 | 7.42 | 38.9 | 78 | 25.5 | 20.1 | 0.8 |
| | | | | 03/09/93 | 21 | 7.40 | 39.7 | 87 | 25.1 | 11.2 | −8.1 |
| | | | | 04/10/93 | 53 | 7.41 | 40.9 | 76 | 25.9 | 19.7 | 0.4 |
| | 1.0E + 09 | 4 DAY | CFB11 | 02/03/93 | −13 | 7.20 | 42.0 | 84.0 | 16.6 | 12.7 | 6.6 |
| | | | | 02/16/93 | 0 | 7.15 | 39.9 | 90.0 | 14.3 | 6.1 | 0.0 |
| | | | | 02/20/93 | 4 | 7.32 | 46.6 | 67.0 | 24.4 | 22.4 | 16.3 |
| | | 21 DAY | CFB13 | 01/29/93 | −18 | 7.41 | 42.6 | 83.0 | 27.2 | 11.2 | 1.9 |
| | | | | 02/16/93 | 0 | 7.38 | 43.7 | 83.0 | 26.4 | 9.3 | 0.0 |
| | | | | 02/20/93 | 4 | 7.37 | 46.0 | 74.0 | 27.2 | 16.2 | 6.9 |
| | | | | 03/02/93 | 14 | 7.38 | 44.4 | 82.0 | 26.8 | 9.5 | 0.2 |
| | | | | 03/09/93 | 21 | 7.40 | 47.5 | 80.0 | 29.5 | 8.0 | −1.3 |
| | | LONG-TERM | CFB15 | 02/03/93 | −13 | 7.30 | 41.1 | 87.0 | 21.4 | 10.5 | 6.5 |
| | | | | 02/16/93 | 0 | 7.28 | 36.7 | 98.0 | 17.4 | 4.0 | 0.0 |
| | | | | 02/20/93 | 4 | 7.29 | 38.4 | 83.0 | 18.5 | 16.6 | 12.6 |
| | | | | 03/02/93 | 14 | 7.39 | 40.8 | 80.0 | 24.9 | 15.8 | 11.8 |
| | | | | 03/09/93 | 21 | 7.32 | 37.7 | 91.0 | 19.6 | 8.9 | 4.9 |

TABLE V-continued

Arterial Blood Gases for Baboon Toxicity Studies

| VIRUS | NECROPSY | ANIMAL | DATE | DAY | pH | $PCO_2$ | $PO_2$ | $HCO_3$ calc | $P(A-a)O_2$ | $\Delta P(A-a)O_2$ |
|---|---|---|---|---|---|---|---|---|---|---|
| | | | 04/10/93 | 53 | 7.37 | 40.2 | 84.0 | 23.2 | 12.6 | 8.6 |
| NORMAL ADULT BABOON | | | | | N/A | N/A | N/A | N/A | N/A | |
| NORMAL JUVENILE BABOON | | | | | | | | | | |
| STUDY I  1.0E + 10 | 4 DAY | CFB1 | 10/20/92 | −2 | 7.39 | 55.4 | 54.0 | 33.9 | 26.2 | |
| | | | 10/20/92 | −2 | 7.39 | 54.6 | 58.0 | 33.5 | 22.4 | |
| | | | 10/22/92 | 0 | 7.39 | 54.7 | 54.0 | | | |
| STUDY II  1.0E + 10 | LONG-TERM | CFB2 | 11/06/92 | −3 | 7.38 | 45.0 | 62.0 | 27.0 | 30.3 | 3.7 |
| | | | 11/09/92 | 0 | 7.35 | 45.0 | 63.0 | 26.9 | 26.6 | 0.0 |
| | | | 11/12/92 | 3 | 7.34 | 51.0 | 54.0 | 28.1 | 27.4 | 0.8 |
| | | | 11/23/92 | 14 | 7.39 | 46.0 | 58.0 | 27.8 | 31.3 | 4.7 |
| | | | 11/30/92 | 21 | 7.36 | 52.0 | 44.0 | 29.2 | 39.2 | 12.6 |
| | | | 02/10/93 | 93 | 7.38 | 47.5 | 56.0 | 28.5 | 33.1 | 6.5 |
| | | | 03/05/93 | 116 | 7.38 | 48.5 | 63.0 | 29.0 | 22.7 | −3.9 |
| | | | 04/10/93 | 152 | 7.34 | 51.6 | 47.0 | 28.4 | 35.4 | 8.8 |
| STUDY III  1.0E + 07 | 4 DAY | CFB3 | 01/18/93 | 0 | 7.39 | 49.0 | 89.0 | 30.1 | −3.3 | 0.0 |
| | | | 01/22/93 | 4 | 7.40 | 48.2 | 86.0 | 30.4 | 0.9 | 4.2 |
| | 21 DAY | CFB5 | 01/18/93 | 0 | 7.40 | 47.0 | 74.0 | 29.6 | 14.7 | 0.0 |
| | | | 01/22/93 | 4 | 7.40 | 46.6 | 63.0 | 29.4 | 23.4 | 8.7 |
| | | | 02/02/93 | 15 | 7.38 | 49.0 | 86.0 | 29.5 | 0.4 | −14.3 |
| | | | 02/08/93 | 21 | 7.41 | 46.2 | 104.0 | 30.0 | 15.6 | 0.9 |
| | LONG-TERM | CFB7 | 01/18/93 | 0 | 7.41 | 41.8 | 82.0 | 27.0 | 13.4 | 0.0 |
| | | | 01/22/93 | 4 | 7.41 | 51.0 | 63.0 | 32.6 | 20.5 | 7.1 |
| | | | 02/02/93 | 15 | 7.37 | 49.3 | 39.0 | 28.7 | 46.6 | 33.2 |
| | | | 02/08/93 | 21 | 7.39 | 49.8 | 67.0 | 30.4 | 20.1 | 6.7 |
| | | | 03/10/93 | 51 | 7.38 | 51.8 | 67.0 | 31.2 | 14.9 | 1.5 |
| | | | 04/10/93 | 82 | 7.42 | 46.5 | 83.0 | 30.1 | 6.1 | −7.3 |
| STUDY III  1.0E + 08 | 4 DAY | CFB10 | 02/03/93 | −13 | 7.29 | 41.2 | 84.0 | 19.8 | 14.5 | 0.0 |
| | | | 02/10/93 | −6 | 7.33 | 43.3 | 64 | 28.2 | 9.2 | −5.3 |
| | | | 02/16/93 | 0 | 7.39 | 46.3 | 80.0 | 28.2 | 9.2 | −5.3 |
| | | | 02/20/93 | 4 | 7.38 | 46.1 | 78.0 | 27.3 | 12.1 | −2.4 |
| | 21 DAY | CFB14 | 01/29/93 | −18 | 7.37 | 43.8 | 76.0 | 25.6 | 16.7 | 2.0 |
| | | | 02/16/93 | 0 | 7.40 | 44.1 | 77.0 | 27.3 | 14.7 | 0.0 |
| | | | 02/20/93 | 4 | 7.38 | 44.3 | 83.0 | 26.5 | 9.4 | −5.3 |
| | | | 03/02/93 | 14 | 7.35 | 43.8 | 72.0 | 24.5 | 19.8 | 5.1 |
| | | | 03/09/93 | 21 | 7.37 | 47.3 | 67.0 | 27.4 | 21.7 | 7.0 |
| | LONG-TERM | CFB16 | 01/29/93 | −18 | 7.28 | 34.9 | 89.0 | 16.6 | 14.8 | −4.5 |
| | | | 02/16/93 | 0 | 7.37 | 42.1 | 76 | 24.6 | 19.3 | 0.0 |
| | | | 02/20/93 | 4 | 7.37 | 41.6 | 80 | 24.3 | 15.9 | −3.4 |
| | | | 03/02/93 | 14 | 7.42 | 38.9 | 78 | 25.5 | 20.1 | 0.8 |
| | | | 03/09/93 | 21 | 7.40 | 39.7 | 87 | 25.1 | 11.2 | −8.1 |
| | | | 04/10/93 | 53 | 7.41 | 40.9 | 76 | 25.9 | 19.7 | 0.4 |
| 1.0E + 09 | 4 DAY | CFB11 | 02/03/93 | −13 | 7.20 | 42.0 | 84.0 | 16.6 | 12.7 | 6.6 |
| | | | 02/16/93 | 0 | 7.15 | 39.9 | 90.0 | 14.3 | 6.1 | 0.0 |
| | | | 02/20/93 | 4 | 7.32 | 46.6 | 67.0 | 24.4 | 22.4 | 16.3 |
| | 21 DAY | CFB13 | 01/29/93 | −18 | 7.41 | 42.6 | 83.0 | 27.2 | 11.2 | 1.9 |
| | | | 02/16/93 | 0 | 7.38 | 43.7 | 83.0 | 26.4 | 9.3 | 0.0 |
| | | | 02/20/93 | 4 | 7.37 | 46.0 | 74.0 | 27.2 | 16.2 | 6.9 |
| | | | 03/02/93 | 14 | 7.38 | 44.4 | 82.0 | 26.8 | 9.5 | 0.2 |
| | | | 03/09/93 | 21 | 7.40 | 47.5 | 80.0 | 29.5 | 8.0 | −1.3 |
| | LONG-TERM | CFB15 | 02/03/93 | −13 | 7.30 | 41.1 | 87.0 | 21.4 | 10.5 | 6.5 |
| | | | 02/16/93 | 0 | 7.28 | 36.7 | 98.0 | 17.4 | 4.0 | 0.0 |
| | | | 02/20/93 | 4 | 7.29 | 38.4 | 83.0 | 18.5 | 16.6 | 12.6 |
| | | | 03/02/93 | 14 | 7.39 | 40.8 | 80.0 | 24.9 | 15.8 | 11.8 |
| | | | 03/09/93 | 21 | 7.32 | 37.7 | 91.0 | 19.6 | 8.9 | 4.9 |
| | | | 04/10/93 | 53 | 7.37 | 40.2 | 84.0 | 23.2 | 12.6 | 8.6 |
| STUDY III  1.0E + 10 | 4 DAY | CFB4 | 01/18/93 | 0 | 7.40 | 47.0 | 78.0 | 29.3 | 10.9 | 0.0 |
| | | | 01/22/93 | Specimen | Clotted | | | | | |
| | 21 DAY | CFB6 | 01/18/93 | 0 | 7.41 | 45.3 | 72.0 | 29.1 | 18.8 | 0.0 |
| | | | 01/22/93 | 4 | 7.35 | 42.9 | 59.0 | 23.7 | 34.0 | 15.2 |
| | | | 02/02/93 | 15 | 7.40 | 47.1 | 66.0 | 29.4 | 22.8 | 4.0 |
| | | | 02/08/93 | 21 | 7.38 | 48.5 | 59.0 | 28.8 | 29.0 | 10.2 |
| | LONG-TERM | CFB8 | 01/18/93 | 0 | 7.35 | 44.0 | 78.0 | 24.8 | 15.0 | 0.0 |
| | | | 01/22/93 | 4 | 7.42 | 42.6 | 66.0 | 28.2 | 27.0 | 12.0 |
| | | | 02/02/93 | 15 | 7.41 | 41.6 | 77.0 | 26.3 | 18.2 | 3.2 |
| | | | 02/08/93 | 21 | 7.34 | 43.2 | 70.0 | 23.5 | 25.0 | 10.0 |
| | | | 03/10/93 | 51 | 7.40 | 47.4 | 51.0 | 29.9 | 36.5 | 21.5 |
| | | | 03/15/93 | 56 | 7.38 | 43.0 | 63.0 | 25.7 | 32.4 | 17.4 |
| | | | 03/24/93 | 65 | 7.36 | 45.4 | 70.0 | 25.9 | 21.1 | 6.1 |
| | | | 04/10/93 | 82 | 7.36 | 43.7 | 64.0 | 24.9 | 27.7 | 12.7 |

TABLE VI

| | | | | Chest Radiographs for Baboon Toxicity Studies | | |
|---|---|---|---|---|---|---|
| | VIRAL DOS | NECROPSY | ANIMAL | DATE | DAY | CHEST RADIOGRAPHIC FINDINGS |
| STUDY I | 1.0E + 10 | 4 DAY | CFB1 | 10/20/92 | −2 | RUL AND RML atelectasis |
| STUDY II | 1.0E + 10 | LONG-TERM | CFB2 | 11/06/92 | −3 | Normal |
| | | | | 11/09/92 | 0 | ± RUL and mild LUL densities |
| | | | | 11/12/92 | 3 | mild-moderate RUL and mild LUL densities |
| | | | | 11/23/92 | 14 | mild RUL and mild LUL densities |
| | | | | 01/21/93 | 73 | Normal |
| | | | | 01/25/93 | 77 | Normal |
| | | | | 02/10/93 | 93 | Normal |
| | | | | 03/05/93 | 116 | Normal |
| | | | | 04/10/93 | 152 | Normal |
| STUDY III | 1.0E + 07 | 4 DAY | CFB3 | 01/18/93 | 0 | Normal |
| | | | | 01/22/93 | 4 | Normal |
| | | 21 DAY | CFB5 | 01/18/93 | 0 | Normal |
| | | | | 01/22/93 | 4 | Normal |
| | | | | 02/02/93 | 15 | Normal |
| | | | | 02/08/93 | 21 | Normal |
| | | LONG-TERM | CFB7 | 01/18/93 | 0 | linear streaking of medial aspect of lower lobes bilaterally |
| | | | | 01/22/93 | 4 | linear streaking of medial aspect of lower lobes bilaterally |
| | | | | 02/02/93 | 15 | linear streaking of medial aspect of lower lobes bilaterally |
| | | | | 02/08/93 | 21 | linear streaking of medial aspect of lower lobes bilaterally |
| | | | | 03/10/93 | 51 | bilateral medial lower lobes with prominent markings |
| | | | | 04/10/93 | 82 | Normal |
| STUDY III | 1.0E + 08 | 4 DAY | CFB10 | 02/03/93 | −13 | ND |
| | | | | 02/10/93 | −6 | ND |
| | | | | 02/16/93 | 0 | Normal |
| | | | | 02/20/93 | 4 | Normal |
| | | 21 DAY | CFB14 | 01/03/93 | −44 | Normal |
| | | | | 01/29/93 | −18 | ND |
| | | | | 02/16/93 | 0 | blurred L hemi-diaphragm on A-P (heart overlying), Lateral is normal |
| | | | | 02/20/93 | 4 | blurred L hemi-diaphragm on A-P, Lateral is normal, improved |
| | | | | 03/02/93 | 14 | blurred L hemi-diaphragm on A-P, Lateral is normal, improved |
| | | | | 03/09/93 | 21 | Normal |
| | | LONG-TERM | CFB16 | 01/03/93 | −44 | Normal |
| | | | | 01/29/93 | −18 | Normal |
| | | | | 02/16/93 | 0 | Normal |
| | | | | 02/20/93 | 4 | Normal |
| | | | | 03/09/93 | 21 | Normal |
| | | | | 04/10/93 | 53 | Normal |
| | 1.0E + 0.9 | 4 DAY | CFB11 | 02/16/93 | 0 | Normal |
| | | | | 02/20/93 | 4 | Normal |
| | | 21 DAY | CFB13 | 01/03/93 | −44 | very mild RLL density |
| | | | | 02/16/93 | 0 | Normal |
| | | | | 02/20/93 | 4 | Normal |
| | | | | 03/02/93 | 14 | Normal |
| | | | | 03/09/93 | 21 | Normal |
| STUDY III | 1.0E + 09 | LONG-TERM | CFB16 | 01/03/93 | −44 | mild LUL streaking, bilateral medial lower lobes with prominent markings |
| | | | | 02/16/93 | 0 | mild LUL streaking, bilateral medial lower lobes with prominent markings |
| | | | | 02/20/93 | 4 | mild LUL streaking, bilateral medial lower lobes with prominent markings |
| | | | | 03/02/93 | 14 | Normal |
| | | | | 03/09/93 | 21 | Normal |
| | | | | 04/10/93 | 53 | Normal |
| | 1.0E + 10 | 4 DAY | CFB4 | 01/18/93 | 0 | Normal |
| | | | | 01/22/93 | 4 | Normal |
| | | 21 DAY | CFB6 | 01/18/93 | 0 | Normal |
| | | | | 01/22/93 | 4 | ± RUL density |
| | | | | 02/02/93 | 15 | severe RUL, moderate LUL, and ± RLL density |
| | | | | 02/08/93 | 21 | moderately severe RUL, mild LUL, and moderate RLL densities |
| | | LONG-TERM | CFB8 | 01/18/93 | 0 | Normal |
| | | | | 01/22/93 | 4 | mild LUL density |
| | | | | 02/02/93 | 15 | mild-moderate RUL and improved LUL densities |
| | | | | 02/08/93 | 21 | moderate RUL and improved LUL densities |
| | | | | 02/18/93 | 31 | normal RUL, mild LUL |
| | | | | 02/26/93 | 39 | Normal |
| | | | | 03/10/93 | 51 | Normal |

| Date | | |
|---|---|---|
| 03/15/93 | 56 | moderate density in region of RUL/RML |
| 03/24/93 | 65 | Normal |
| 04/10/93 | 82 | Normal |

TABLE VII

Analysis of Bronchoalveolar Lavage

| | VIRUS | NECROPSY | ANIMAL | DAY | LOCATION | TOTAL CELL COUNT | % X-Gal | % CFTR | DIFFERENTIAL COUNT | | | |
|---|---|---|---|---|---|---|---|---|---|---|---|---|
| | | | | | | | | | % Macro | % PMN | % Eos | % Lymph |
| NORMAL HUMAN | | | | | | | | | 84–99 | 0.1–4.4 | N/A | 0.7–14.4 |
| NORMAL SIMIAN | | | | | | | | | 87.8–96.2 | 0–2 | 0–0.5 | 2.8–11.2 |
| STUDY II | 1.0E+10 | LONG-TERM | CFB2 | 0 | Right Middle Lobe | 4.20E+06 | 0 | 0 | 43 | 45 | 7 | 4 |
| | | | | 3 | LacZ Segment | 2.50E+06 | 5.2 | 0 | 58 | 14 | 5 | 22 |
| | | | | 3 | CFTR Segment | 4.00E+06 | 0.3 | 3.4 | 38 | 52 | 2 | 7 |
| | | | | 21 | LacZ Segment | 3.60E+06 | 0 | ND | 73 | 7 | 8 | 12 |
| | | | | 21 | CFTR Segment | 2.90E+06 | 0 | ND | 46 | 5 | 16 | 33 |
| STUDY III | 1.0E+07 | LONG-TERM | CFB7 | 0 | Right MIddle Lobe | 2.00E+06 | 0 | ND | 87 | 2 | 1 | 11 |
| | | | | 4 | LacZ Segment | 2.66E+06 | 0 | ND | 54 | 33 | 2 | 11 |
| | | | | 4 | CFTR Segment | 2.25E+06 | 0 | ND | 80 | 7 | 5 | 8 |
| | | | | 21 | LacZ Segment | 2.50E+06 | 0 | ND | 60 | 1 | 1 | 38 |
| | | | | 21 | CFTR Segment | 3.80E+06 | 0 | ND | 83 | 2 | 2 | 13 |
| | 1.0E+08 | LONG-TERM | CFB16 | 0 | RIght Middle Lobe | 2.20E+06 | 0 | ND | 48 | 2 | 1 | 49 |
| | | | | 4 | LacZ Segment | 2.00E+06 | 0 | ND | 67 | 3 | 1 | 29 |
| | | | | 4 | CFTR Segment | 1.80E+06 | 0 | ND | 55 | 3 | 2 | 40 |
| | | | | 21 | LacZ Segment | 1.00E+06 | 0 | ND | 31 | 0 | 3 | 68 |
| | | | | 21 | CFTR Segment | 7.00E+05 | 0 | ND | 62 | 0 | 5 | 33 |
| | 1.0E+09 | LONG- | CFB15 | 0 | Right Middle Lobe | 1.50E+06 | 0 | ND | 68 | 5 | 5 | 22 |
| | | | | 4 | LacZ Segment | 3.00E+06 | 0 | ND | 60 | 29 | 8 | 4 |
| | | | | 4 | CFTR Segment | 2.50E+06 | 0 | ND | 48 | 34 | 12 | 7 |
| | | | | 21 | LacZ Segment | 5.00E+05 | 0 | ND | 41 | 0 | 18 | 41 |
| | | | | 21 | CFTR Segment | 4.00E+05 | 0 | ND | 50 | 0 | 5 | 45 |
| | 1.0E+10 | LONG-TERM | CFB8 | 0 | Right Middle Lobe | 1.70E+06 | 0 | ND | 73 | 3 | 9 | 15 |
| | | | | 4 | LacZ Segment | 2.45E+06 | 1.5 | ND | 22 | 13 | 55 | 10 |
| | | | | 4 | CFTR Segment | 2.25E+06 | 0 | ND | 50 | 4 | 16 | 29 |
| | | | | 21 | LacZ Segment | 1.80E+06 | 0 | ND | 39 | 2 | 10 | 48 |
| | | | | 21 | CFTR Segment | 2.50E+06 | 0 | ND | 28 | 2 | 53 | 16 |

| | VIRUS | Total Counted | Macrophages | PMN | EOS | Lymph | Epith | tot cell-epith | DIFFERENTIAL COUNT | | | | |
|---|---|---|---|---|---|---|---|---|---|---|---|---|---|
| | | | | | | | | | % Macro | % PMN | % Eos | % Lymph | % Epith |
| STUDY II | 1.0E+10 | 443 | | | | | | | 41.8 | 44.0 | 6.8 | 4.3 | 3.2 |
| | | 1017 | | | | | | | 53.7 | 13.1 | 4.9 | 20.1 | 8.3 |
| | | 1276 | | | | | | | 36.9 | 50.7 | 2.4 | 6.8 | 3.2 |
| | | 522 | | | | | | | 63.4 | 5.9 | 6.7 | 10.5 | 13.4 |

TABLE VII-continued

Analysis of Bronchoalveolar Lavage

| | | | | | | | | | | | | |
|---|---|---|---|---|---|---|---|---|---|---|---|---|
| | | 532 | | | | | | 42.1 | 4.7 | 30.6 | 7.7 | |
| STUDY III | 1.0E+0.7 | 600 | 509 | 11 | 4 | 64 | 12 | 84.8 | 1.8 | 0.7 | 10.7 | 2.0 |
| | | 600 | 302 | 183 | 11 | 64 | 40 | 50.3 | 30.5 | 1.8 | 10.7 | 6.7 |
| | | 600 | 440 | 39 | 27 | 44 | 50 | 73.3 | 6.5 | 4.5 | 7.3 | 8.3 |
| | | 512 | 280 | 6 | 4 | 174 | 48 | 54.7 | 1.2 | 0.8 | 34.0 | 9.4 |
| | | 551 | 424 | 8 | 10 | 67 | 45 | 77.0 | 1.5 | 1.8 | 12.2 | 8.2 |
| | 1.0E+08 | 562 | 253 | 12 | 4 | 260 | 34 | 528 | | | | |
| | | 604 | 394 | 18 | 8 | 170 | 14 | 590 | | | | |
| | | 520 | 267 | 15 | 11 | 197 | 33 | 487 | | | | |
| | | 634 | 190 | 1 | 16 | 410 | 17 | 617 | | | | |
| | | 533 | 318 | 2 | 25 | 168 | 20 | 513 | | | | |
| | 1.0E+09 | 500 | 330 | 25 | 24 | 109 | 13 | 487 | | | | |
| | | 597 | 356 | 170 | 46 | 23 | 3 | 594 | | | | |
| | | 555 | 263 | 190 | 64 | 36 | 3 | 552 | | | | |
| | | 633 | 253 | 0 | 111 | 254 | 15 | 618 | | | | |
| | | 597 | 242 | 1 | 24 | 221 | 109 | 488 | | | | |
| | 1.0E+10 | 600 | 434 | 17 | 55 | 87 | 7 | 72.3 | 2.8 | 9.2 | 14.5 | 1.2 |
| | | 600 | 134 | 75 | 325 | 62 | 4 | 22.3 | 12.5 | 54.2 | 10.3 | 0.7 |
| | | 600 | 289 | 25 | 95 | 170 | 21 | 48.2 | 4.2 | 15.8 | 28.3 | 3.5 |
| | | 674 | 246 | 15 | 64 | 304 | 45 | 36.5 | 2.2 | 9.5 | 45.1 | 6.7 |
| | | 554 | 156 | 13 | 294 | 90 | 1 | 28.2 | 2.3 | 53.1 | 16.2 | 0.2 |

TABLE VIII

Analysis of Bronchial Brushings

| | VIRUS | NECROPSY | ANIMAL | DAY | LOCATION | TOTAL CELL COUNT | % X-Gal | % CFTR |
|---|---|---|---|---|---|---|---|---|
| STUDY I | 1.0E+10 | 4 DAY | CFB1 | ND | | | | |
| STUDY II | 1.0E+10 | LONG-TERM | CFB2 | 0 | Right Middle Lobe | 2.4E+06 | 0 | 0 |
| | | | | 3 | LacZ Segment | 6.2E+05 | 0 | 0 |
| | | | | 3 | CFTR Segment | 5.6E+05 | 0 | 2.1 |
| | | | | 21 | LacZ Segment | 3.6E+06 | 0 | ND |
| | | | | 21 | CFTR Segment | 3.0E+06 | 0 | ND |
| STUDY III | 1.0E+07 | 4 DAY | CFB3 | ND | | | | |
| | | 21 DAY | CFB5 | ND | | | | |
| | | LONG-TERM | CFB7 | 0 | Left Lower Lobe | 1.0E+06 | 0 | 0 |
| | | | | 4 | LacZ Segment | 1.0E+06 | 0 | 0 |
| | | | | 4 | CFTR Segment | 1.0E+06 | 0 | 0 |
| | | | | 21 | LacZ Segment | 8.5E+05 | 0 | 0 |
| | | | | 21 | CFTR Segment | 6.9E+05 | 0 | 0 |
| | 1.0E+08 | 4 DAY | CFB10 | ND | | | | |
| | | 21 DAY | CFB14 | ND | | | | |
| | | LONG-TERM | CFB16 | 0 | Left Lower Lobe | 1.0E+06 | 0 | 0 |
| | | | | 4 | LacZ Segment | 9.2E+05 | 0 | 0 |
| | | | | 4 | CFTR Segment | 1.2E+06 | 0 | 0 |
| | | | | 21 | LacZ Segment | 1.2E+06 | 0 | 0 |
| | | | | 21 | CFTR Segment | 2.0E+06 | 0 | 0 |
| | 1.0E+09 | 4 DAY | CFB11 | ND | | | | |
| | | 21 DAY | CFB13 ND | | | | | |
| | | LONG-TERM | CFB15 | 0 | Left Lower Lobe | 1.6E+06 | 0 | 0 |
| | | | | 4 | LacZ Segment | 1.2E+06 | 0 | 0 |
| | | | | 4 | CFTR Segment | 8.9E+05 | 0 | 0 |
| | | | | 21 | LacZ Segment | 1.5E+06 | 0 | 0 |
| | | | | 21 | CFTR Segment | 1.8E+06 | 0 | 0 |
| | 1.0E+10 | 4 DAY | CFB4 | ND | | | | |
| | | 21 DAY | CFB6 | ND | | | | |
| | | LONG-TERM | CFB8 | 0 | Left Lower Lobe | 1.2E+06 | 0 | 0 |
| | | | | 4 | LacZ Segment | 1.0E+06 | 5 | 0 |
| | | | | 4 | CFTR Segment | 1.3E+06 | 0 | 2.5 |
| | | | | 21 | LacZ Segment | 1.3E+06 | 0 | 0 |
| | | | | 21 | CFTR Segment | 1.2E+06 | 0 | 0 |

TABLE IX

LacZ Adenovirus Assay Results

X-GAL
(Scale: −, ±, +, ++, +++)
BODY FLUID TYPE

| | VIRUS | NECROPSY | ANIMAL | DAY | NASAL | BLOOD | URINE | RECTAL | MIDDLE LOBE | LacZ SEGMENT (LAVAGE) | CFTR SEGMENT |
|---|---|---|---|---|---|---|---|---|---|---|---|
| STUDY I | 1.0E+10 | 4 DAY | CFB1 | — | | | | | | | |
| STUDY II | 1.0E+10 | LONG-TERM | CFB2 | 0 | | | | | | | |
| | | | | 3 | − | − | − | − | − | + | |
| | | | | 14 | − | − | − | − | − | − | − |
| | | | | 21 | − | − | − | − | − | − | − |
| STUDY III | 1.0E+07 | 4 DAY | CFB3 | 0 | | | | | | | |
| | | | | 4 | − | − | − | − | − | − | |
| | | 21 DAY | CFB5 | 0 | | | | | | | |
| | | | | 4 | − | − | − | − | | | |
| | | | | 15 | | | | | | | |
| | | | | 21 | − | − | − | − | − | − | − |
| | | LONG-TERM | CFB7 | 0 | | | | | | | |
| | | | | 4 | − | − | − | − | | | |
| | | | | 15 | | | | | | | |
| | | | | 21 | − | − | − | − | − | − | |
| | 1.0E+08 | 4 DAY | CFB10 | 0 | | | | | | | |
| | | | | 4 | − | − | − | − | − | − | |
| | | 21 DAY | CFB14 | 0 | | | | | | | |
| | | | | 4 | − | − | − | − | | | |
| | | LONG-TERM | CFB16 | 0 | | | | | | | |
| | | | | 4 | − | − | − | − | − | − | − |
| STUDY III | 1.0E+09 | 4 DAY | CFB11 | 0 | | | | | | | |
| | | | | 4 | − | − | − | − | | | |
| | | 21 DAY | CFB13 | 0 | | | | | | | |
| | | | | 4 | − | − | − | − | | | |
| | | LONG-TERM | CFB15 | 0 | | | | | | | |
| | | | | 4 | − | − | − | − | − | − | |
| | 1.0E+10 | 4 DAY | CFB4 | 0 | | | | | | | |
| | | | | 4 | − | − | − | − | | | |
| | | 21 DAY | CFB6 | 0 | | | | | | | |
| | | | | 4 | − | − | − | − | | | |
| | | | | 15 | | | | | | | |
| | | | | 21 | − | − | − | − | − | − | − |
| | | LONG-TERM | CFB8 | 0 | | | | | | | |
| | | | | 4 | − | − | − | − | | | |
| | | | | 15 | | | | | | | |
| | | | | 21 | − | − | − | − | − | − | − |

TABLE IX

| Addendum - LacZ Adenovirus Positive Control Study Results | | | | | | | |
|---|---|---|---|---|---|---|---|
| | | \multicolumn{6}{c}{X-GAL (Scale: −, ±, +, ++, +++) Particles per Plate} | | | | | |
| DATE | DAY | 10,000 | 1,000 | 100 | 10 | 1 | 0 |
| CFB3–CFB8 | | | | | | | |
| 01/17/89 | 0 | +++ | ++ | + | ± | − | − |
| 01/21/89 | 4 | +++ | ++ | + | ± | − | − |
| 02/01/89 | 15 | ND | ++ | + | ± | − | − |
| 02/07/89 | 21 | ND | ND | ± | − | − | − |
| CFB10–CFB16 | | | | | | | |
| 02/15/89 | 0 | ND | + | + | ± | − | − |

TABLE X

General Adenovirus Assay Results

|  | VIRUS | NECROPSY | ANIMAL | DAY | BODY FLUID AMOUNT | NASAL | BLOOD | URINE | RECTA | CYTOPATHIC EFFECT (Scale: −, ±, +) RIGHT MIDDLE LOBE | LAVAGE LacZ SEGMENT | CFTR SEGMENT |
|---|---|---|---|---|---|---|---|---|---|---|---|---|
| STUDY I | 1.0E+10 | 4 DAY | CFB1 | — | ND | | | | | | | |
| STUDY II | 1.0E+10 | LONG-TERM | CFB2 | — | ND | | | | | | | |
| STUDY III | 1.0E+07 | 4 DAY | CFB3 | 0 | 10 μl of body fluid | − | − | − | − | | | |
|  |  |  |  |  | 100 μl of body fluid | − | − | − | − | | | |
|  |  |  |  | 4 | 10 μl of body fluid | − | − | − | − | | | |
|  |  |  |  |  | 100 μl of body fluid | − | − | − | − | | | |
|  |  | 21 DAY | CFB5 | 0 | 10 μl of body fluid | − | − | − | − | | | |
|  |  |  |  |  | 100 μl of body fluid | − | − | − | − | | | |
|  |  |  |  | 4 | 10 μl of body fluid | − | − | − | − | | | |
|  |  |  |  |  | 100 μl of body fluid | − | − | − | − | | | |
|  |  |  |  | 15 | 10 μl of body fluid | − | − | − | − | | | |
|  |  |  |  |  | 100 μl of body fluid | − | − | − | − | | | |
|  |  |  |  | 21 | 10 μl of body fluid | − | − | − | − | | | |
|  |  |  |  |  | 100 μl of body fluid | − | − | − | − | | | |
|  |  | LONG-TERM | CFB7 | 0 | 10 μl of body fluid | − | − | − | − | | | |
|  |  |  |  |  | 100 μl of body fluid | − | − | − | − | − | − | − |
|  |  |  |  | 4 | 10 μl of body fluid | − | − | − | − | | | |
|  |  |  |  |  | 100 μl of body fluid | − | − | − | − | | | |
|  |  |  |  | 15 | 10 μl of body fluid | − | − | − | − | | | |
|  |  |  |  |  | 100 μl of body fluid | − | − | − | − | | | |
| STUDY III |  |  |  | 21 | 10 μl of body fluid | − | − | − | − | | | |
|  |  |  |  |  | 100 μl of body fluid | − | − | − | − | − | − | − |
|  | 1.0E+08 | 4 DAY | CFB10 | 0 | 10 μl of body fluid | − | − | − | − | | | |
|  |  |  |  |  | 100 μl of body fluid | − | − | − | − | | | |
|  |  |  |  | 4 | 10 μl of body fluid | − | − | − | − | | | |
|  |  |  |  |  | 100 μl of body fluid | − | − | − | − | | | |
|  |  | 21 DAY | CFB14 | 0 | 10 μl of body fluid | − | − | − | − | | | |
|  |  |  |  |  | 100 μl of body fluid | − | − | − | − | | | |
|  |  |  |  | 4 | 10 μl of body fluid | − | − | − | − | | | |
|  |  |  |  |  | 100 μl of body fluid | − | − | − | − | | | |
|  |  | LONG-TERM | CFB16 | 0 | 10 μl of body fluid | − | − | − | − | | | |
|  |  |  |  |  | 100 μl of body fluid | − | − | − | − | − | − | − |
|  | 1.0E+09 | 4 DAY | CFB11 | 0 | 10 μl of body fluid | − | − | − | − | | | |
|  |  |  |  |  | 100 μl of body fluid | − | − | − | − | | | |
|  |  |  |  | 4 | 10 μl of body fluid | − | − | − | − | | | |
|  |  |  |  |  | 100 μl of body fluid | − | − | − | − | | | |
| STUDY III |  | 21 DAY | CFB13 | 0 | 10 μl of body fluid | − | − | − | − | | | |

TABLE X-continued

General Adenovirus Assay Results

| | | | | | | | | | CYTOPATHIC EFFECT | | |
|---|---|---|---|---|---|---|---|---|---|---|---|
| | | | | | | | | | (Scale: −, ±, +) | | |
| | | | | | | | | | | LAVAGE | |
| VIRUS | NECROPSY | ANIMAL | DAY | BODY FLUID AMOUNT | NASAL | BLOOD | URINE | RECTA | RIGHT MIDDLE LOBE | LacZ SEGMENT | CFTR SEGMENT |
| 1.0E+10 | LONG-TERM | CFB15 | | 100 μl of body fluid | − | − | − | − | | | |
| | | | | 10 μl of body fluid | − | − | − | − | | | |
| | | | 4 | 100 μl of body fluid | − | − | − | − | | | |
| | | | | 10 μl of body fluid | − | − | − | − | | | |
| | 4 DAY | CFB4 | 0 | 100 μl of body fluid | − | − | − | − | | | |
| | | | | 10 μl of body fluid | − | − | − | − | | | |
| | | | 4 | 100 μl of body fluid | − | − | − | − | − | − | − |
| | | | | 10 μl of body fluid | − | − | − | − | − | − | − |
| | 21 DAY | CFB6 | 0 | 100 μl of body fluid | − | − | − | − | | | |
| | | | | 10 μl of body fluid | − | − | − | − | | | |
| | | | 4 | 100 μl of body fluid | − | − | − | − | | | |
| | | | | 10 μl of body fluid | − | − | − | − | | | |
| | | | 15 | 100 μl of body fluid | − | − | − | − | | | |
| | | | | 10 μl of body fluid | − | − | − | − | | | |
| | | | 21 | 100 μl of body fluid | − | − | − | − | | | |
| | | | | 10 μl of body fluid | − | − | − | − | | | |
| STUDY III | LONG-TERM | CFB8 | 0 | 100 μl of body fluid | − | − | − | − | | | |
| | | | | 10 μl of body fluid | − | − | − | − | | | |
| | | | 4 | 100 μl of body fluid | − | − | − | − | − | − | − |
| | | | | 10 μl of body fluid | − | − | − | − | − | − | − |
| | | | 15 | 100 μl of body fluid | − | − | − | − | | | |
| | | | | 10 μl of body fluid | − | − | − | − | | | |
| | | | 21 | 100 μl of body fluid | − | − | − | − | − | − | − |
| | | | | 10 μl of body fluid | − | − | − | − | − | − | − |

TABLE X

| Addendum - General Adenovirus Positive Control Results | | | | | | | |
|---|---|---|---|---|---|---|---|
| | | CYTOPATHIC EFFECT (Scale: −, ±, +; P = pending) Particles per Plate | | | | | |
| DATE | DAY | 10,000 | 1,000 | 100 | 10 | 1 | 0 |
| CFB3–CFB8 | | | | | | | |
| 1/17/89 | 0 | + | + | + | ± | ± | − |
| 1/21/89 | 4 | + | + | + | ± | ± | − |
| 2/1/89 | 15 | | + | + | ± | ± | − |
| 2/7/89 | 21 | | + | ± | ± | − | − |
| CFB10–CFB16 | | | | | | | |
| 2/15/89 | 0 | | + | ± | ± | − | − |

We claim:

1. An adenoviral vector which comprises an E2 region having a temperature sensitive mutation and a deletion of the E1 region.

2. The vector of claim 1 wherein the mutation is ts125.

3. The vector of claims 1 and 2 further comprising the gene for cystic fibrosis transmembrane regulator operatively-linked thereto.

4. A method of treatment of a defect in a gene in a target cell comprising the step of transferring into the cell a therapeutically effective amount of an adenoviral vector having the gene for cystic fibrosis transmembrane regulator operatively linked thereto, wherein the adenoviral vector comprises an E2 region comprising a temperature sensitive mutation and a deletion of the E1 region, wherein said gene is expressed inside the target cell.

5. The method of claim 4 wherein the mutation is ts125.

* * * * *